(12) United States Patent
Cao et al.

(10) Patent No.: US 10,577,325 B2
(45) Date of Patent: Mar. 3, 2020

(54) METHOD FOR PREPARING A SERIES OF CARBAZOLE DERIVATIVES AND USE THEREOF IN ORGANIC LIGHT-EMITTING DIODES

(71) Applicant: SHIJIAZHUANG CHENGZHI YONGHUA DISPLAY MATERIAL CO., LTD., Shijiazhuang, Hebei Prov. (CN)

(72) Inventors: Jianhua Cao, Shijiazhuang (CN); Shibo Wang, Shijiazhuang (CN); Ruimao Hua, Shijiazhuang (CN)

(73) Assignee: SHIJIAZHUANG CHENGZHI YONGHUA DISPLAY MATERIAL CO., LTD., Shijiazhuang, Hebei Prov. (CN)

( * ) Notice: Subject to any disclaimer, the term of this patent is extended or adjusted under 35 U.S.C. 154(b) by 171 days.

(21) Appl. No.: 15/714,295

(22) Filed: Sep. 25, 2017

(65) Prior Publication Data
US 2018/0282277 A1     Oct. 4, 2018

(30) Foreign Application Priority Data
Mar. 28, 2017   (CN) .......................... 2017 1 0193446

(51) Int. Cl.
*C07D 209/86*     (2006.01)
*C07D 209/88*     (2006.01)
(Continued)

(52) U.S. Cl.
CPC ......... *C07D 209/88* (2013.01); *C07D 209/86* (2013.01); *C09K 11/06* (2013.01);
(Continued)

(58) Field of Classification Search
CPC ........................... C07D 209/86; C07D 209/88
See application file for complete search history.

(56) References Cited

FOREIGN PATENT DOCUMENTS

| CN | 103936653 A | * | 7/2014 | .......... C07D 209/82 |
| EP | 3010068 A1 | * | 4/2016 | ........ H01L 51/0059 |

(Continued)

OTHER PUBLICATIONS

Machine Translation of JP 2015-129240-A.*
(Continued)

*Primary Examiner* — Vu A Nguyen
(74) *Attorney, Agent, or Firm* — Muncy, Geissler, Olds & Lowe, PC

(57) ABSTRACT

Disclosed are a method for preparing a series of carbazole derivatives and use thereof in organic light-emitting diodes. The structure of the material is as shown in Formula I. An organic electroluminescent device prepared by the material can have a significantly improved power efficiency and an external quantum efficiency for the device and an extended life for an orange light or red light device; moreover, the material has characteristics, for example, methods for the synthesis and purification of the material are simple and suitable for large-scale production, and is an ideal choice as a luminescent material for organic electroluminescent (Continued)

devices. The use of the organic electroluminescent diode material as a carrier transport material or as a luminescent material alone or as a host material in a light-emitting layer also falls within the scope of protection.

Formula I

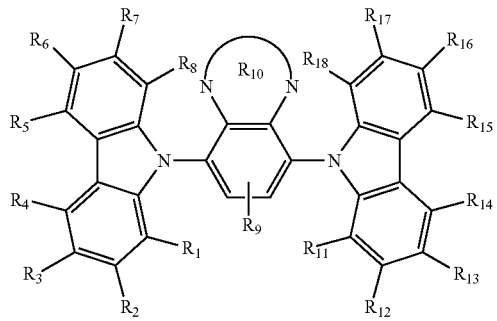

7 Claims, 4 Drawing Sheets

(51) Int. Cl.
H01L 51/00 (2006.01)
H01L 51/50 (2006.01)
C09K 11/06 (2006.01)

(52) U.S. Cl.
CPC ...... *H01L 51/0052* (2013.01); *H01L 51/0059* (2013.01); *H01L 51/0072* (2013.01); *H01L 51/0082* (2013.01); *H01L 51/5048* (2013.01); *H01L 51/5056* (2013.01); *H01L 51/5072* (2013.01); *C09K 2211/1029* (2013.01); *C09K 2211/1066* (2013.01); *C09K 2211/18* (2013.01); *H01L 51/0085* (2013.01); *H01L 51/5012* (2013.01); *H01L 51/5016* (2013.01); *H01L 2251/558* (2013.01)

(56) References Cited

FOREIGN PATENT DOCUMENTS

JP 2015129240 A * 7/2015 .......... C07D 417/14
WO WO-2011093309 A1 * 8/2011 .......... H01L 51/004

OTHER PUBLICATIONS

SciFinder Searches (May 8, 2019).*
Yu et al., Dye and Pigments 141 (2017) 325-332.*
Computer-generated English-language translation of CN 103936653A.*
SciFinder Search (Sep. 20, 2019).*

* cited by examiner

METHOD FOR PREPARING A SERIES OF CARBAZOLE DERIVATIVES AND USE THEREOF IN ORGANIC LIGHT-EMITTING DIODES

TECHNICAL FIELD

The present invention belongs to the field of organic electroluminescent display technologies and relates to a method for preparing a series of fluorescent materials and use thereof in organic electroluminescent diodes, and particularly to a series of carbazole derivatives and an organic electroluminescent device.

BACKGROUND ART

For organic electroluminescence (abbreviated as OLED) and related researches, pope et al., first discovered the electroluminescence phenomenon of an organic compound, monocrystalline anthracene in 1963. In 1987, the Kodak Company of U.S. fabricated an amorphous film-type device using a method for the evaporation of organic small molecules, which reduces the drive voltage to 20 V or lower. Such devices can be widely used in flat panel displays and surface light sources due to having advantages of being ultrathin, all solid state, self-illumination, a high brightness, a wide viewing angle, a fast response speed, a ow drive voltage, a low power consumption, a bright colour, a high contrast ratio, a simple technological process, good temperature characteristics, being capable of achieving a flexible display, etc., and therefore has been widely studied, developed and used.

After 20 years of development, organic EL materials have fully realized red, blue and green luminescence, and the application field has also been extended to areas such as macromolecules and metal complexes from small molecules. In recent years, the organic electroluminescence display technology has become mature, and some products have entered the market; however, in the process of industrialization, there are still many problems to be solved urgently, particularly various organic materials for manufacturing devices, there are still many problems that have not been solved yet, e.g., the carrier injection, transmission performance, material luminous performance, service life, and colour purity thereof, the match between the various materials and between various electrodes. Especially, the luminous efficiency and service life of light-emitting devices have not met the practical requirements yet, which greatly limits the development of the OLED technology. However, the use of triplet state-luminescent metal complex phosphorescent materials provides a high luminous efficiency, wherein green and red light materials thereof have met the service requirements, but the special electronic structure characteristics of the metal complex results in that the blue light material cannot meet the service requirements.

The appearance of a thermally activated delayed fluorescent material between fluorescence and phosphorescence greatly increases the luminous efficiency of the fluorescent material, which almost achieves the luminous efficiency of a phosphorescent material, and makes up for the deficiency of the phosphorescent blue light material, while avoiding the use of noble rare metals, greatly reducing the material cost. However, the thermally activated delayed fluorescent materials that have been reported can be used for preparing OLED devices only by a doping method due to the presence of an aggregation-caused quenching effect in the solid state. Therefore, it is an approach to solve the above-mentioned problems by developing a thermally activated delayed fluorescent material having an aggregation-induced emission effect in the solid state.

DISCLOSURE OF THE INVENTION

An object of the present invention is to provide an efficient fluorescent material and use thereof in organic electroluminescent diodes.

The organic electroluminescent materials provided by the invention have a structural general formula as shown in Formula I,

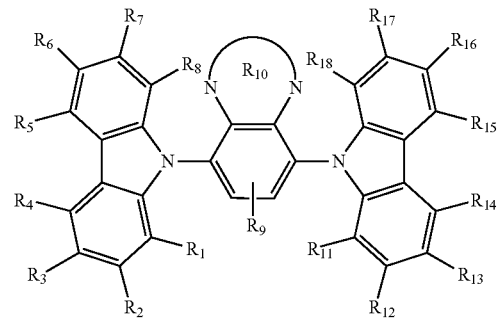

Formula I wherein $R_1$, $R_4$, $R_5$, $R_8$, $R_9$, $R_{11}$, $R_{14}$, $R_{15}$ and $R_{18}$ are each independently selected from any one of hydrogen, $C_1$-$C_{10}$ alkyl, $C_2$-$C_{10}$ alkenyl, $C_2$-$C_{10}$ alkynyl, $C_1$-$C_{10}$ alkoxy, $C_3$-$C_{10}$ cycloalkyl, $C_3$-$C_{10}$ cycloalkenyl, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ arylphosphino group, a substituted or unsubstituted $C_6$-$C_{60}$ arylsilyl group, a substituted or unsubstituted $C_6$-$C_{60}$ aryl boryl group, and a substituted or unsubstituted $C_2$-$C_{60}$ heterocyclic aryl group, said substituting substituents being selected from one or more of hydrogen, deuterium, a halogen atom, hydroxyl, a nitrile group, nitro, amino, amidino, hydrazino, a hydrazone group, carboxyl or a carboxylate salt thereof, a sulphonic acid group or a sulphonate salt thereof, a phosphoric acid group or a phosphate salt thereof, $C_1$-$C_{10}$ alkyl, $C_2$-$C_{10}$ alkenyl, $C_2$-$C_{10}$ alkynyl, alkoxy, $C_3$-$C_{10}$ cycloalkyl, and $C_3$-$C_{10}$ cycloalkenyl;

$R_2$, $R_3$, $R_6$, $R_7$, $R_{12}$, $R_{13}$, $R_{16}$ and $R_{17}$ are each independently selected from one or more of hydrogen, a substituted or unsubstituted $C_6$-$C_{60}$ aryl group, a substituted or unsubstituted $C_6$-$C_{60}$ arylamino group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl phosphino group, a substituted or unsubstituted $C_6$-$C_{60}$ arylsilyl group, a substituted or unsubstituted $C_6$-$C_{60}$ aryl boryl group, and a substituted or unsubstituted $C_2$-$C_{60}$ heterocyclic aryl group, said substituting substituents being selected from one or more of hydrogen, deuterium, a halogen atom, hydroxyl, a nitrile group, nitro, amino, amidino, hydrazino, a hydrazone group, carboxyl or a carboxylate salt thereof, a sulphonic acid group or a sulphonate salt thereof, a phosphoric acid group or a phosphate salt thereof, $C_1$-$C_{10}$ alkyl, $C_2$-$C_{10}$ alkenyl, $C_2$-$C_{10}$ alkynyl, $C_1$-$C_{10}$ alkoxy, $C_3$-$C_{10}$ cycloalkyl, and $C_3$-$C_{10}$ cycloalkenyl; and $R_{10}$ represents a cyclic structure.

Said substituted or unsubstituted $C_2$-$C_{60}$ heterocyclic aryl group has a cyclic structure comprising at least one of atoms N, O and S;

in particular, said $C_2$-$C_{60}$ heterocyclic aryl group includes the following structures II-1 to II-15:

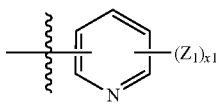
II-1

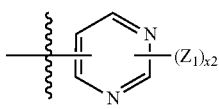
II-2

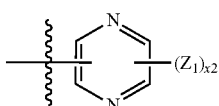
II-3

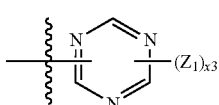
II-4

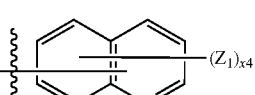
II-5

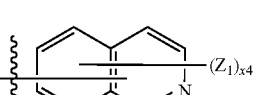
II-6

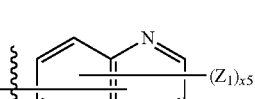
II-7

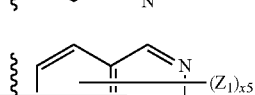
II-8

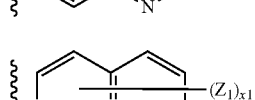
II-9

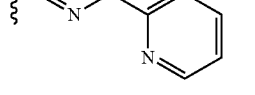
II-10

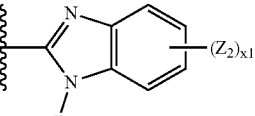

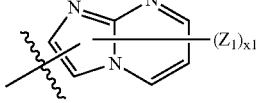
II-11

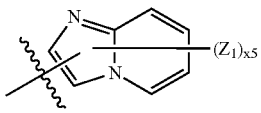
II-12

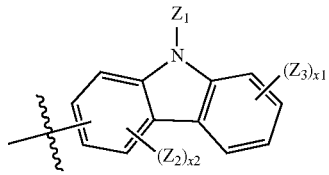
II-13

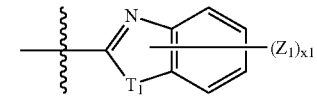
II-14

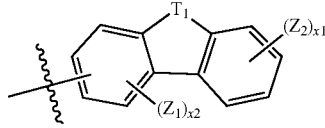
II-15 in said formulae II-1 to II-15, $Z_1$, $Z_2$ and $Z_3$ are independently selected from any one of hydrogen, deuterium, a halogen atom, hydroxyl, a nitrile group, nitro, amino, amidino, hydrazino, a hydrazone group, carboxyl or a carboxylate salt thereof, a sulphonic acid group or a sulphonate salt thereof, a phosphoric acid group or a phosphate salt thereof, $C_1$-$C_{60}$ alkyl, $C_2$-$C_{60}$ alkenyl, $C_2$-$C_{60}$ alkynyl, $C_1$-$C_{60}$ alkoxy, $C_3$-$C_{60}$ cycloalkyl, $C_3$-$C_{60}$ cycloalkenyl, $C_6$-$C_{60}$ aryl, $C_6$-$C_{60}$ aryl containing at least one —F, —CN or $C_1$-$C_{10}$ alkyl, a substituted or unsubstituted $C_6$-$C_{60}$ aryloxy group, a substituted or unsubstituted $C_6$-$C_{60}$ aryl thioether group, and a substituted or unsubstituted $C_2$-$C_{60}$ heterocyclic aryl group;

x1 is an integer of 1 to 4; x2 is an integer of 1 to 3; x3 is an integer of 1 to 2; x4 is an integer of 1 to 6; x5 is an integer of 1 to 5; and $T_1$ is an oxygen or sulphur atom;

in particular, the compound represented by Formula I is any one of the following structural formulae as shown in the following table, but is not limited to the following structures:

A1
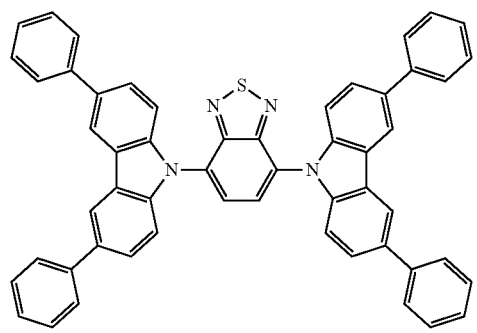
A2
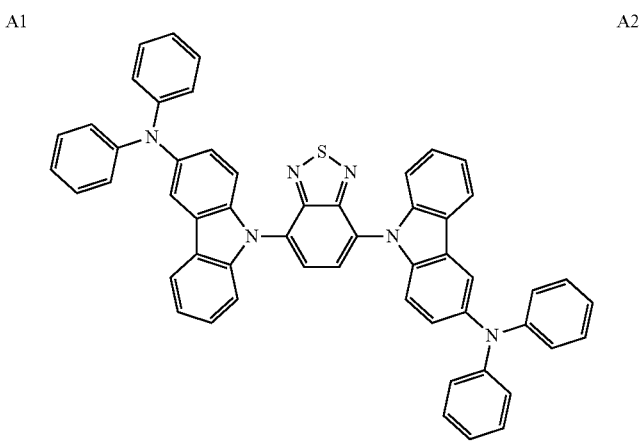
A3
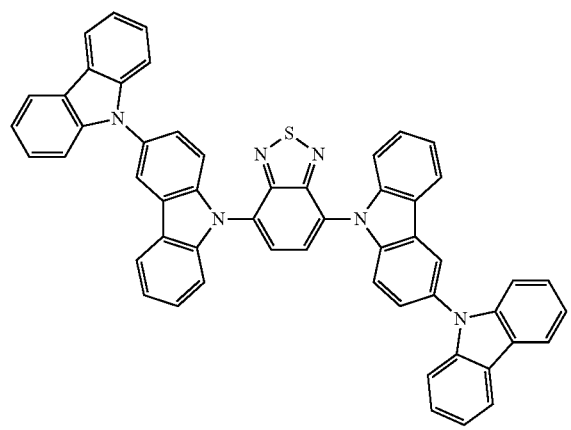
A4
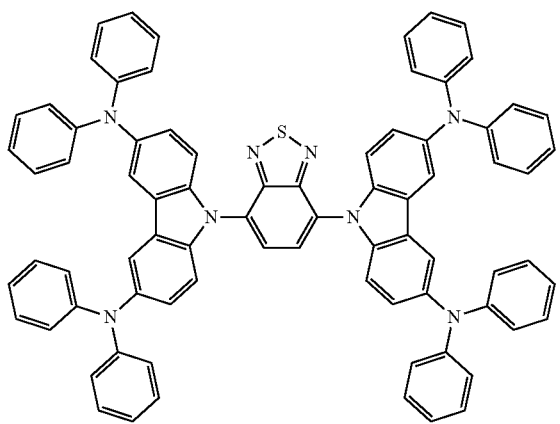
A5
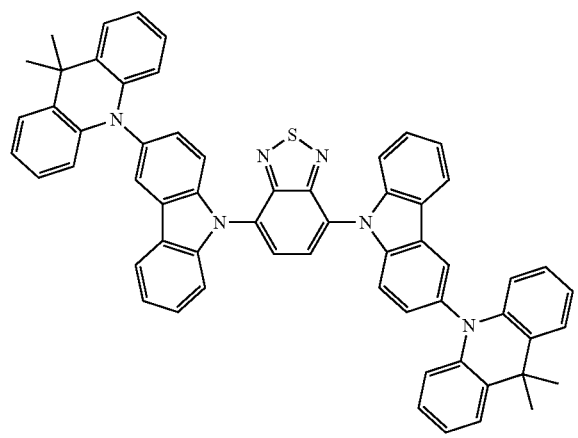
A6
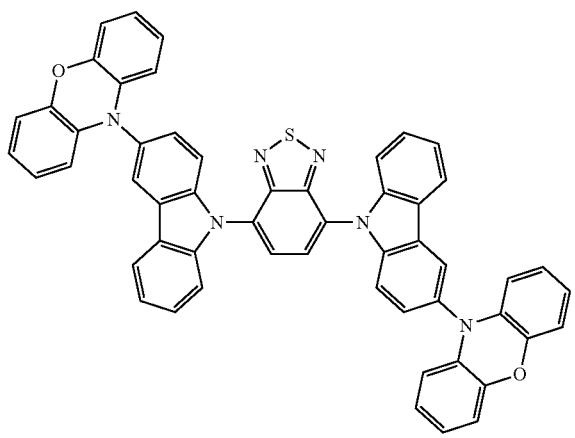

-continued
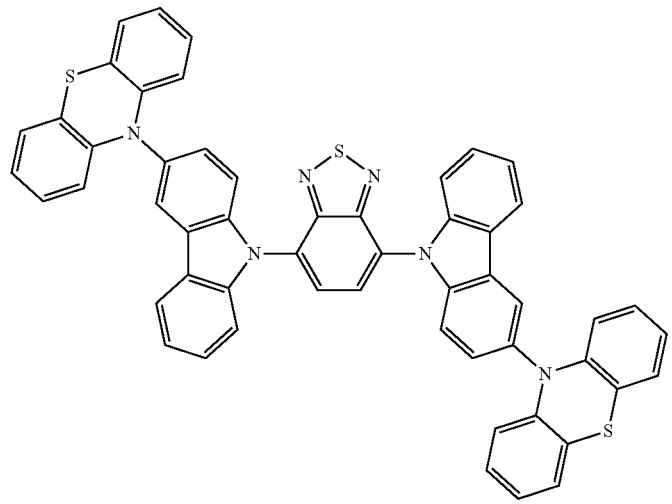
A7
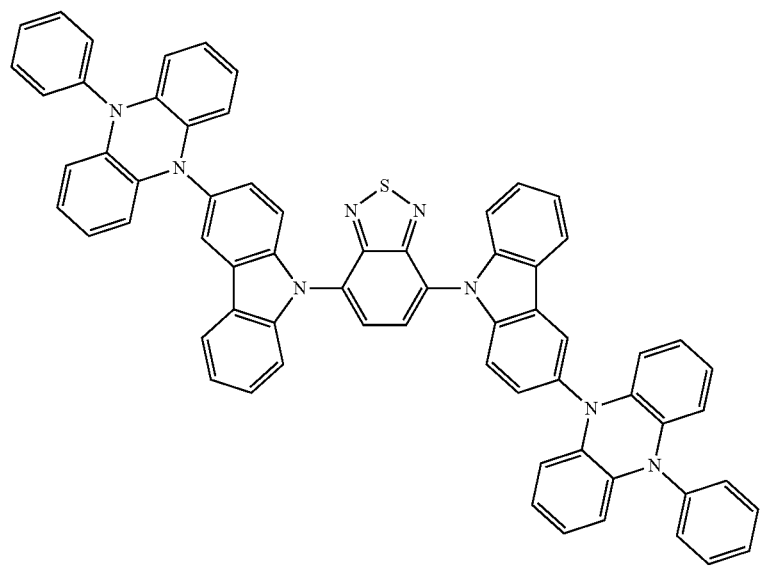
A8
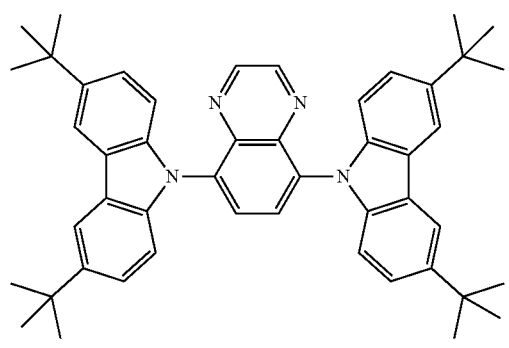
A9
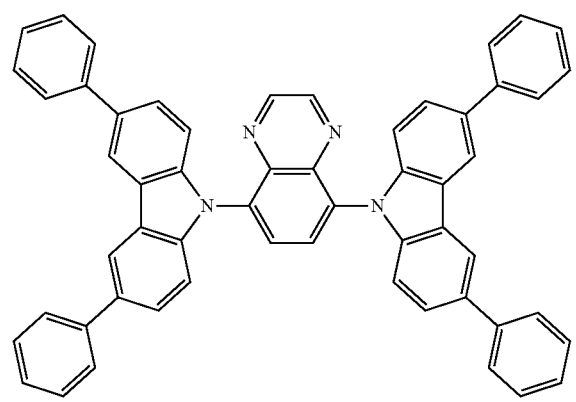
A10

-continued
A11
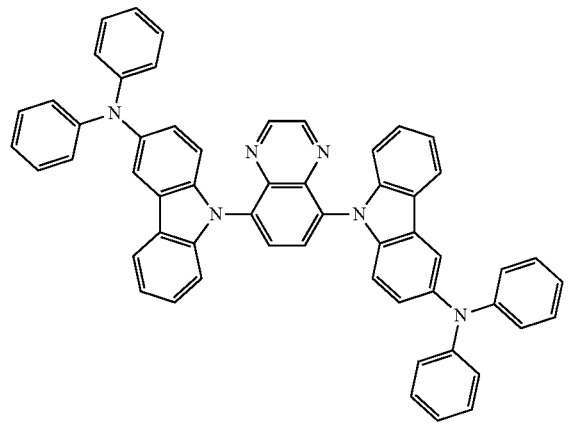
A12
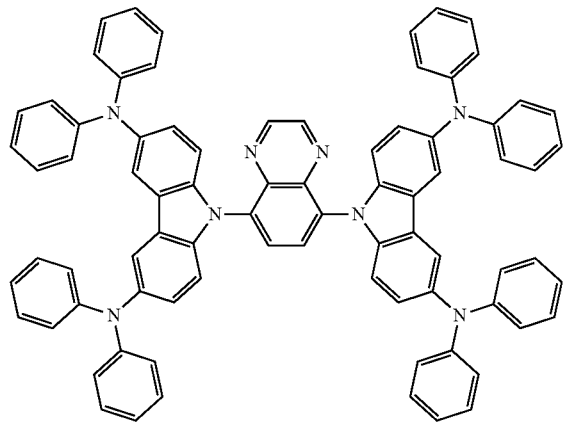
A13
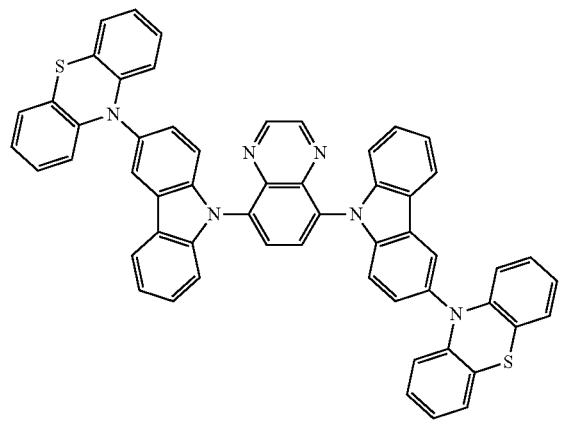
A14
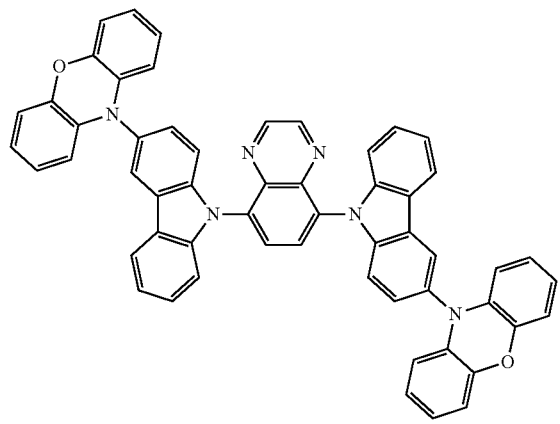
A15
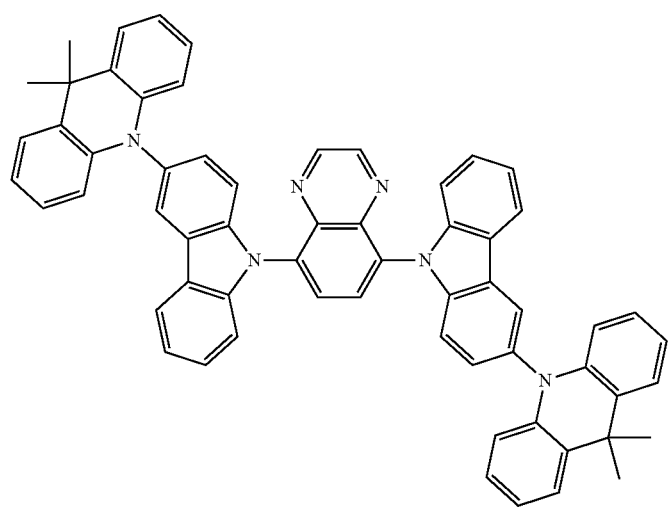

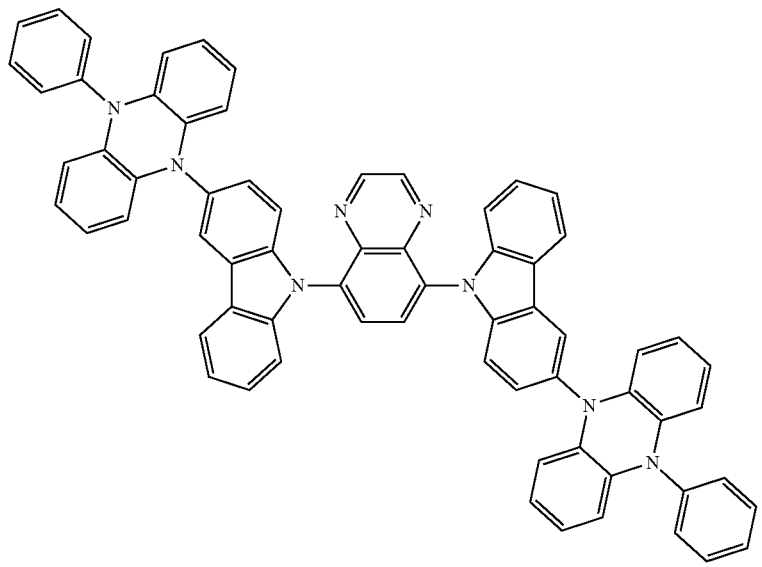
A16
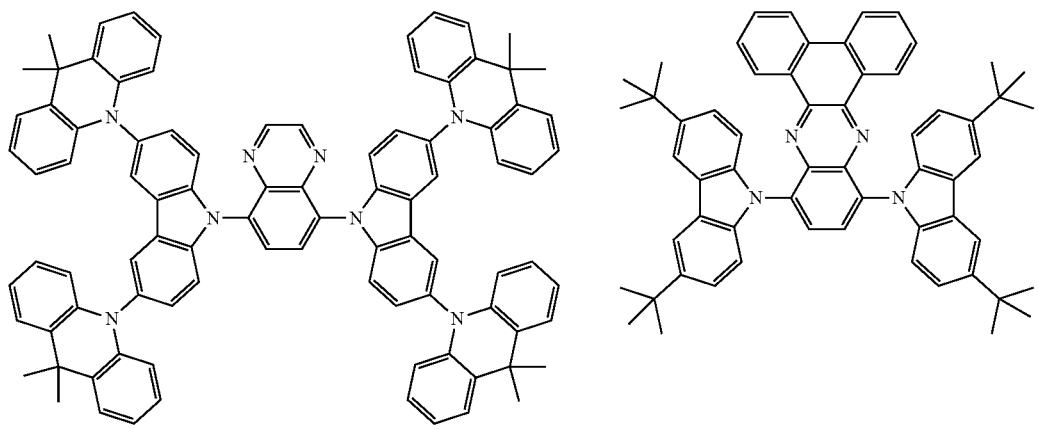
A17 A18
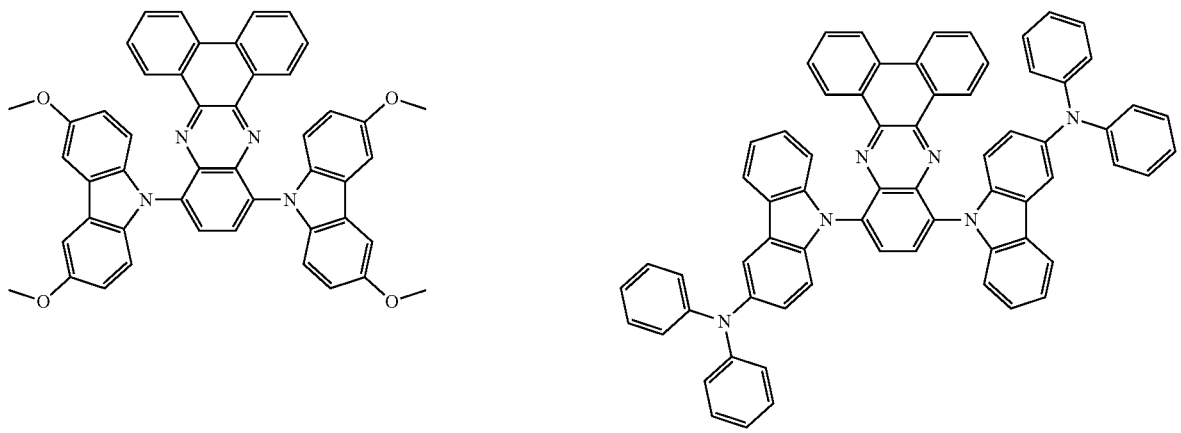
A19 A20

-continued
A21
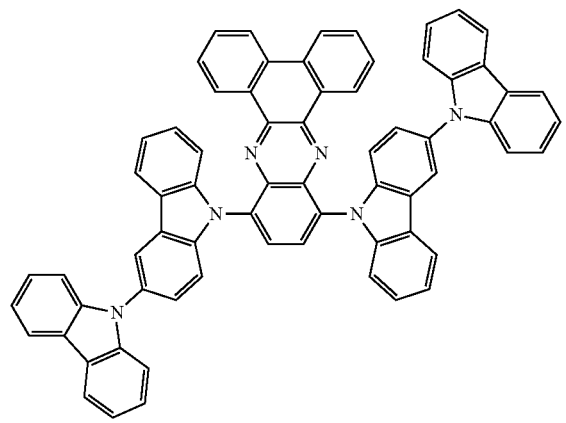
A22
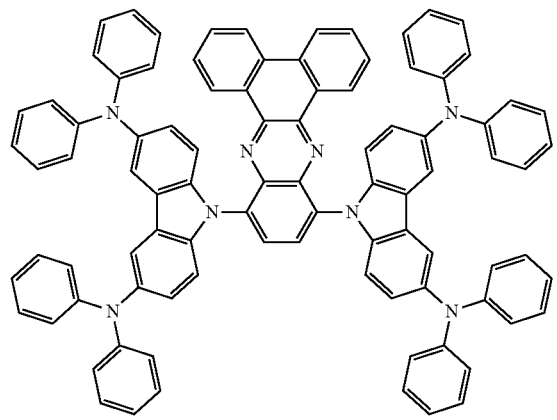
A23
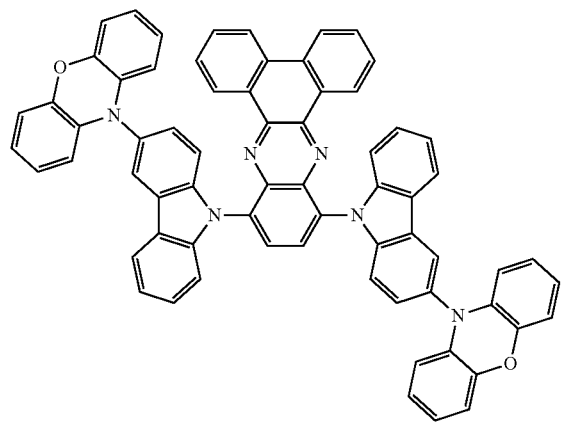
A24
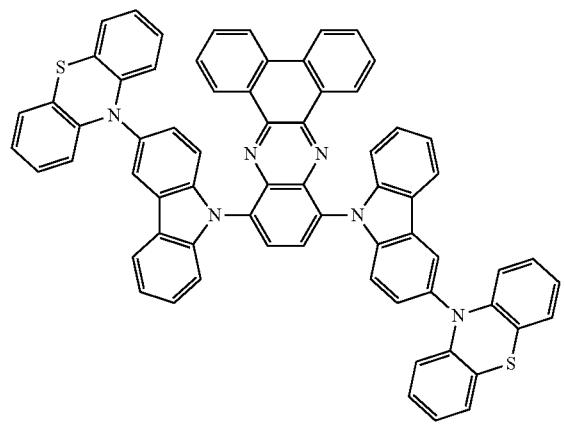
A25
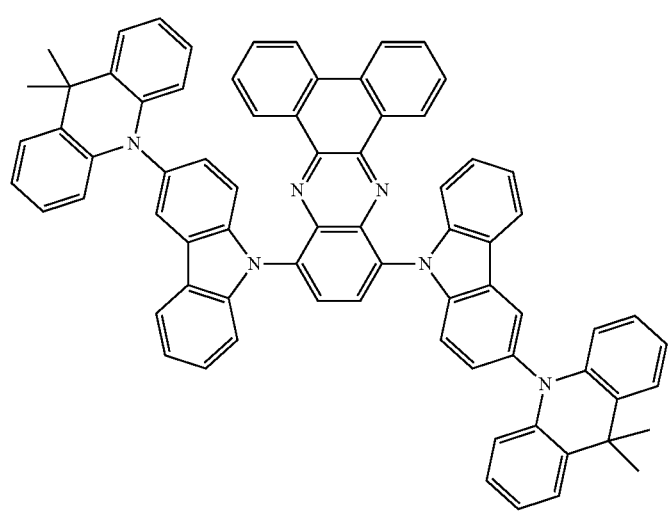

-continued
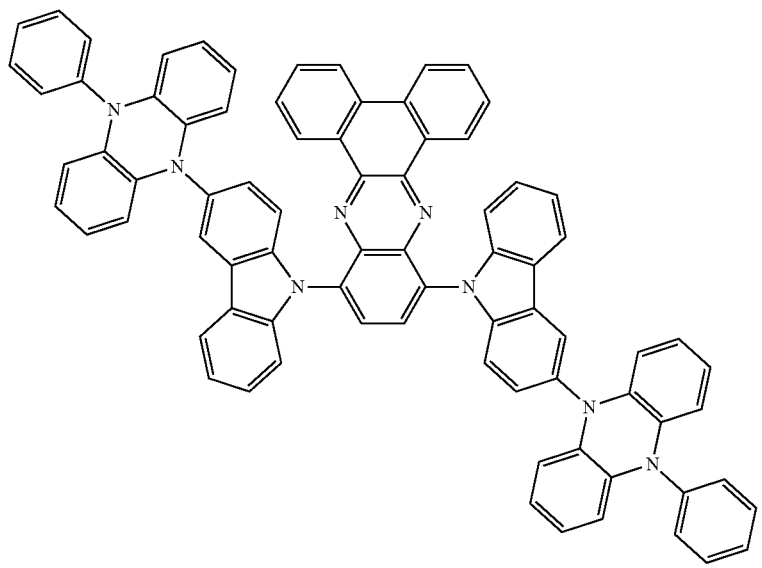
A26
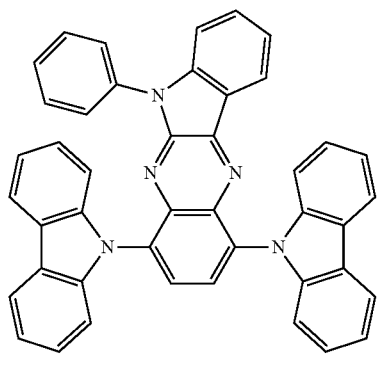
A27
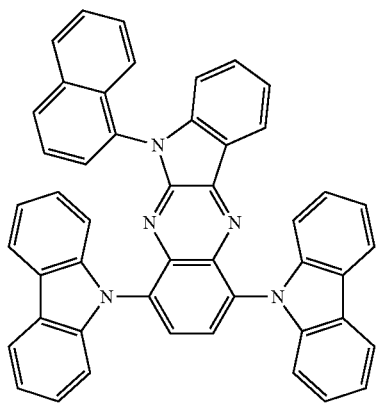
A28
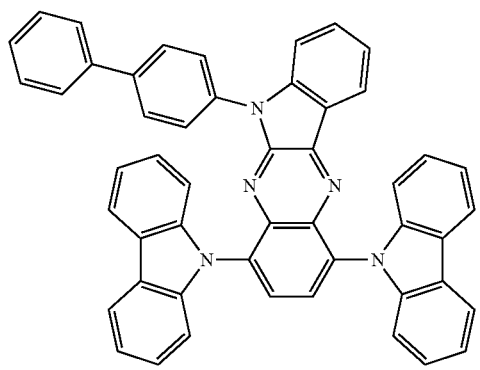
A29
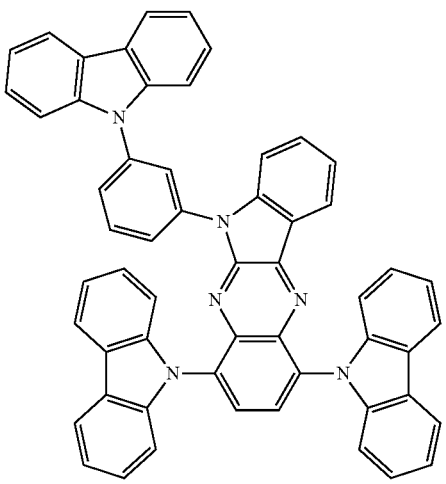
A30

-continued
A31
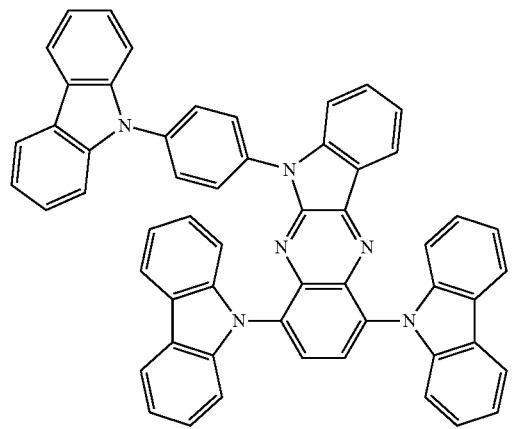
A32
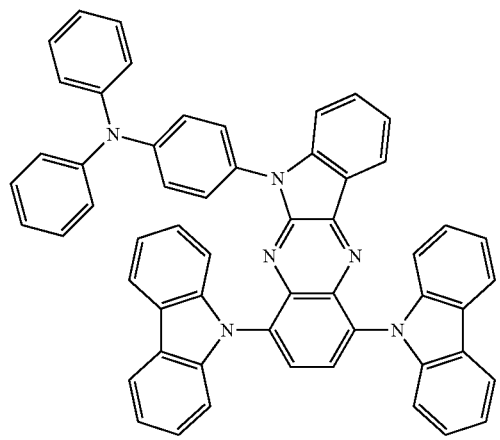
A33
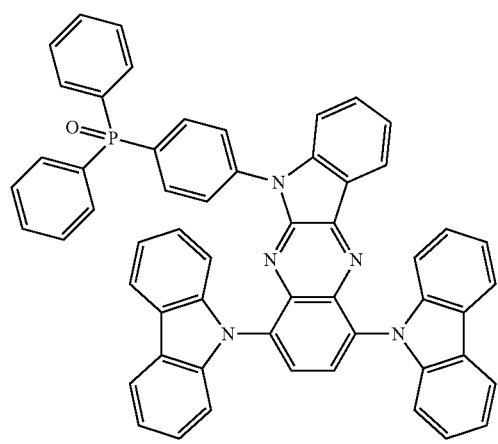
A34
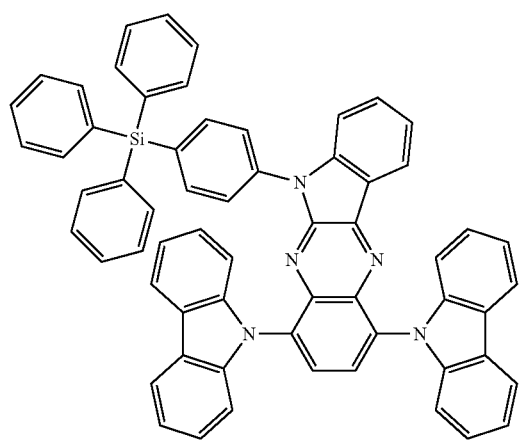
A35
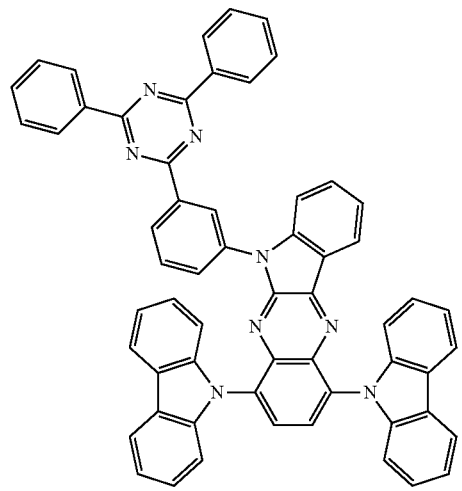
A36
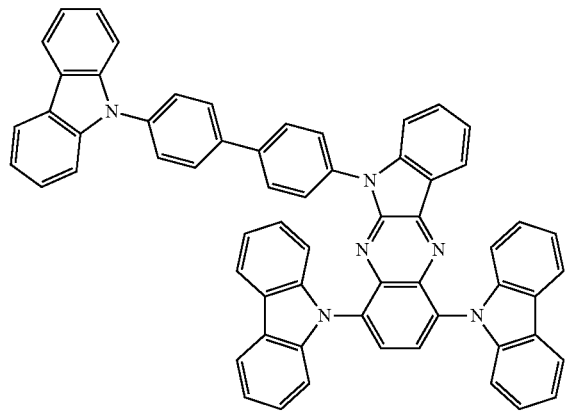

-continued
A37
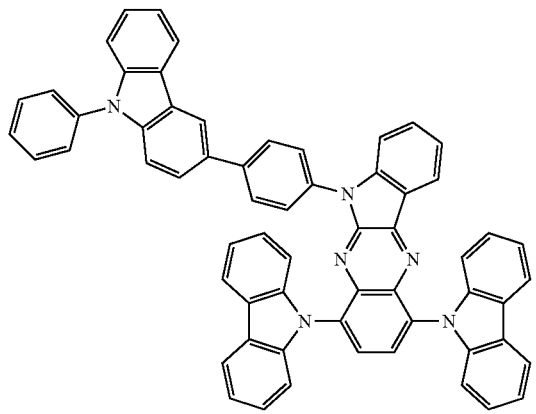
A38
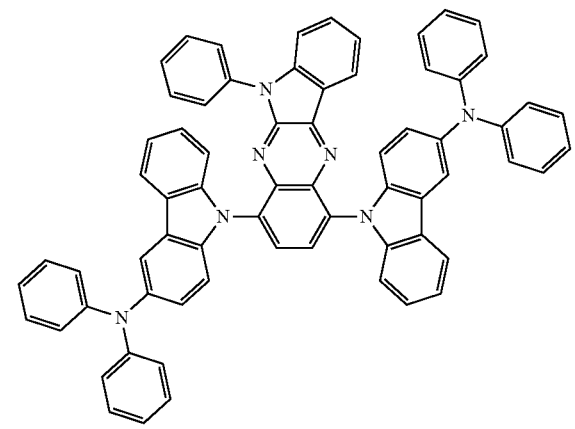
A39
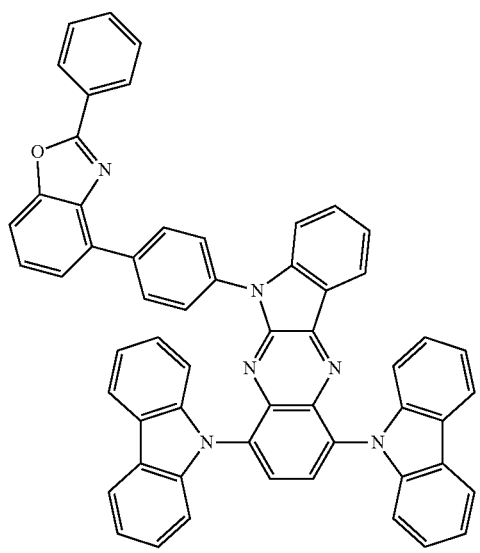
A40
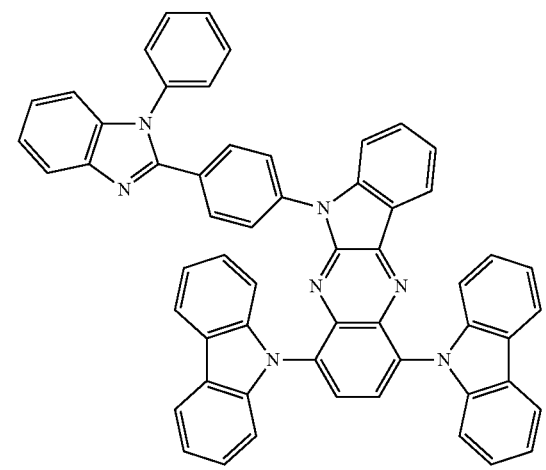
A41
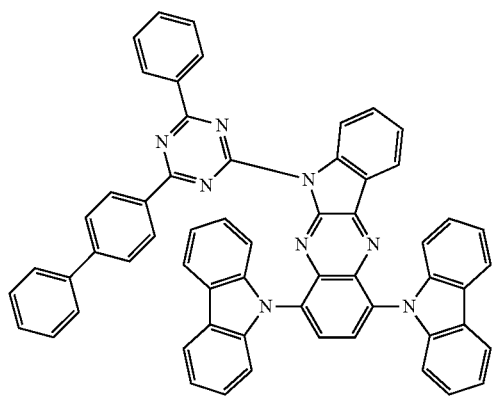
A42
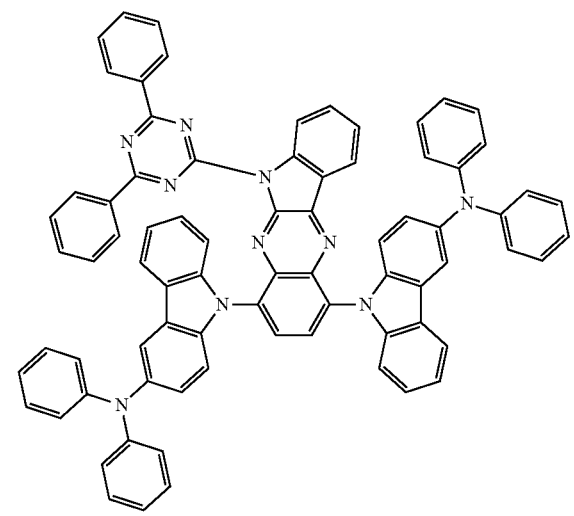

-continued
A43 A44
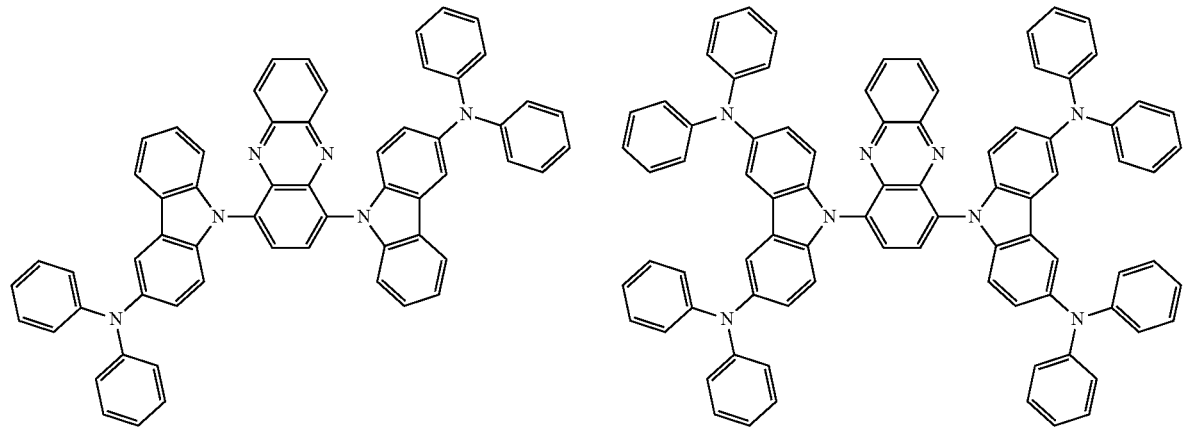
A45 A46
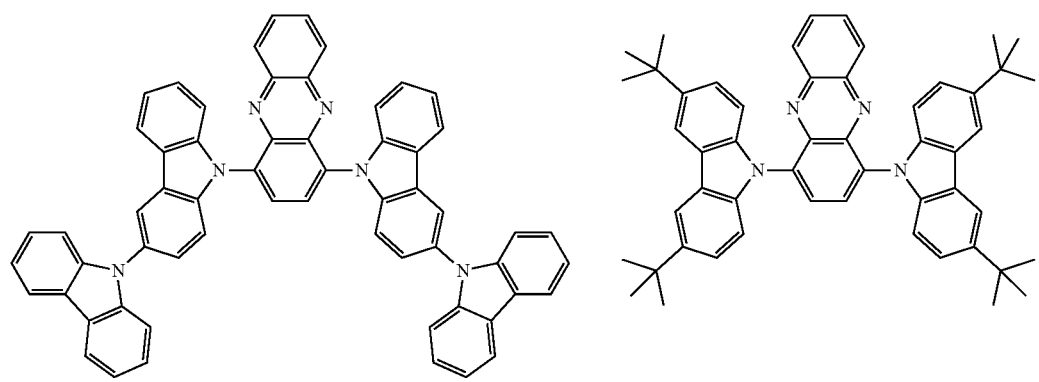
A47 A48
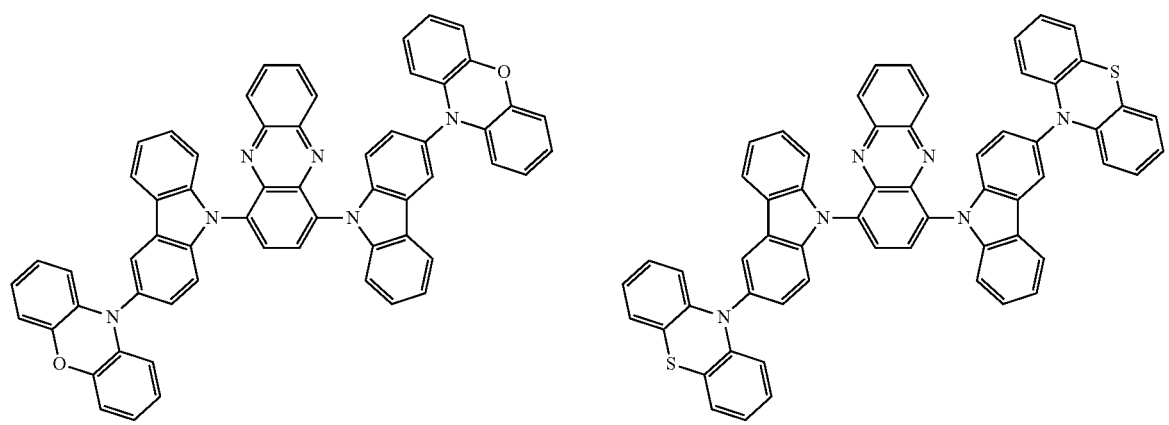

A49
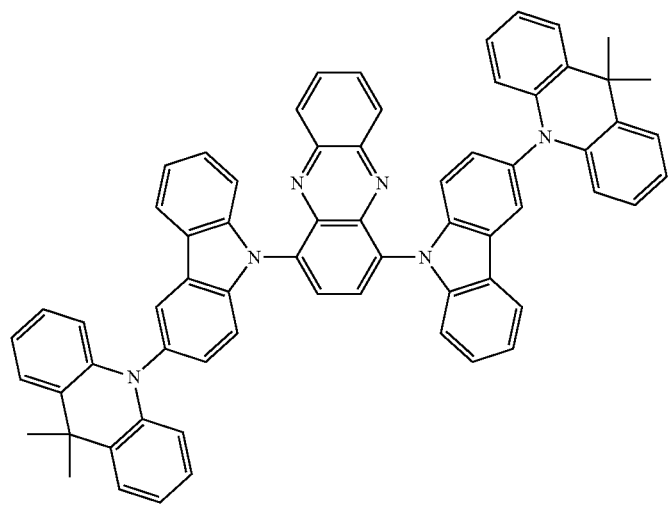
A50
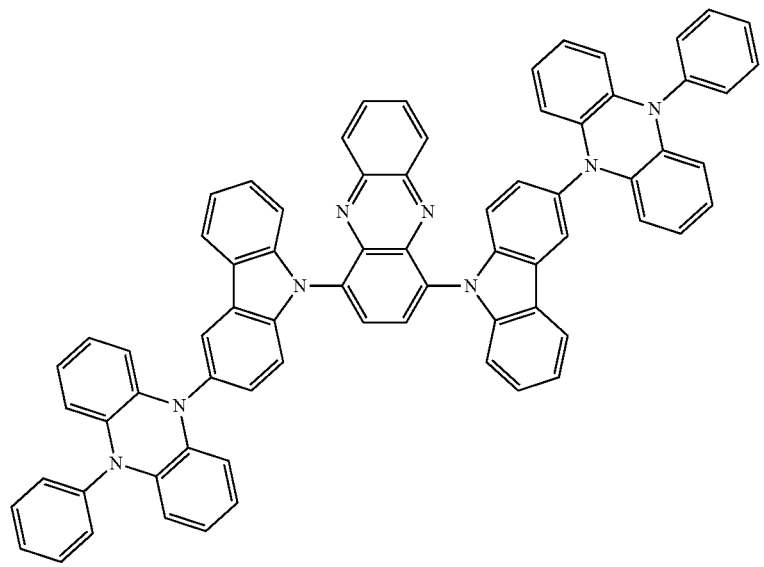
A51
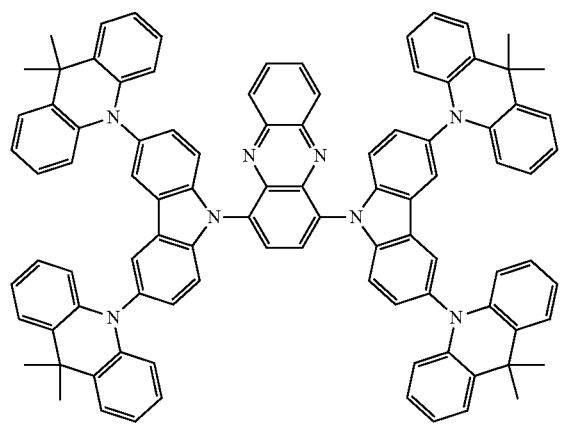
A52
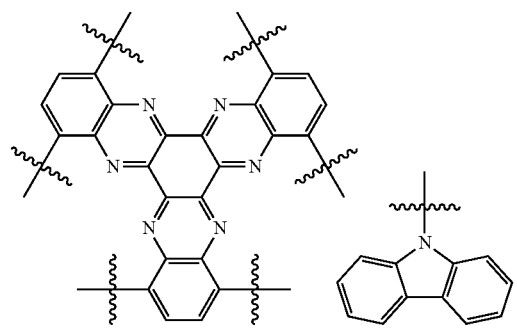

-continued
A53
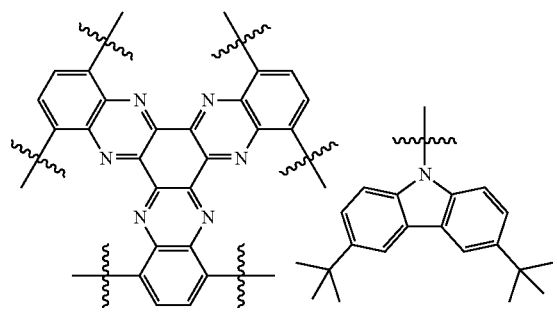
A54
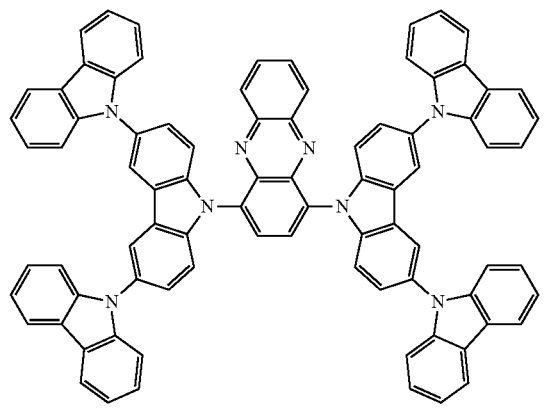
A55
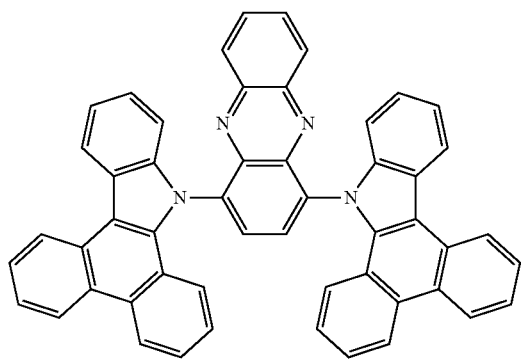
A56
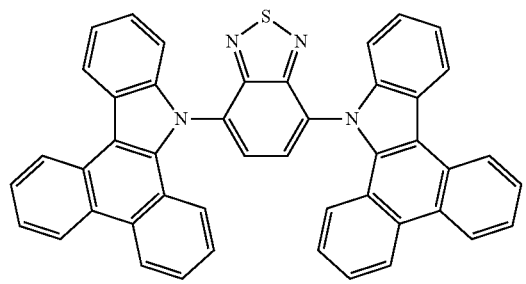
A57
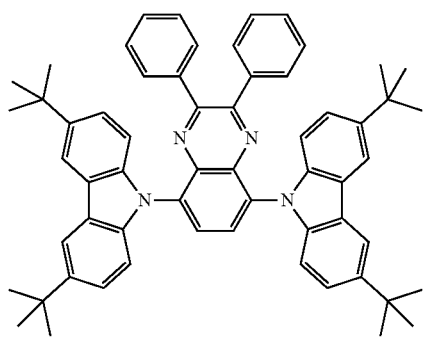
A58
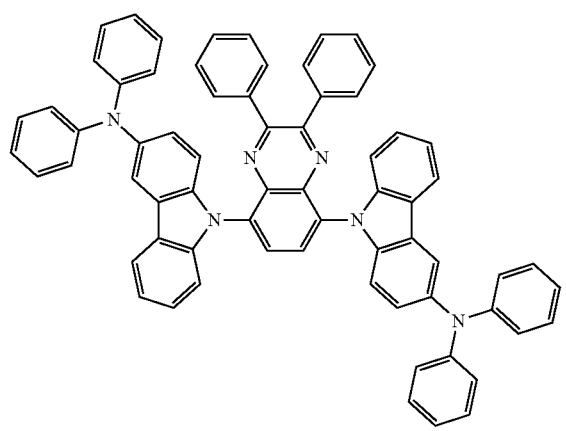

-continued
A59
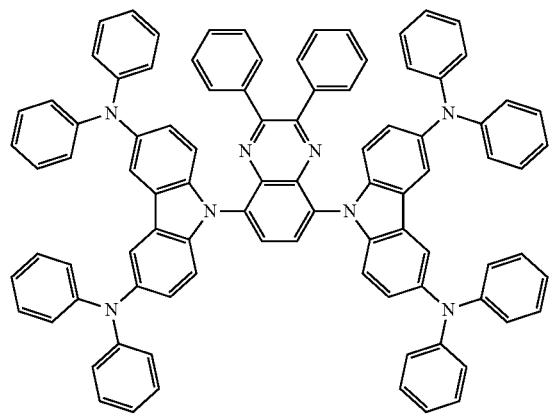
A60
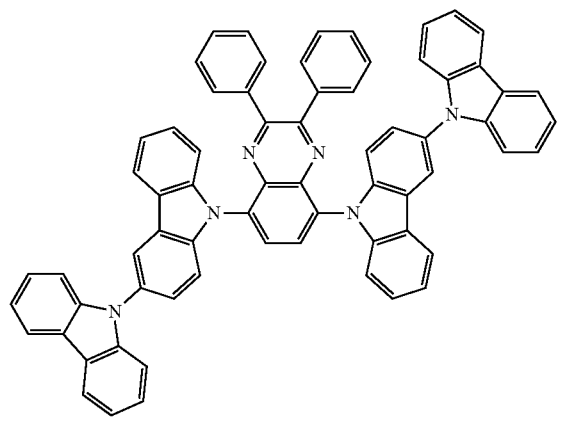
A61
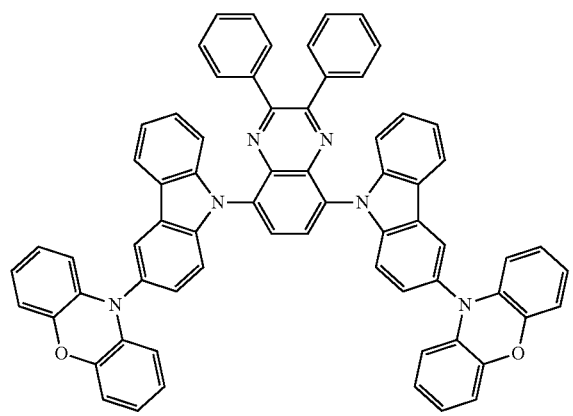
A62
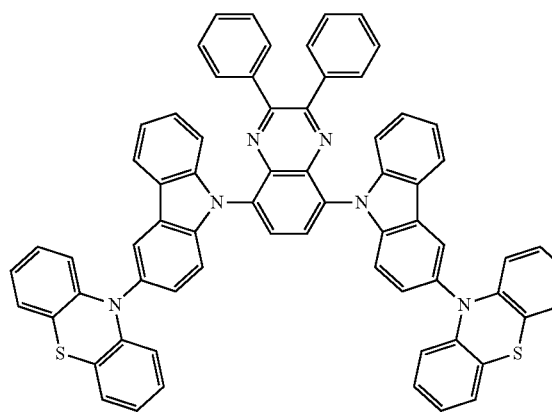
A63
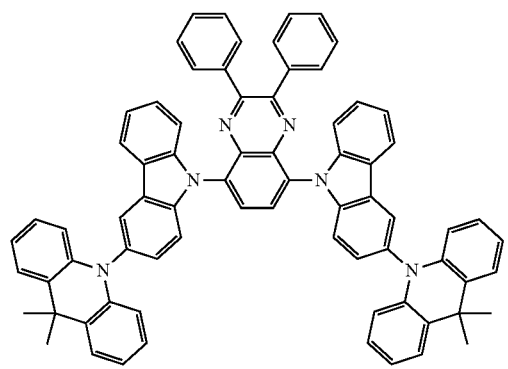
A64
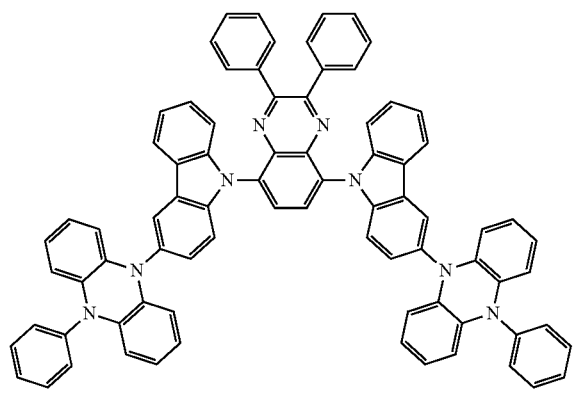

-continued
A65
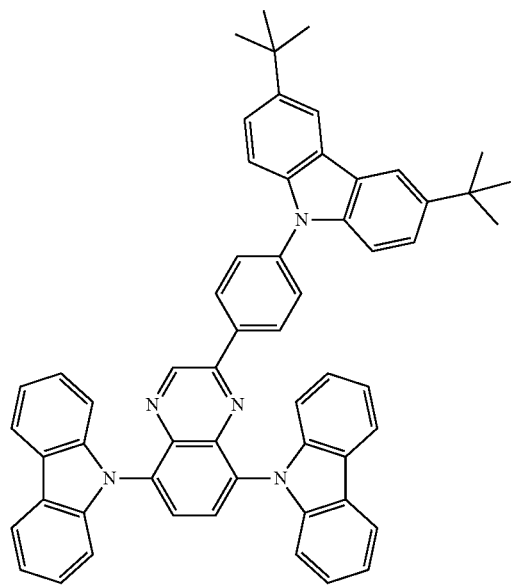
A66
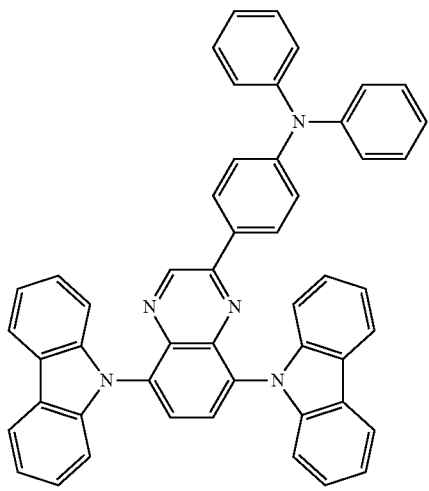
A67
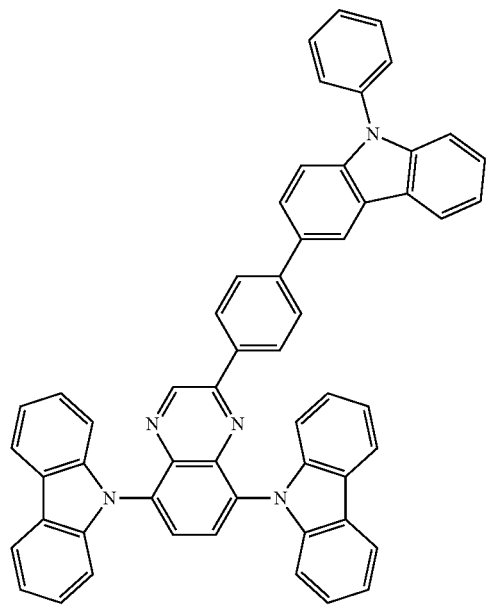
A68
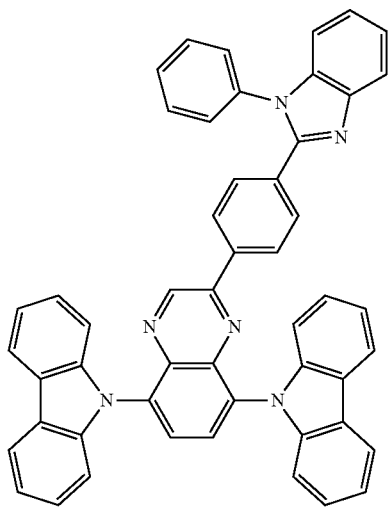

-continued
A69
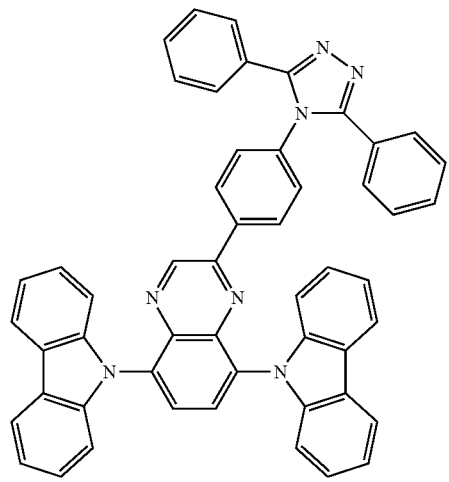
A70
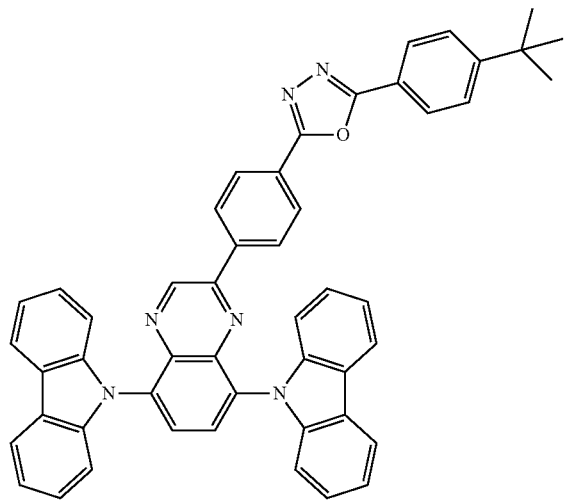
A71
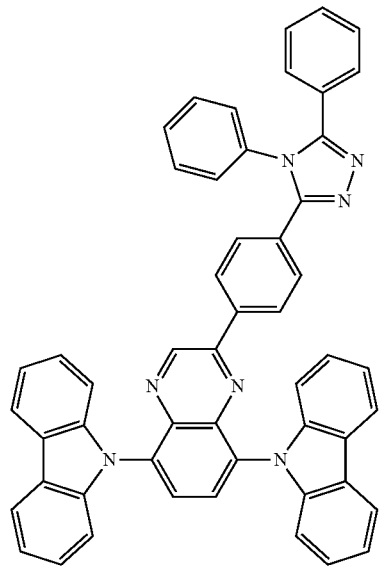
A72
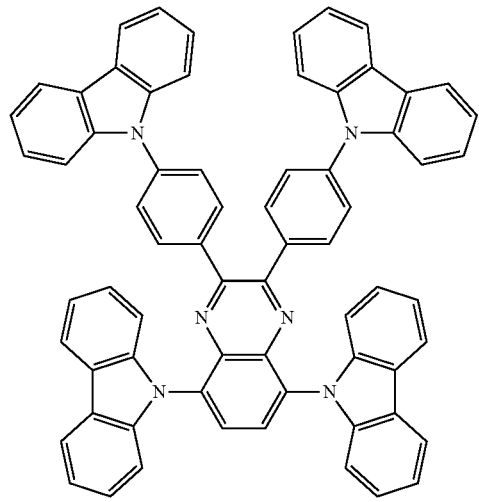
A73
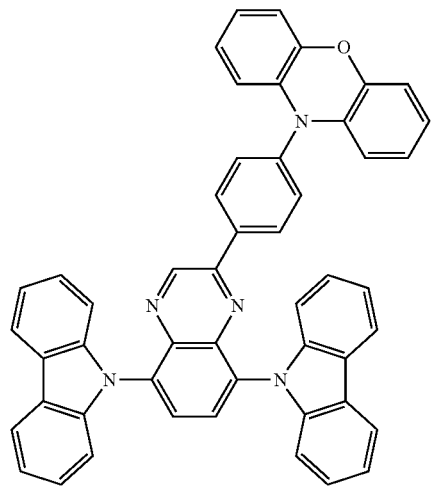
A74
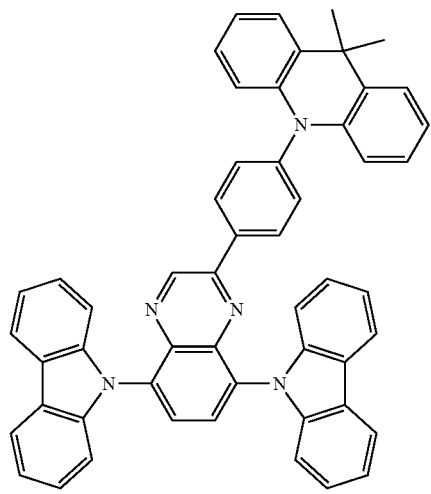

-continued
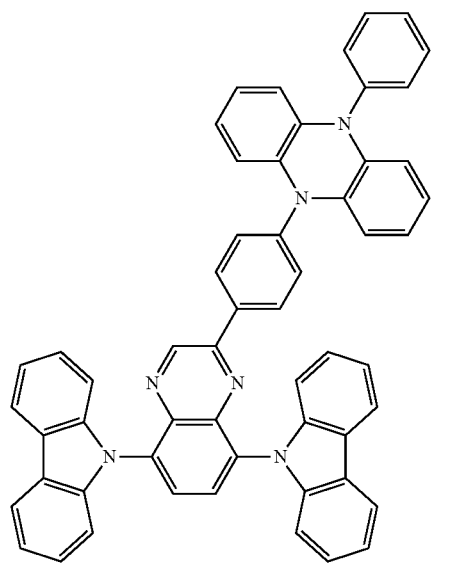
A75
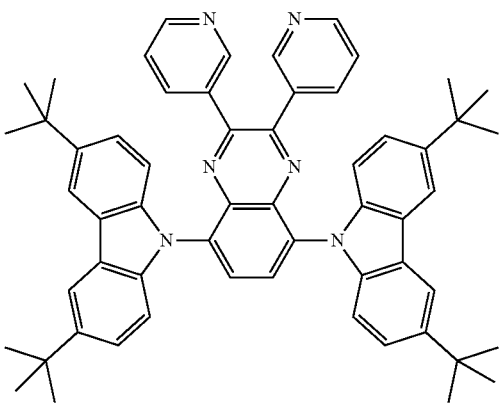
A76
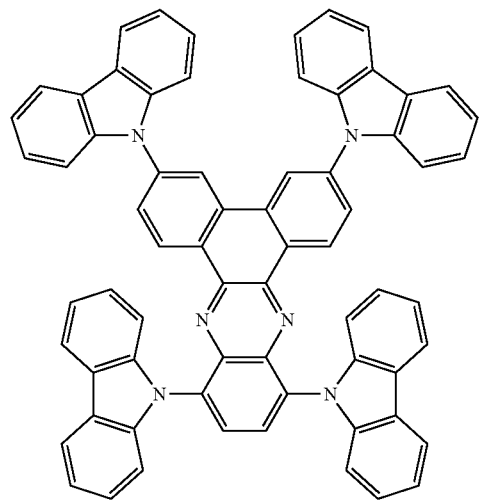
A77
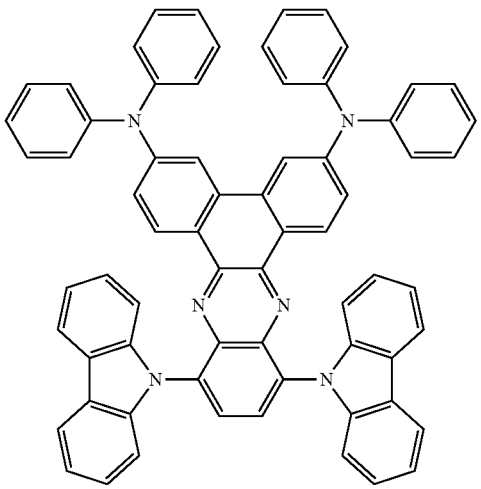
A78
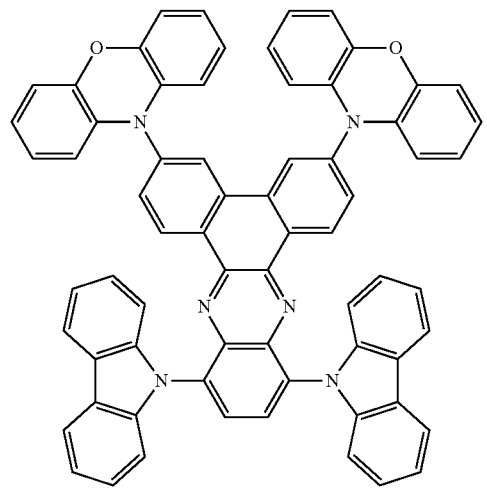
A79
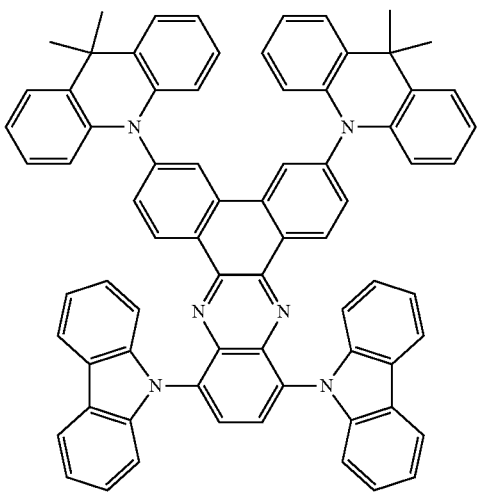
A80

-continued
A81
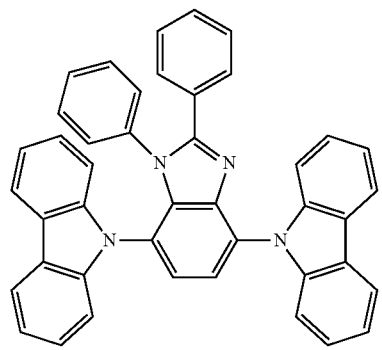
A82
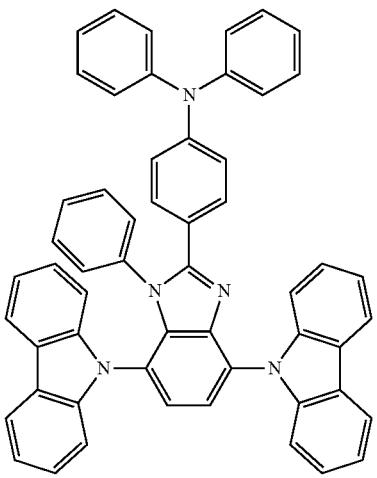
A83
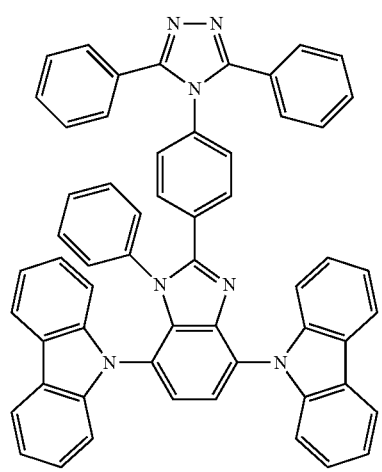
A84
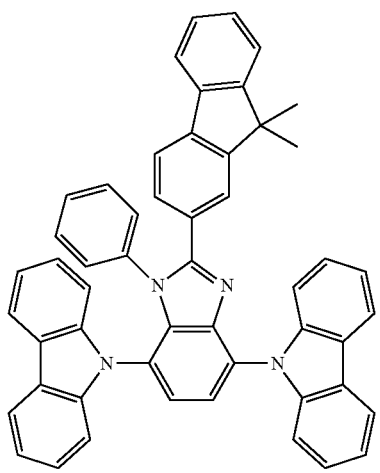
A85
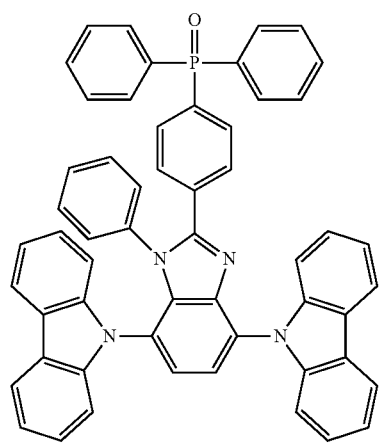
A86
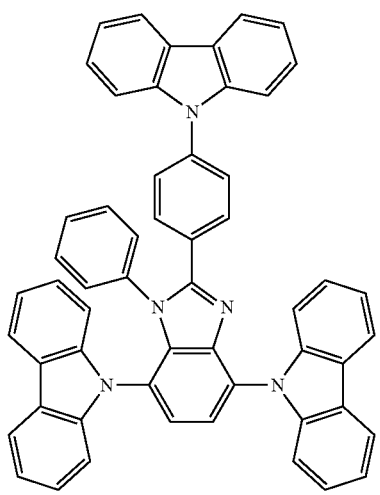

-continued
A87
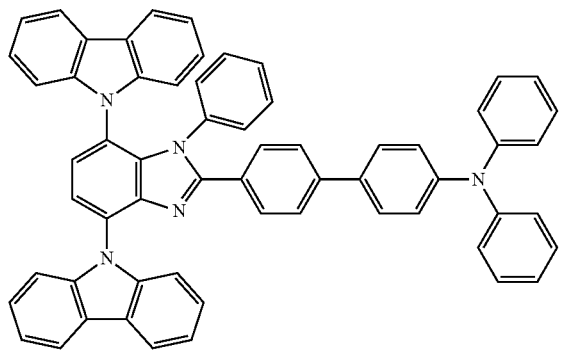
A88
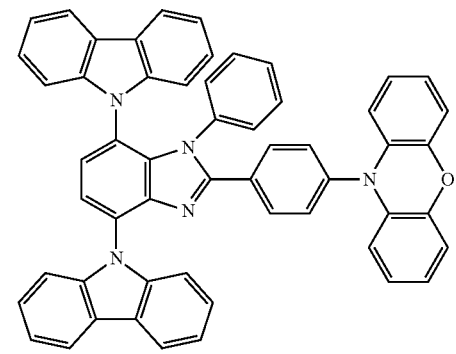
A89
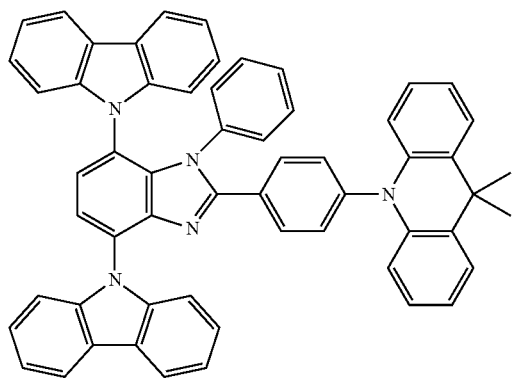
A90
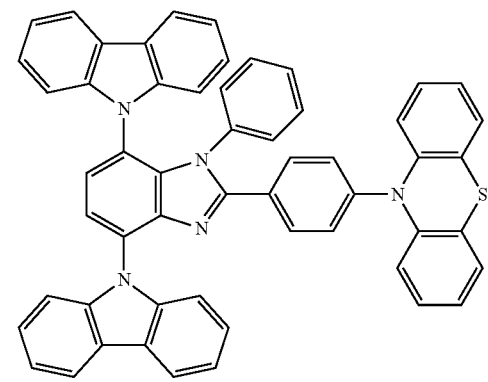
A91
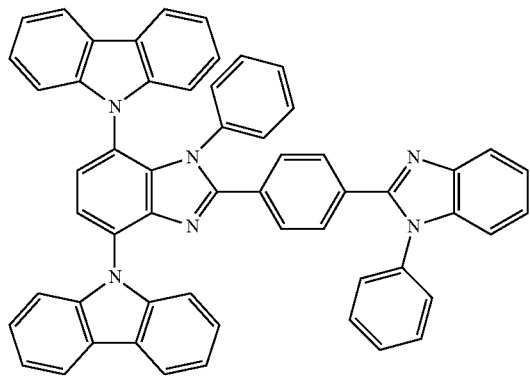
A92
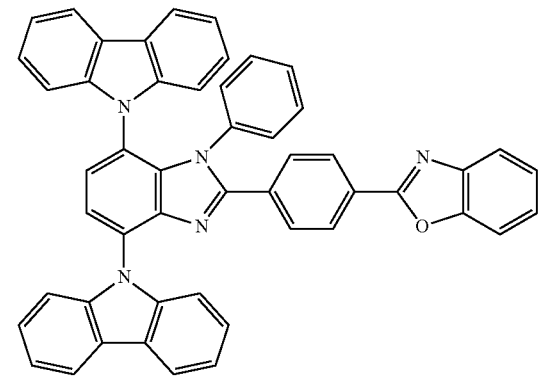
A93
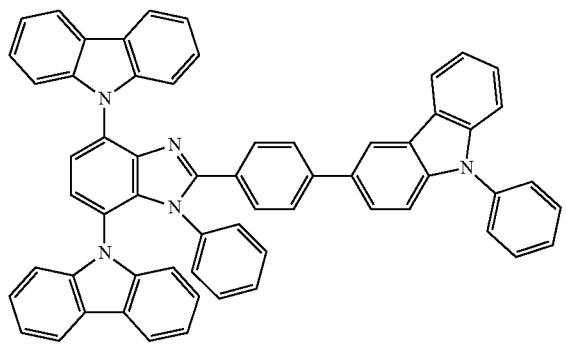
A94
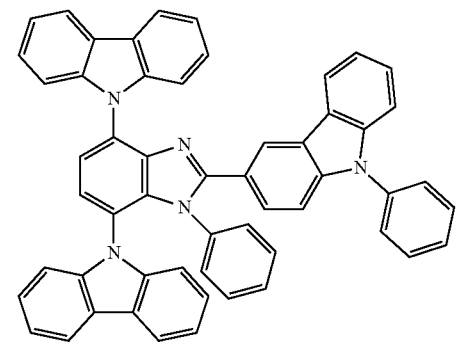

-continued

A95
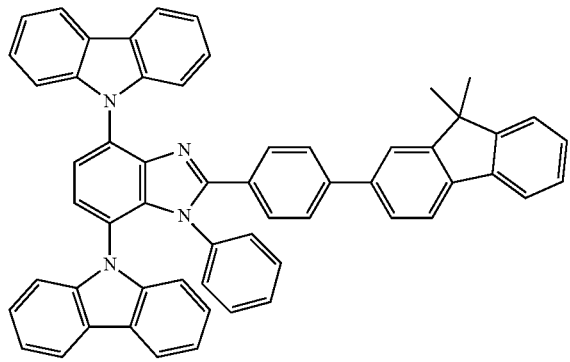

A96
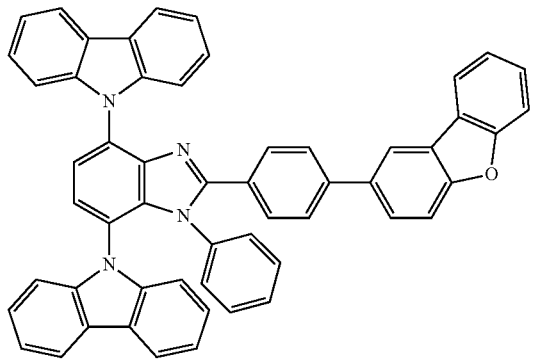

A97
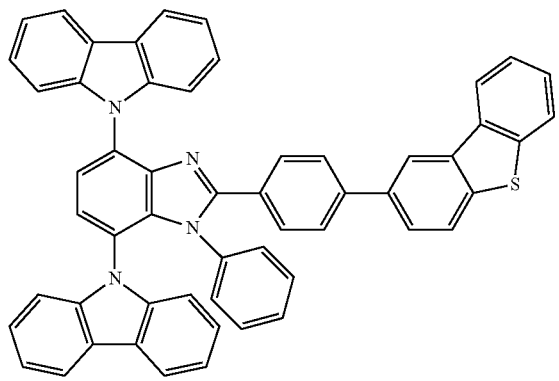

A98
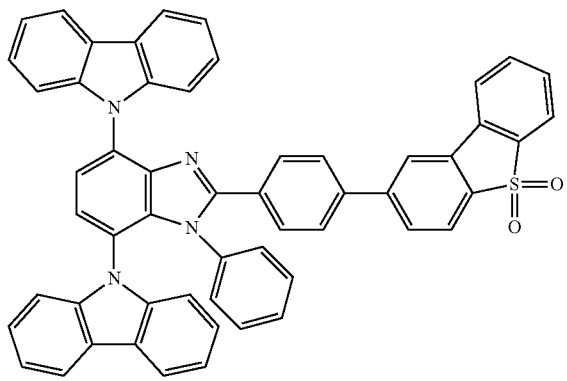

A99
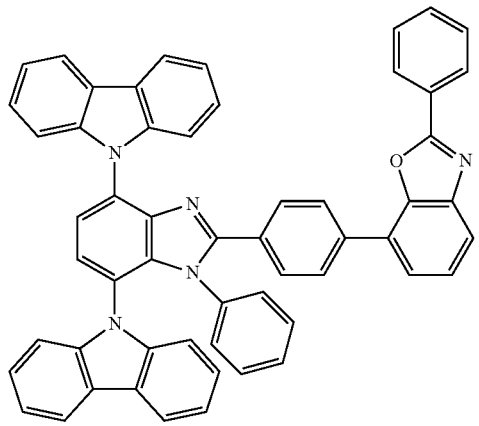

A100
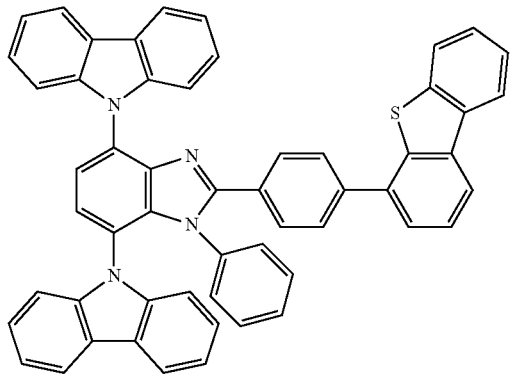

The present invention further provides an electroluminescent OLED device of a material of Formula I;

in particular, said organic electroluminescent device is composed of a transparent substrate, an anode, a hole injection layer, a hole transport layer, an organic light-emitting layer, an electron transport layer and a cathode layer in sequence from the bottom to the top;

wherein the material constituting said transparent substrate is glass or a flexible substrate; and the material constituting said anode layer is an inorganic material or an organic electrically conductive polymer; wherein said inorganic material is indium tin oxide, zinc oxide, tin zinc oxide, gold, silver or copper; and said organic electrically conductive polymer is selected from at least one of a polythiophene, sodium polyvinylbenzene sulphonate and a polyaniline;

the material constituting said hole injection contains one or more of the following compounds, but not limited to the following compounds:

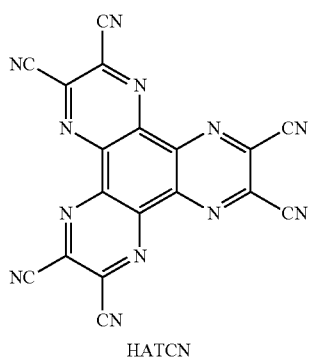

HATCN

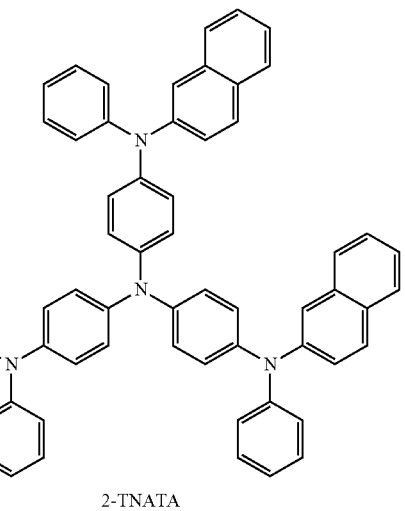

2-TNATA

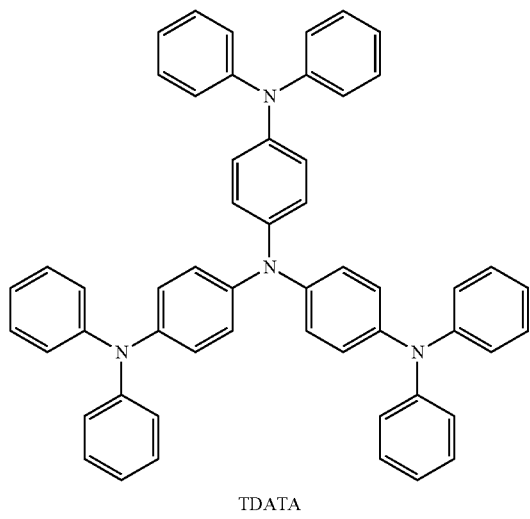

TDATA

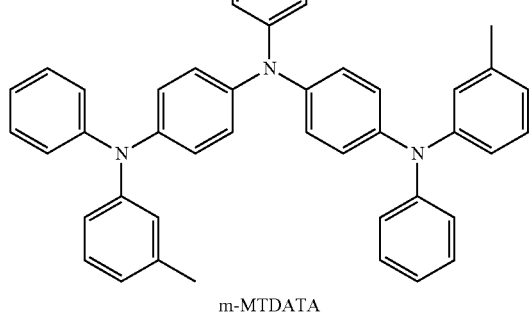

m-MTDATA the material constituting said transport layer contains, but not limited to one or more of the following compounds:

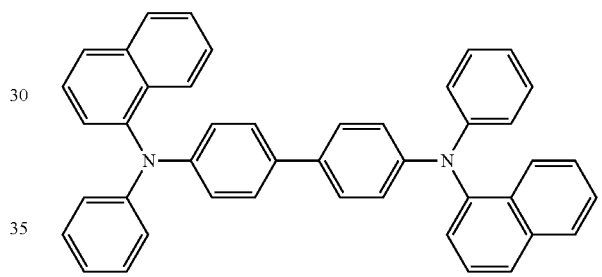

NPB

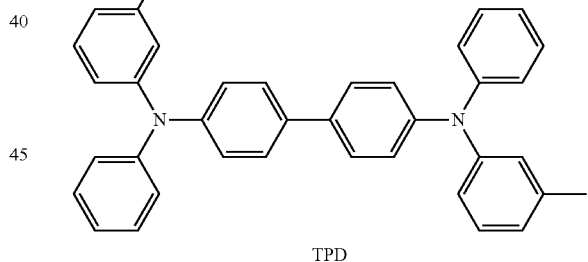

TPD the material constituting said organic light-emitting layer contains a compound of Formula (I) of the present invention and/or one or more of the following compounds, but not limited to the following compounds:

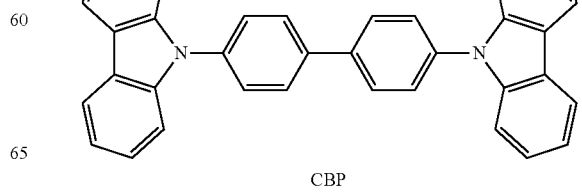

CBP

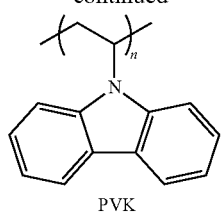
PVK
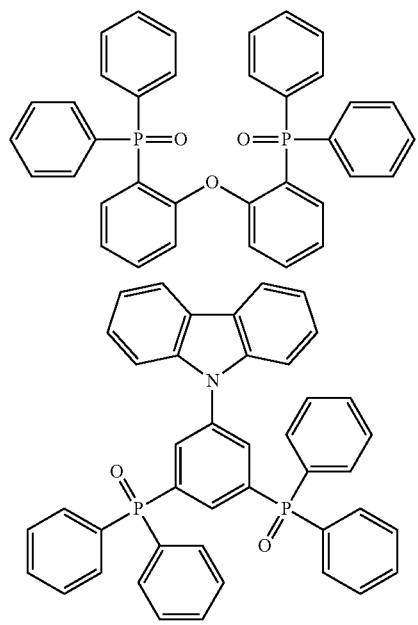
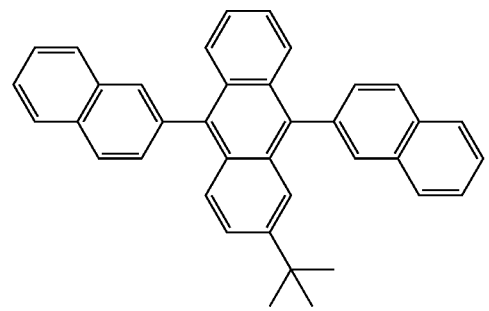
TBADN
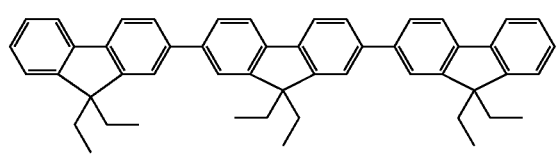
E3
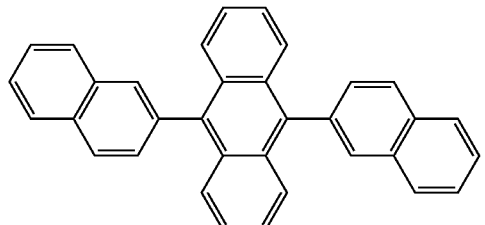
ADN
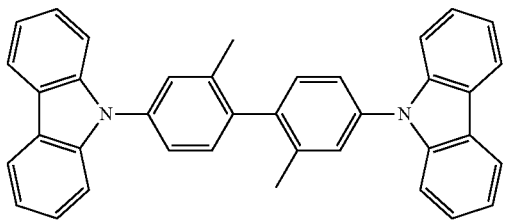
dmCBP
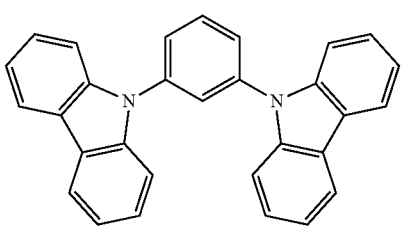
mCP
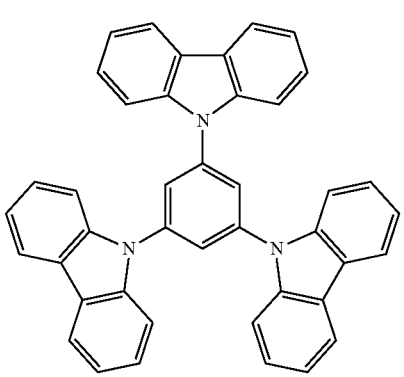
TCzP
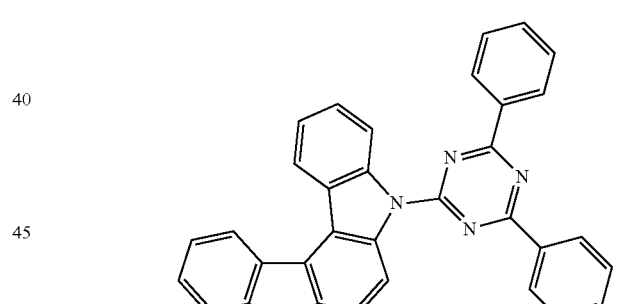
Slic-H117
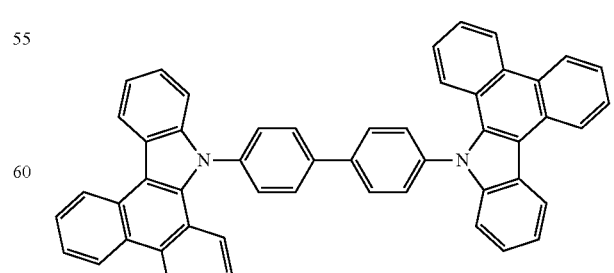
BCPB

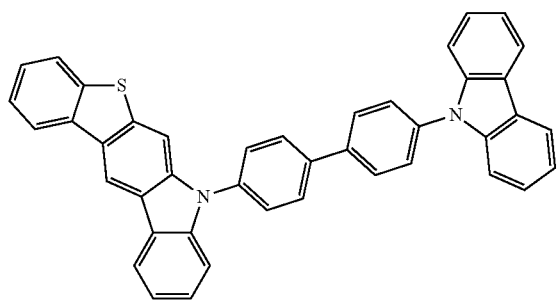

Slic-H065

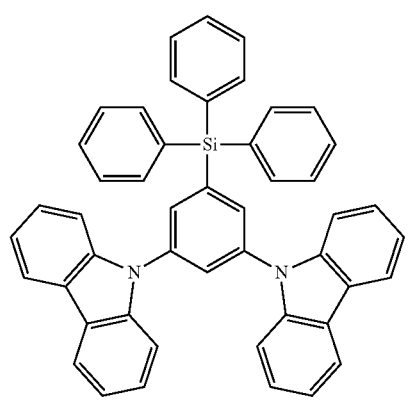

SimCP

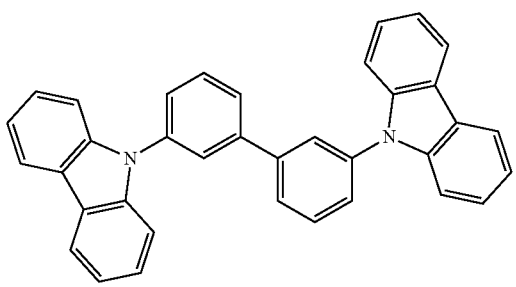

mCBP the material constituting said electron transport layer is a metal complex having the following structure, but is not limited to the following materials:

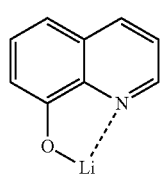

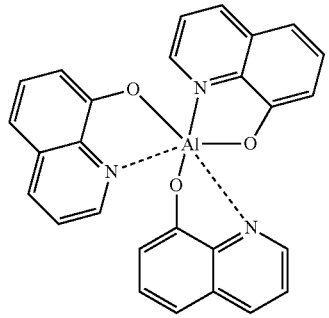

Alq3

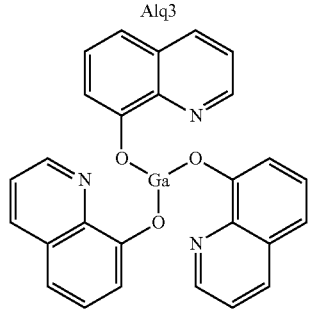

Gaq3

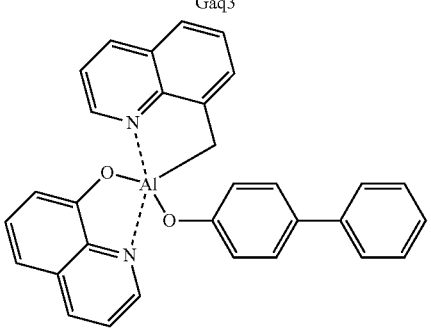

BAlq and the material constituting said cathode layer is selected from any one of or an alloy of any two of or a fluoride of the following elements: lithium, magnesium, silver, calcium, strontium, aluminium, indium, copper, gold and silver.

In the organic electroluminescent device, the thickness of said hole injection layer is 30-50 nm, particularly 30 nm;

the thickness of said hole transport layer is 5-15 nm, particularly 10 nm;

the thickness of said organic light-emitting layer is 10-100 nm, particularly 40 nm;

the thickness of said electron transport layer is 10-30 nm, particularly 50 nm; and the thickness of said cathode layer is 90-110 nm, particularly 60 nm.

The organic electroluminescent material of Formula I provided by the present invention has a high glass transition temperature, high thermal stability and excellent film-forming performance. The material has characteristics, for example, methods for the synthesis and purification of the material are simple and suitable for large-scale production, the energy level, luminous properties, thermal stability, etc., of a product can be adjusted by connecting different groups, and is an ideal choice as a luminescent layer material for organic electroluminescent devices. An OLED device using a material of the present invention mentioned above has a

PARTICULAR EMBODIMENTS

The features and technical contents of the present invention are further described in conjunction with specific examples below, but the invention is not limited to the following examples. Reference can be made to the following detailed description and drawings regarding the present invention; however, the drawings are provided for reference only and are not intended to be limiting of the invention. Said raw materials, unless otherwise specified, are commercially available.

In the following examples, OLED materials and devices and test instruments and methods for performance tests are as follows:

OLED device performance test conditions are as follows:
brightness and chromaticity coordinates: tested using a spectrum scanner PhotoResearch PR-715;
electric current density and turn-on voltage: tested using a digital source meter Keithley 2420; and
power efficiency: tested using NEWPORT 1931-C.

BRIEF DESCRIPTION OF THE DRAWINGS

The technical solutions and other advantageous effects of the present invention will be apparent from the following detailed description of the specific examples of the invention in conjunction with the accompanying drawings.

In the drawings.

PARTICULAR EMBODIMENTS

Figure 1:
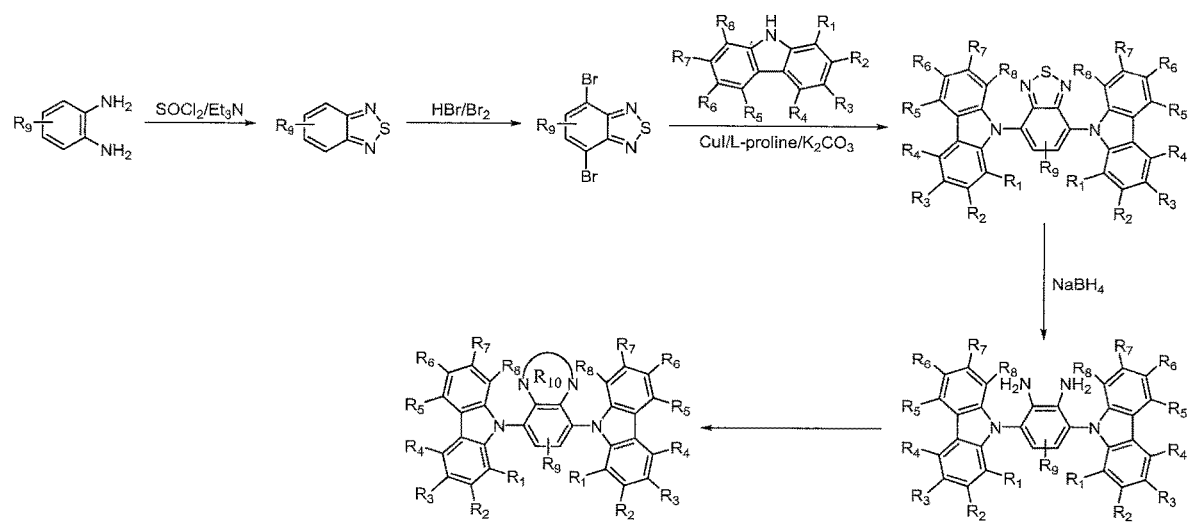
FIG. 1 is a flow chart of a method for preparing a series of carbazole derivatives of the present invention.
Figure 2:
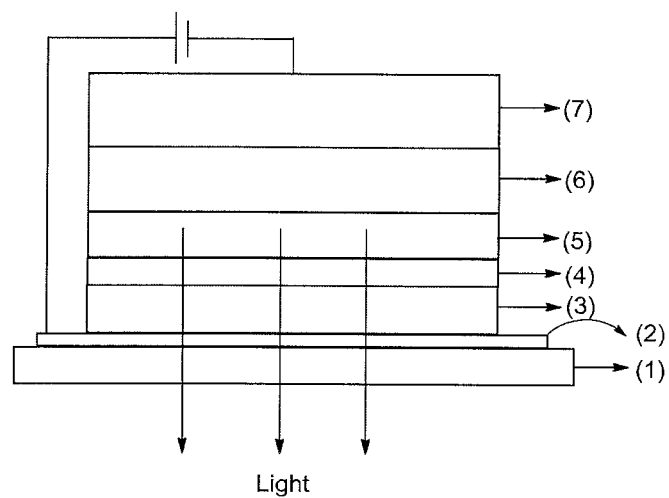
FIG. 2 is a schematic structural diagram of an OLED device structure manufactured by using a compound of Formula (1) of the present invention.
Figure 3:
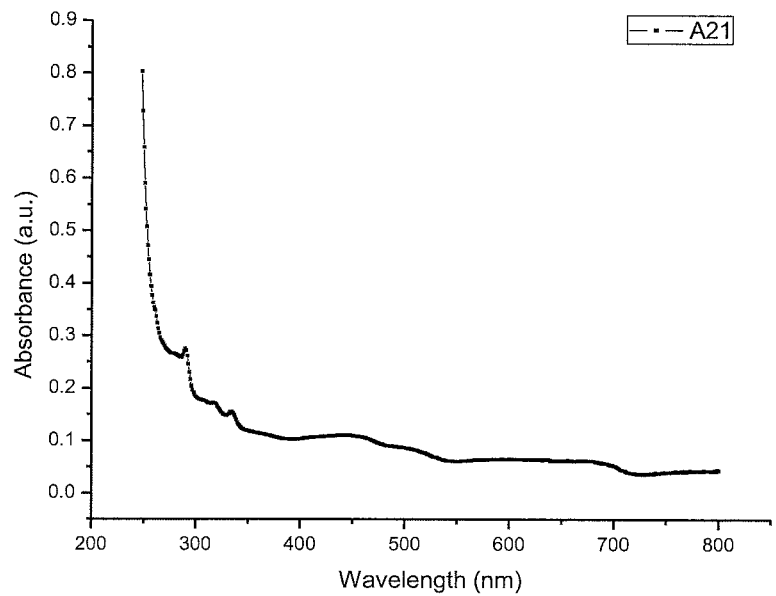
FIG. 3 is an ultraviolet absorption spectrum of a compound of formula (A21) of the present invention.
Figure 4:
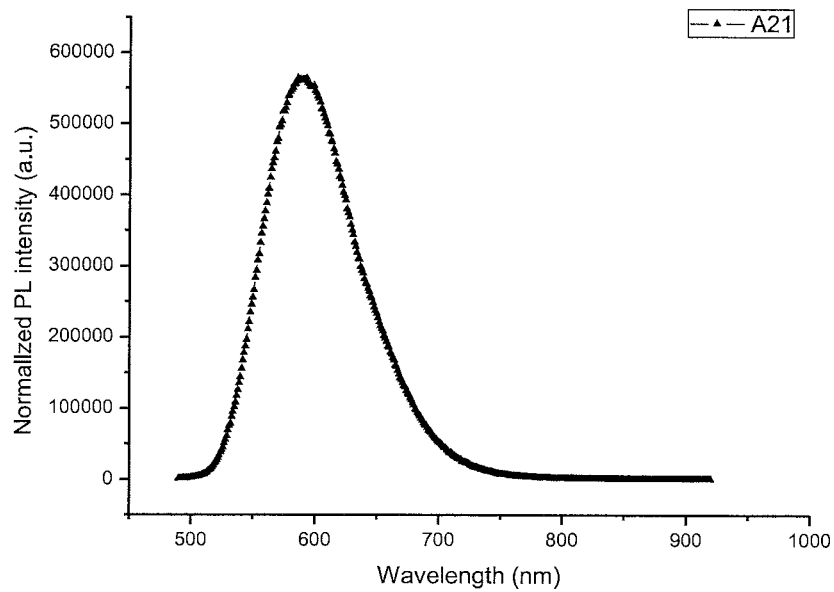
FIG. 4 is a fluorescence spectrum of the compound of formula (A21) of the present invention.
Figure 5:
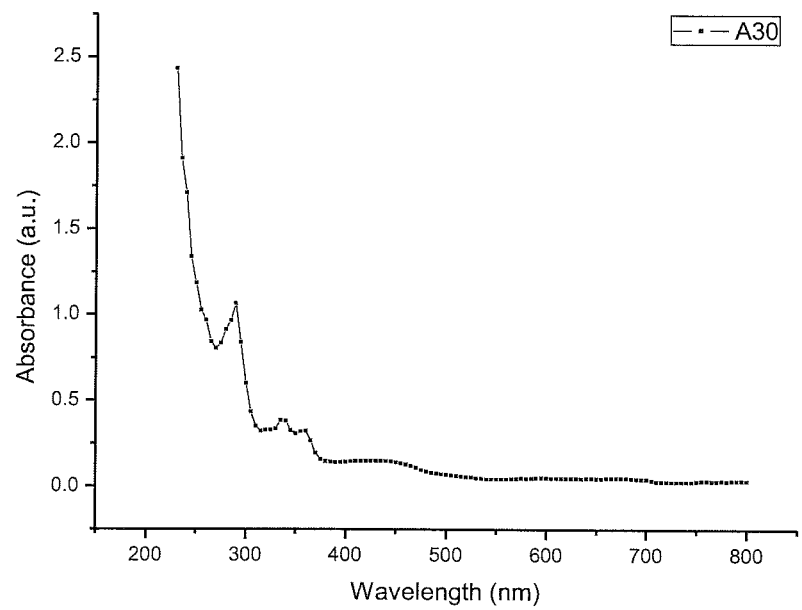
FIG. 5 is an ultraviolet absorption spectrum of a compound of formula (A30) of the present invention.
Figure 6:
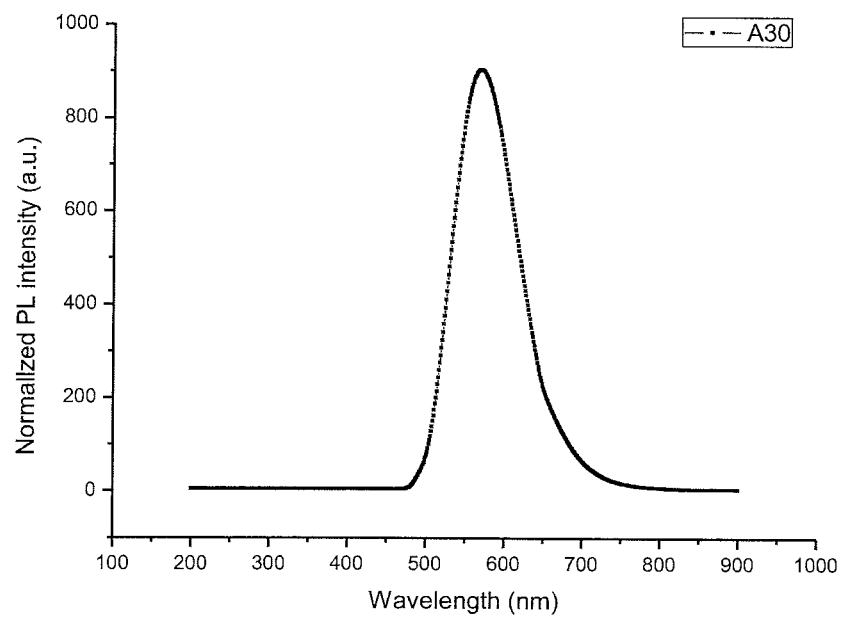
FIG. 6 is a fluorescence spectrum of the compound of formula (A30) of the present invention.

The present invention is further illustrated by the specific examples below, but is not limited to these specific examples.

Example 1: Preparation of Compound A11

Step I: Preparation of Intermediate Benzothiadiazole 10.0 g (92.5 mmol) of o-phenylenediamine is mixed with 300 ml of dichloromethane, 37.4 g (370 mmol) of triethylamine is added and dissolved with stirring, 13.6 ml (184.9 mmol) of thionyl chloride is dropwise added slowly, after being heated to reflux for a reaction for 5 hours, the material is cooled to room temperature and concentrated to dryness under a reduced pressure, 700 ml of water is added, concentrated hydrochloric acid is dropwise added to adjust the pH to acidic, and after filtration, the filter cake is recrystallized with ethanol to give 11 g of a yellow solid, with a yield of 88%.

Step II: Preparation of Intermediate 4,7-Dibromobenzothiadiazole 10 g (73.4 mmol) of the intermediate from the last step is mixed with 100 ml of 48% hydrobromic acid, 35 g (22.3 mmol) of bromine is dropwise added at room temperature, after being heated to reflux for a reaction for 5 hours, the material is cooled to room temperature, 100 ml of a saturated aqueous solution of sodium bisulphite is added, and after filtration, the filter cake is recrystallized with ethanol to give 20.7 g of a yellow solid, with a yield of 96%.

Step III: Preparation of Compound A2

5 g (17.0 mmol) of 4,7-dibromobenzothiadiazole is mixed with 2.8 g (16.8 mmol) of 3-(N,N-diphenyl)aminocarbazole, 324 mg (1.7 mmol) of cuprous iodide and 9.4 g (68 mmol) of potassium carbonate are added, 100 ml of xylene is added, 399 mg (3.4 mmol) of L-proline is added, after being heated to reflux with stirring for a reaction for 12 hours, the material is cooled to room temperature and filtered, the filter cake is washed with toluene, the filtrate is concentrated to dryness under a reduced pressure, 100 ml of anhydrous ethanol is added, and the material is heated to boiling and filtered immediately when hot to give 8.4 g of a yellow solid, with a yield of 62%. MS (MALDI-TOF): m/z 801.273 $[M+1]^+$. $^1$H-NMR ($\delta$, CDCl$_3$): 7.055-7.358 (28H, m), 7.563-7.584 (2H, m), 7.624-7.638 (2H, m), 7.644-7.662 (2H, m), 8.324-8.341 (2H, m).

Step IV: Preparation of Intermediate 3,6-bis(3-diphenylamino)carbazole)benzene-1,2-diamine 5 g (6.2 mmol) of a compound A2 is mixed with 725 mg (18.7 mmol) of sodium borohydride, 100 ml of tetrahydrofuran and 10 ml of water are added, after being heated to reflux with stirring for a reaction for 12 hours, the material is cooled to room temperature and concentrated to dryness under a reduced pressure, 100 ml of water is added, and the material is filtered to give 4.6 g of a yellow solid, with a yield of 95%.

Step V: Preparation of Compound A11

4 g (5.1 mmol) of the diamine intermediate prepared above is mixed with 750 mg (5.1 mmol) of a 40% an aqueous solution of glyoxal, 50 ml of tetrahydrofuran is added, after heating to reflux with stirring, 0.1 ml of concentrated hydrochloric acid is added, after a reflux reaction for 4 hours, the material is cooled to room temperature and concentrated to dryness under a reduced pressure, 50 ml of water is added, and the material is filtered to give 2.8 g of a yellow solid, with a yield of 68%. MS (MALDI-TOF): m/z 794.323 $[M]^+$. $^1$H-NMR ($\delta$, CDCl$_3$): 7.054-7.353 (28H, m), 7.561-7.582 (2H, m), 7.623-7.637 (2H, m), 7.643-7.661 (2H, m), 8.322-8.339 (2H, m), 8.852 (2H, s).

Example 2: Preparation of Compound A21

Step I: Preparation of Compound A3

The synthesis operation is carried out with reference to Step III in Example 1, with 3-(N,N-diphenyl)aminocarbazole in Step III in Example 1 replaced with 3-carbazolylcarbazole, to give a yellow solid, with a yield of 55%. MS (MALDI-TOF): m/z 797.244 $[M+1]^+$. $^1$H-NMR ($\delta$, CDCl$_3$): 7.153-7.448 (16H, m), 7.562-7.585 (4H, m), 7.664-7.692 (6H, m), 7.847-7.865 (2H, m), 8.124-8.146 (4H, m).

Step II: Intermediate 3,6-bis(9H-[3,9'-dicarbazole]-9-yl)benzene-1,2-diamine

The synthesis operation is carried out with reference to Step IV in Example 1, with A2 in Step IV in Example 1 replaced with A3, to give a yellow solid, with a yield of 95%.

Step III: Preparation of Compound A21

5 g (6.5 mmol) of the diamine intermediate prepared above is mixed with 1.3 g (6.2 mmol) of phenanthrenequinone, 50 ml of glacial acetic acid is added, after being heated to reflux with stirring for a reaction for 6 hours, the material is cooled to 60° C. and filtered, and the filter cake is washed with acetic acid and then washed with water and ethanol to give 5 g of a yellow solid, with a yield of 81.7%.
MS (MALDI-TOF): m/z 941.322 [M+1]$^+$. $^1$H-NMR ($\delta$, CDCl$_3$): 7.155-7.252 (12H, m), 7.465-7.626 (14H, m), 7.846-7.869 (4H, m), 7.882-7.905 (4H, m), 8.123-8.145 (4H, m), 9.121-9.133 (2H, m).

Example 3: Preparation of Compound of Formula A40

Step I: Preparation of Intermediate 1-(4-(1-phenyl-1H-benzo[d]imidazol-2-yl)phenyl)indole-2,3-dione 10 g (0.068 mol) of isatin is mixed with 100 ml of N,N-dimethylformamide, 18.8 g (0.136 mol) of potassium carbonate and 1.3 g (6.8 mmol) of cuprous iodide are added, 2 g (17 mmol) of L-proline and 29.6 g (0.075 mol) of 2-(4-iodophenyl)-1-phenyl-1H-benzo[d]imidazole are further added, under the protection of nitrogen, the material is heated to 150° C. with stirring and reacted for 12 hours, cooled to room temperature and filtered, the filtrate is poured into 500 ml of ice water and filtered, and the filter cake is washed with water and then with ethanol to give 16 g of a brown solid, with a yield of 58%.

Step II: Preparation of Compound A40

10.5 g (24 mmol) of 3,6-dicarbazolyl-1,2-diaminobenzene intermediate is mixed with 10 g (24 mmol) of the intermediate from the last step, 150 ml of acetic acid is added, after being heated to reflux with stirring for a reaction for 8 hours, the material is cooled to room temperature and filtered, and the filter cake is washed with water and then ethanol to give 11 g of a yellow solid, with a yield of 56%. MS (MALDI-TOF): m/z 818.294 [M+1]$^+$. $^1$H-NMR ($\delta$, CDCl$_3$): 7.253-7.528 (21H, m), 7.535-7.641 (8H, m), 7.816-7.824 (2H, m), 8.246-8.259 (3H, m), 8.646~7.655 (1H, m).

Example 4: Preparation of Compound A52

10 g (22.8 mmol) of a 3,6-dicarbazolyl-1,2-diaminobenzene intermediate is mixed with 2.3 g (7.6 mmol) of hexaketocyclohexane octahydrate, 200 ml of acetic acid is added, 0.5 g of p-toluenesulphonic acid is added, after being heated to reflux with stirring for a reaction for 12 hours, the material is cooled to room temperature and filtered, and the filter cake is washed with water and then ethanol to give 8.3 g of a brown solid, with a yield of 82%. MS (MALDI-TOF): m/z 1374.460 [M]$^+$. $^1$H-NMR ($\delta$, DMSO-d$_6$): 7.155-7.468 (36H, m), 7.822-7.840 (6H, m), 7.865-7.884 (6H, m), 8.122-8.139 (6H, m).

Example 5: Preparation of Compound A77

Step I: Preparation of Intermediate 4,4'-dicarbazolylbenzil 4 g (10.8 mmol) of 4,4'-dibromobenzil is dispersed in 80 ml of nitrobenzene, 4 g (24 mmol) of carbazole, 419 mg (2.2 mmol) of cuprous iodide, 4.5 g (32 mmol) of potassium carbonate and 1.1 g of 18-crown-6 are added, under the protection of nitrogen, the material is heated to reflux and reacted for 8 hours, cooled to room temperature and filtered, and the filtrate is concentrated to dryness under a reduced pressure and separated and purified with a silica gel column to give 4.6 g of a yellow solid, with a yield of 78%.

Step II: Preparation of Compound A72

3.5 g (7.4 mmol) of a 3,6-dicarbazolyl-1,2-diaminobenzene intermediate is mixed with 4 g (7.4 mmol) of the intermediate from the last step, 80 ml of glacial acetic acid is added, after being heated to reflux with stirring for a reaction for 12 hours, the material is cooled to room temperature and filtered, and the filter cake is washed with water and then ethanol to give 6.4 g of a yellow solid, with a yield of 92%. MS (MALDI-TOF): m/z 943.352 [M+1]$^+$. $^1$H-NMR ($\delta$, CDCl$_3$): 7.155-7.293 (12H, m), 7.324-7.396 (10H, m), 7.724-7.792 (12H, m), 7.816-7.827 (4H, m), 8.116-8.131 (4H, m).

Step III: Preparation of Compound A77

6.0 g (6.36 mmol) of a compound A72 is dissolved in 600 ml of anhydrous dichloromethane, under the protection of nitrogen, 10.3 g (63.6 mmol) of anhydrous ferric chloride is added, after a reaction with stirring at room temperature for 6 hours, the material is concentrated to dryness under a reduced pressure, 100 ml of anhydrous methanol is added, and the material is heated to boiling and filtered immediately when hot to give a grey solid, and then separated and purified with a silica gel column to give 3.3 g of a yellow solid, with a yield of 55%. MS (MALDI-TOF): m/z 941.343 [M+1]$^+$. $^1$H-NMR ($\delta$, CDCl$_3$): 7.156-7.294 (12H, m), 7.325-7.397 (10H, m), 7.627-7.642 (6H, m), 7.662-7.679 (6H, m), 7.806-7.810 (4H, m), 8.546 (2H, s).

Example 6: Preparation of Compound A82

Step I: Preparation of Intermediate 4-(4,7-bis(9H-carbazol-9-yl)-1H-benzo[d]imidazol-2-yl)-N,N-diphenylamine 4.4 g (10 mmol) of a 3,6-dicarbazolyl-1,2-diaminobenzene intermediate is mixed with 2.8 g (10 mmol) of 4-dianilinobenzaldehyde, 50 ml of N,N-dimethylformamide is added, the material is heated to 150° C. with stirring and reacted for 8 hours and cooled to room temperature, the reaction solution is poured into ice water and filtered, the filter cake is washed with water and then ethanol to give 6 g of a yellow solid, with a yield of 88%.

Step II: Preparation of Compound A82

5 g (7.2 mmol) of the intermediate from the last step is mixed with 1.77 g (8.6 mmol) of iodobenzene, 80 ml of N,N-dimethylformamide is added, 138 mg (0.72 mmol) of cuprous iodide and 344 mg (8.6 mmol) of sodium hydroxide are further added, the material is heated to reflux with stirring and reacted for 2 hours and cooled to room temperature, the reaction solution is poured into ice water and filtered, the filter cake is washed with water and then ethanol to give 4.8 g of a yellow solid, with a yield of 87%. MS (MALDI-TOF): m/z 768.312 [M+1]$^+$. $^1$H-NMR ($\delta$, CDCl$_3$): 7.032-7.163 (14H, m), 7.206-7.468 (15H, m), 7.736-7.776 (4H, m), 7.884-7.904 (2H, m), 8.279-8.297 (2H, m).

Example 7: Preparation of OLED-1 to OLED-3

1) A glass substrate on which an ITO conductive layer is sputtered is subjected to an ultrasonic treatment in a cleaning agent for 30 minutes, rinsed in deionized water, subjected to a ultrasonic treatment in an acetone/ethanol mixed solvent for 30 minutes, baked in a clean environment to completely dryness and irradiated with an ultraviolet light cleaner for 10 minutes, and the surface is bombarded with low energy cations;

2) the above-treated ITO glass substrate is placed in a vacuum chamber, the vacuum chamber is evacuated to $1\times10^{-5}$ Pa to $9\times10^{-3}$ Pa, and a compound HATCN is evaporated as a hole injection layer onto the above-mentioned anode layer film, with the evaporation rate being 0.1 nm/s and the thickness of the evaporated film being 40 nm;

3) on the above-mentioned hole injection layer, NPB is further evaporated as a hole transport layer, with the evaporation rate being 0.1 nm/s and the thickness of the evaporated film being 10 nm;

4) on the hole transport layer, an organic light-emitting layer of the device with DPEPO as a host material and a compound (of Formula I) of the present invention as a doping material, with DPEPO: the compound of Formula I=90:10 is further evaporated, with the evaporation rate being 0.1 nm/s and the thickness of the evaporated organic light-emitting layer film being 20 nm;

5) on the organic light-emitting layer, a layer of Liq as an electron transport layer of the device is further evaporated, with the evaporation rate being 0.1 nm/s and the thickness of the evaporated film being 40 nm; and 6) on the electron transport layer, a magnesium/silver alloy layer as a cathode layer of the device is evaporated in turn to give an OLED device provided by the present invention, wherein the evaporation rate for the magnesium/silver alloy layer is 2.0-3.0 nm/s, the thickness of the evaporated film is 100 nm, and the mass ratio of magnesium to silver is 1:9.

According to the same procedure as above, as the compound (of Formula I) in Step 4), a compound A21 is selected to give OLED-1 provided by the present invention;

according to the same procedure as above, as the compound (of Formula I) in Step 4), a compound A82 is selected to give OLED-2 provided by the present invention; and according to the same procedure as above, the compound (of Formula I) in Step 4) is replaced with DMAC-DPS to give a comparative device OLED-3;

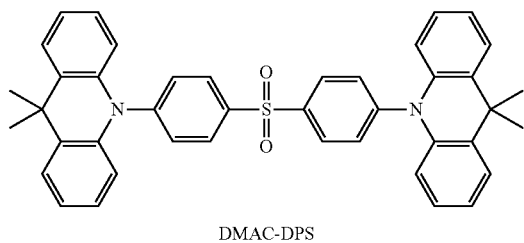

DMAC-DPS and the performance test results of the resulting devices OLED-1 to OLED-3 are as shown in Table 1.

As can be seen from above, the devices prepared by the organic materials of the present patent invention have a low turn-on voltage, under the same brightness conditions, the external quantum efficiencies of the devices are obviously higher than that of the comparative device OLED-3 with DMAC-DPS as the doping material, and the lives of the devices are much longer.

Example 8: Preparation of OLED-4 to OLED-6

1) A glass substrate on which an ITO conductive layer is sputtered is subjected to an ultrasonic treatment in a cleaning agent for 30 minutes, rinsed in deionized water, subjected to a ultrasonic treatment in an acetone/ethanol mixed solvent for 30 minutes, baked in a clean environment to completely dryness and irradiated with an ultraviolet light cleaner for 10 minutes, and the surface is bombarded with low energy cations;

2) the above-treated ITO glass substrate is placed in a vacuum chamber, the vacuum chamber is evacuated to $1\times10^{-5}$ Pa to $9\times10^{-3}$ Pa, and a compound HATCN is evaporated as a hole injection layer onto the above-mentioned anode layer film, with the evaporation rate being 0.1 nm/s and the thickness of the evaporated film being 40 nm;

3) on the above-mentioned hole injection layer, NPB is further evaporated as a hole transport layer, with the evaporation rate being 0.1 nm/s and the thickness of the evaporated film being 10 nm;

4) on the hole transport layer, an organic light-emitting layer of the device with a compound (of Formula I) of the present invention as a host material and Ir(CHPIQ)$_2$acac as a doping material, with the compound of Formula I: Ir(CHPIQ)$_2$acac=90:10 is further evaporated, with the evaporation rate being 0.1 nm/s and the thickness of the evaporated organic light-emitting layer film being 20 nm;

5) on the organic light-emitting layer, a layer of Liq as an electron transport layer of the device is further evaporated, with the evaporation rate being 0.1 nm/s and the thickness of the evaporated film being 40 nm; and 6) on the electron transport layer, a magnesium/silver alloy layer as a cathode layer of the device is evaporated in turn to give an OLED device provided by the present invention, wherein the evaporation rate for the magnesium/silver alloy layer is 2.0-3.0 nm/s, the thickness of the evaporated film is 100 nm, and the mass ratio of magnesium to silver is 1:9.

TABLE 1

Performance test results of the resulting devices OLED-1 to OLED-3

| Device No. | Doping material Compound formula | Turn-on voltage (V) | Electric current density (mA/cm$^2$) | Brightness (Cd/m$^2$) | EQE (%) | CIE (x, y) | T$_{95}$ (hour) |
|---|---|---|---|---|---|---|---|
| OLED-1 | A21 | 3.8 | 3.2 | 1000 | 17.5 | 0.44, 0.50 | 4500 |
| OLED-2 | A82 | 3.6 | 2.8 | 1000 | 18.6 | 0.24, 0.66 | 5000 |
| OLED-3 | DMAC-DPS | 3.8 | 3.5 | 1000 | 17.0 | 0.16, 0.20 | 3000 |

According to the same procedure as above, as the compound (of Formula I) in Step 4), a compound A30 is selected to give OLED-4 provided by the present invention;

according to the same procedure as above, as the compound (of Formula I) in Step 4), a compound A57 is selected to give OLED-5 provided by the present invention; and according to the same procedure as above, the compound (of Formula I) in Step 4) is replaced with PPQ-BCZ to give a comparative device OLED-6;

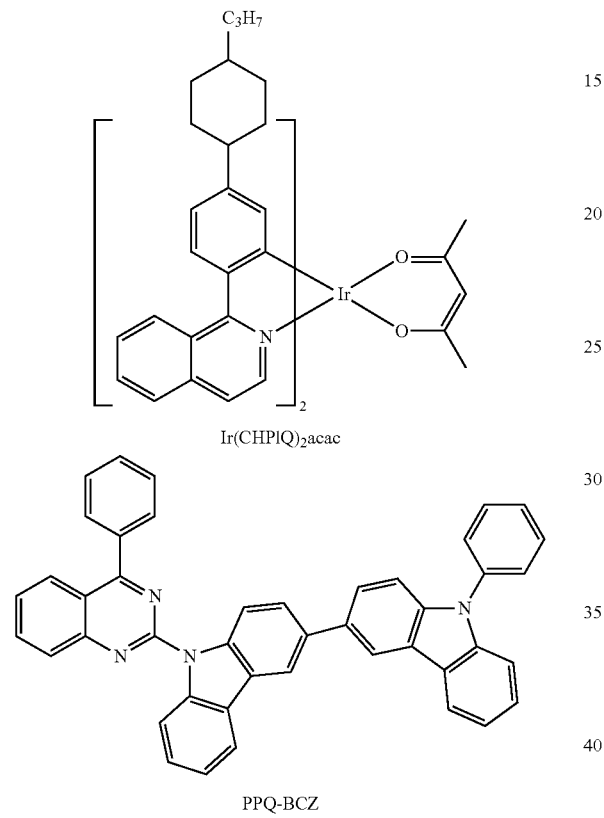

and the performance test results of the resulting devices OLED-4 to OLED-6 are as shown in Table 2.

TABLE 2

Performance test results of the resulting devices OLED-4 to OLED-6

| DEVICES No. | Host material Compound formula | Turn-on voltage (V) | Electric current density (mA/cm$^2$) | Brightness (Cd/m$^2$) | EQE (%) | CIE (x, y) | T$_{95}$ (hour) |
| --- | --- | --- | --- | --- | --- | --- | --- |
| OLED-4 | A30 | 3.8 | 3.6 | 1000 | 21.4 | 0.67, 0.32 | 5000 |
| OLED-5 | A57 | 3.6 | 3.4 | 1000 | 21.6 | 0.67, 0.31 | 6000 |
| OLED-6 | PPQ-BCZ | 4.4 | 3.8 | 1000 | 20.0 | 0.68, 0.32 | 5000 |

As can be seen from above, the devices prepared by the organic materials of the present patent invention have a low turn-on voltage, under the same brightness conditions, the external quantum efficiencies of the devices are obviously higher than that of the comparative device OLED-6 with PPQ-BCZ as the host material, and the lives of the devices are much longer.

Although the present invention has been described in conjunction with the preferred examples, the present invention is not limited to the above-described examples and drawings; and it is to be understood that under the guidance of the inventive concept, various modifications and improvements can be made by a person skilled in the art, and that the scope of the invention is embraced in the appended claims summarize.

The invention claimed is:
1. A compound selected from the group consisting of the following compounds:

A1
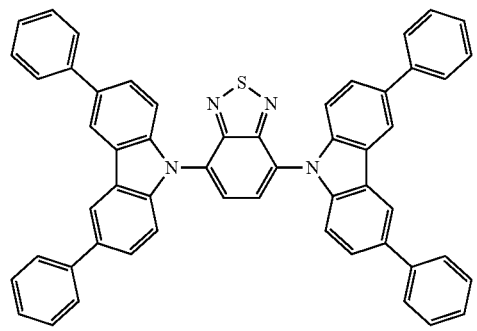

A3
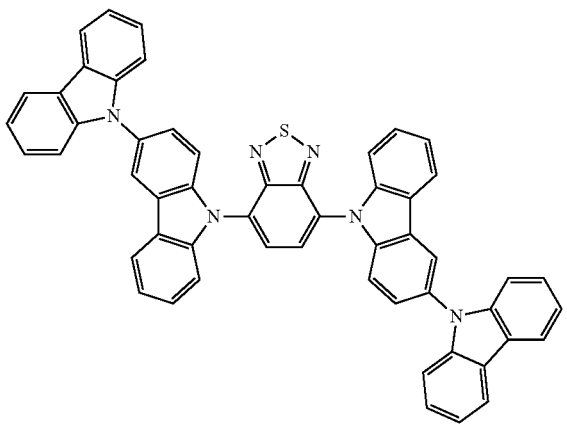

A5
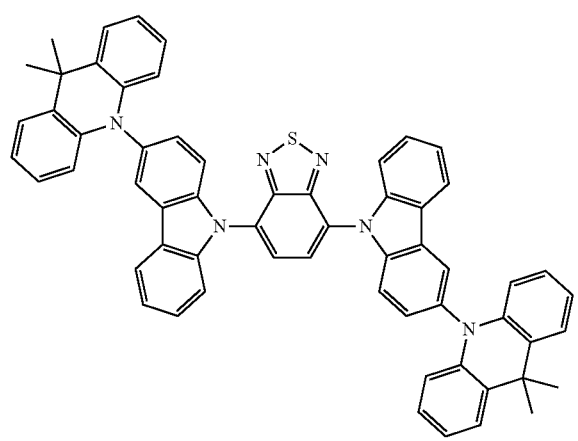

A6
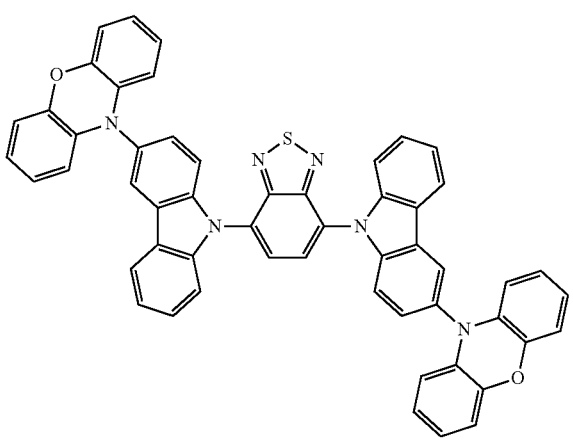

A7
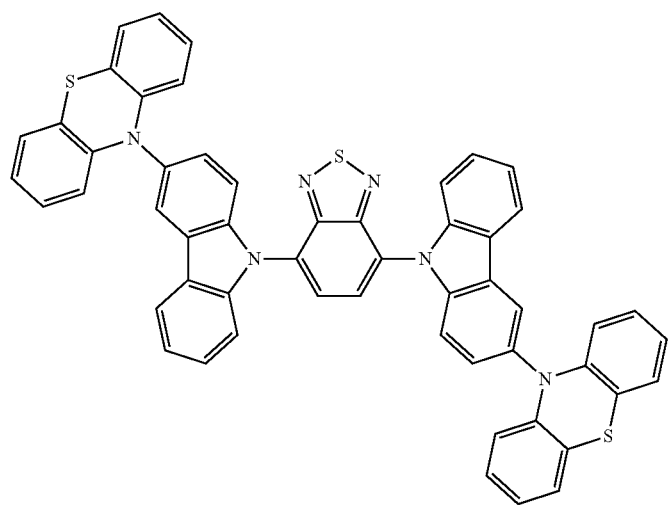

-continued
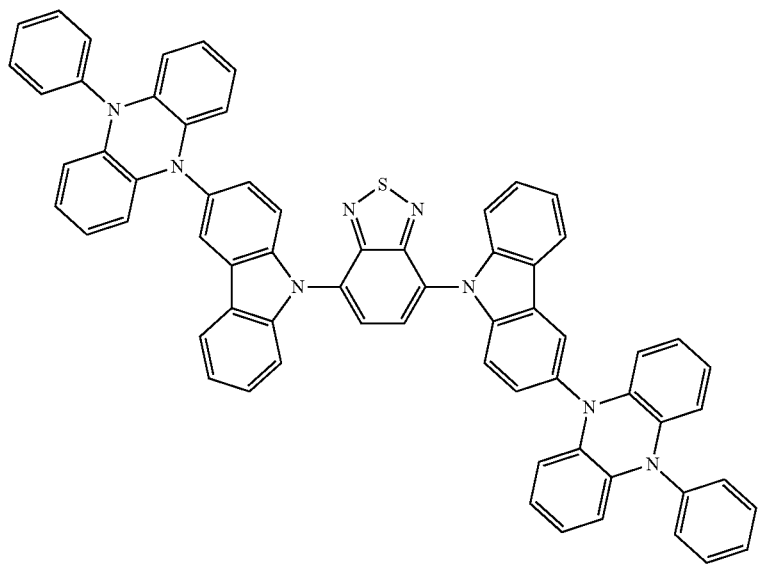
A8
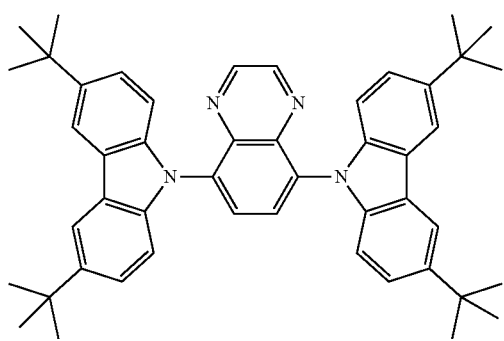
A9
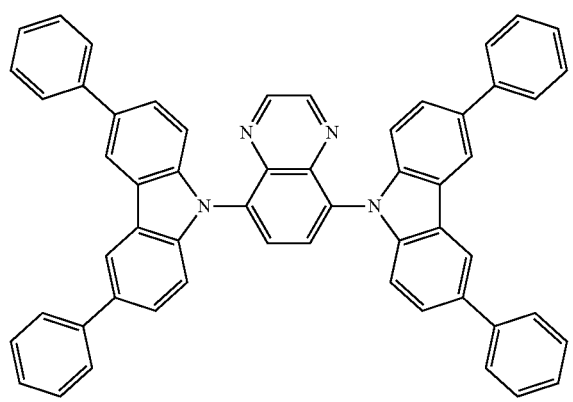
A10
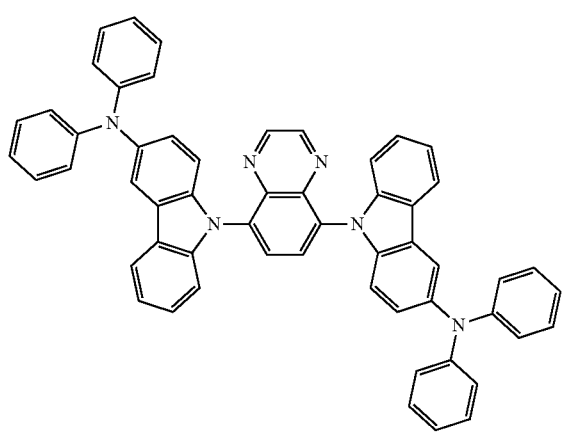
A11
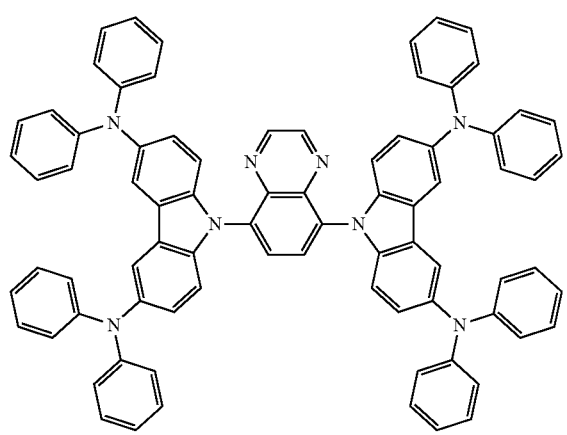
A12

-continued
A13
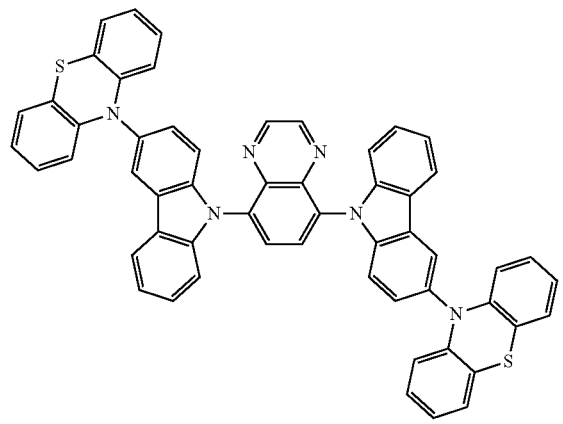
A14
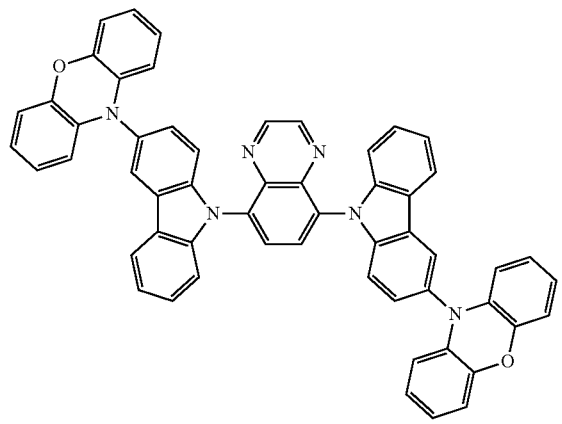
A15
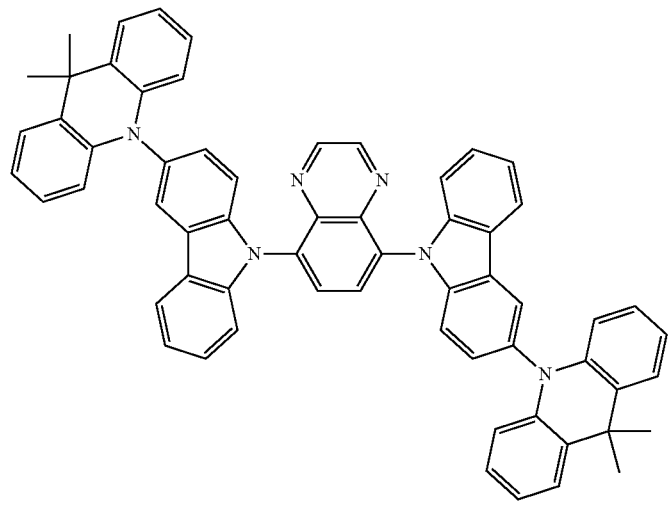
A16
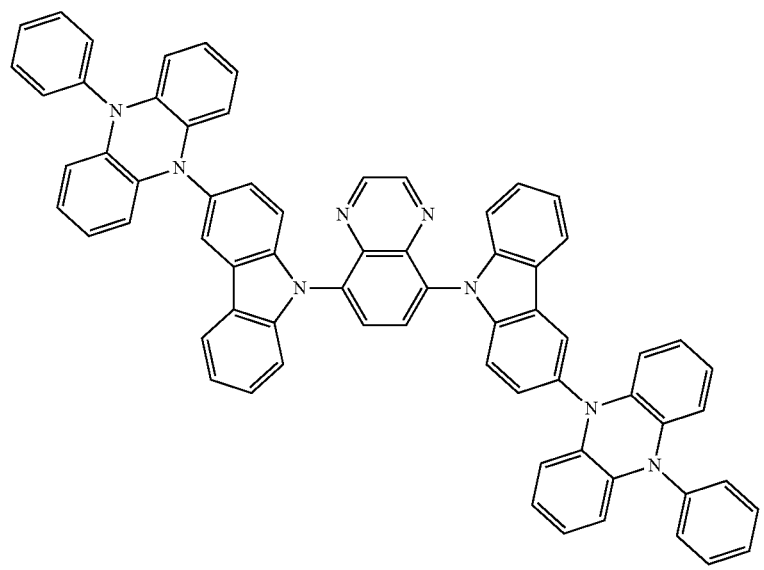

-continued
A17
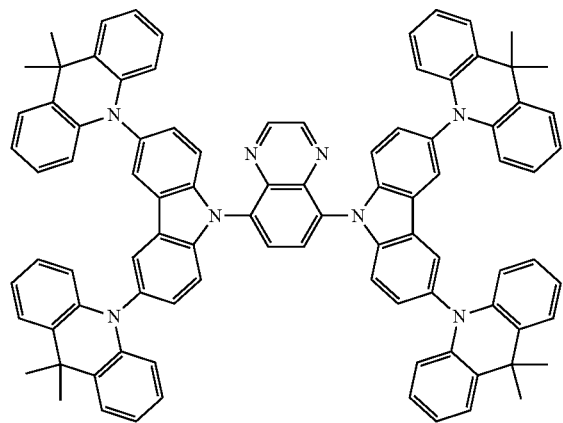
A18
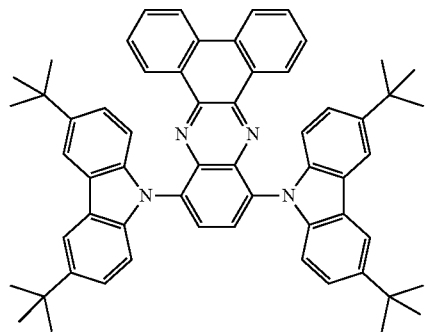
A19
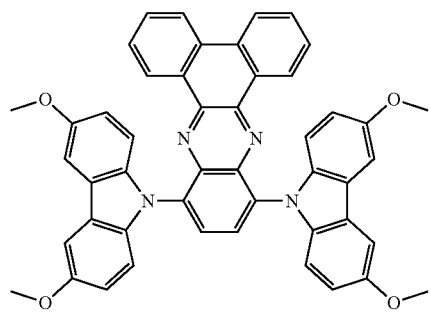
A20
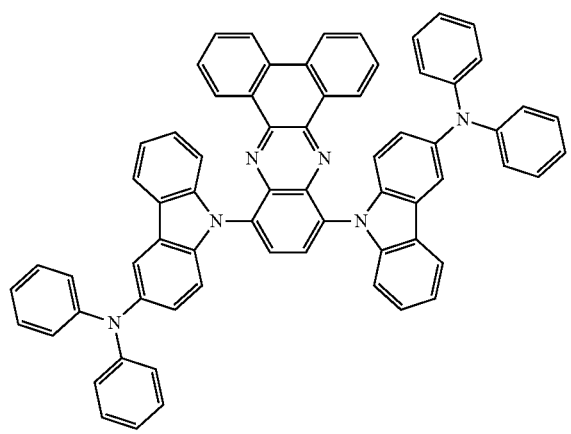
A21
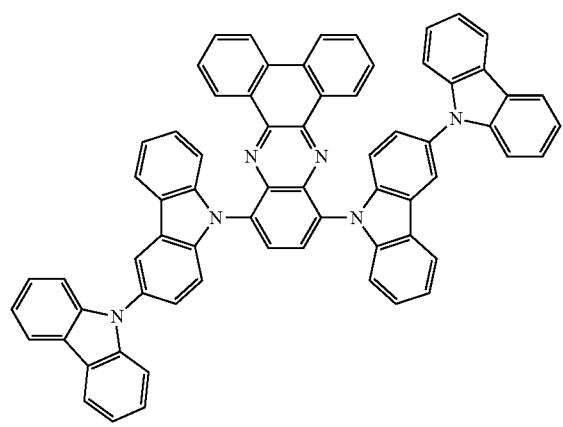
A22
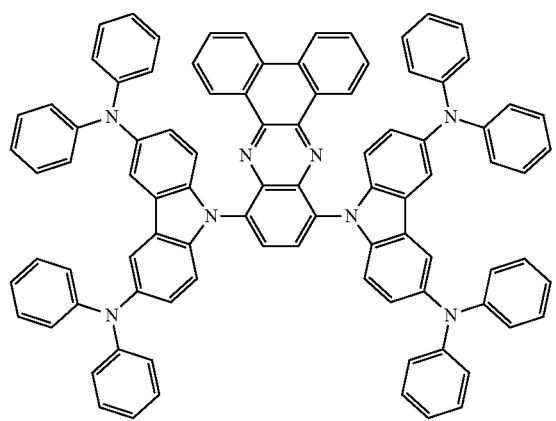

-continued
A23
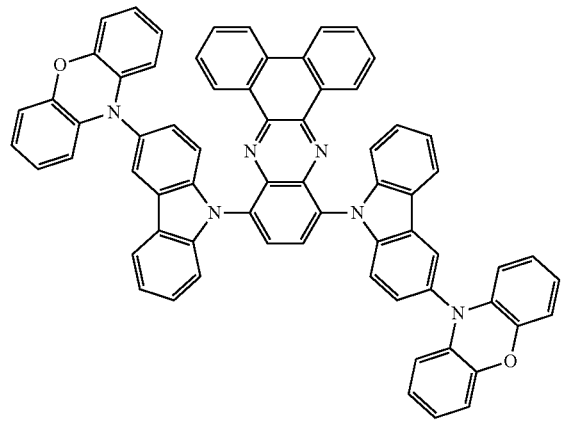
A24
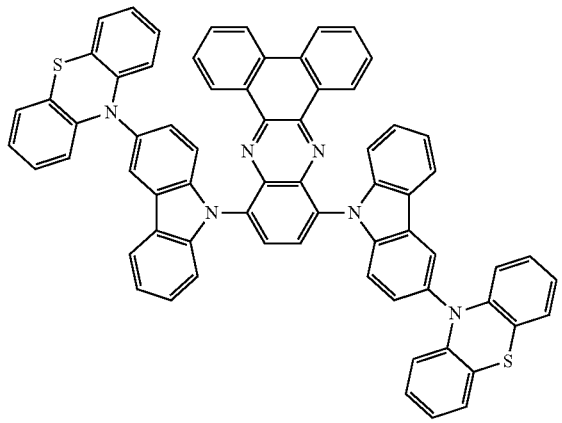
A25
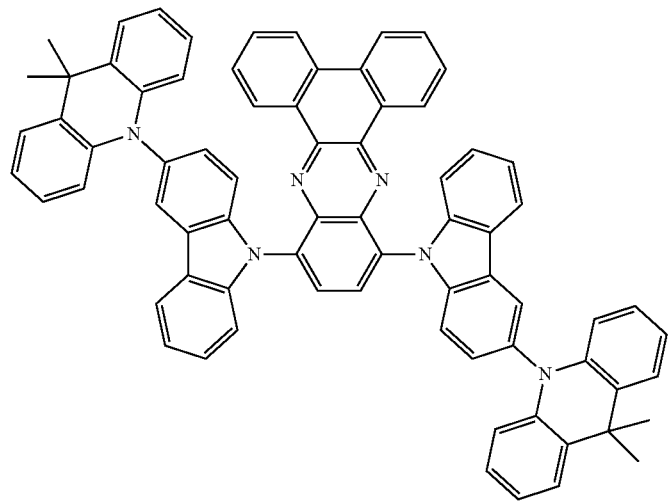
A26
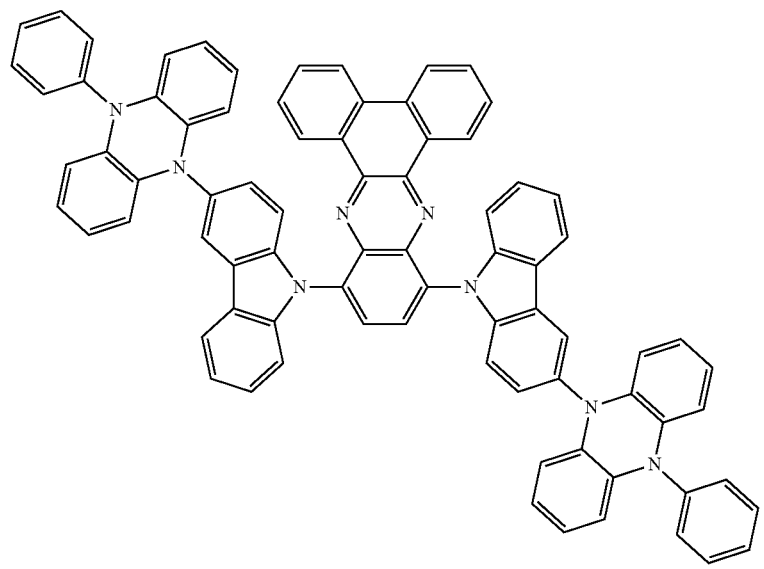

-continued
A27
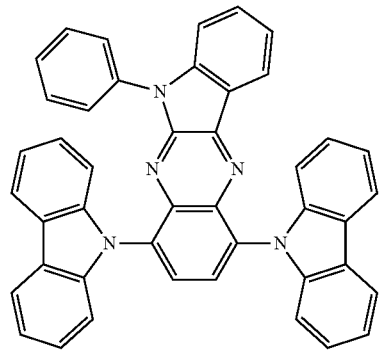
A28
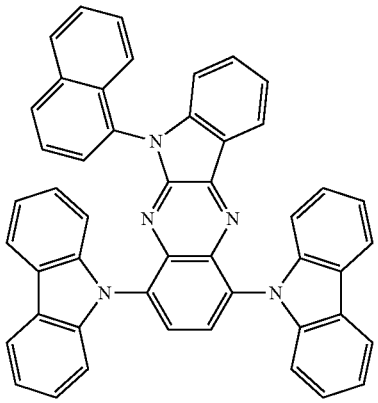
A29
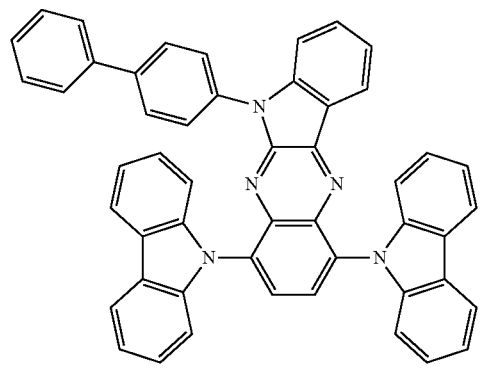
A30
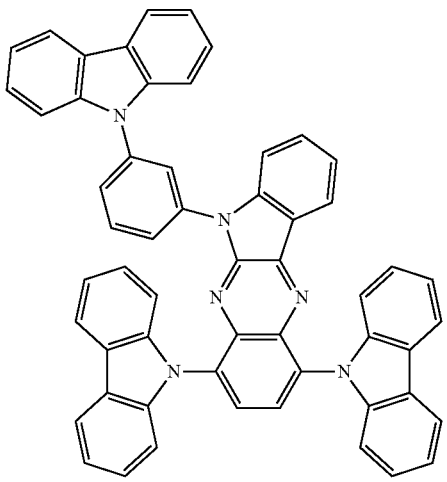
A31
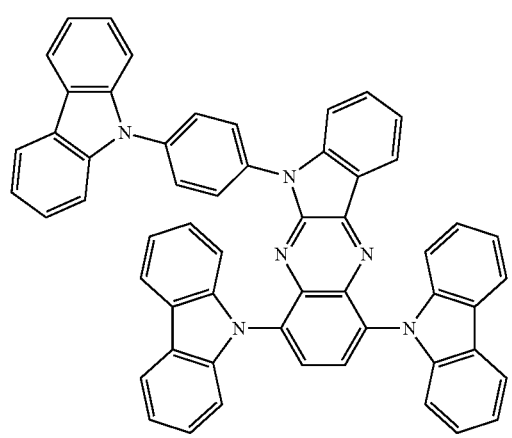
A32
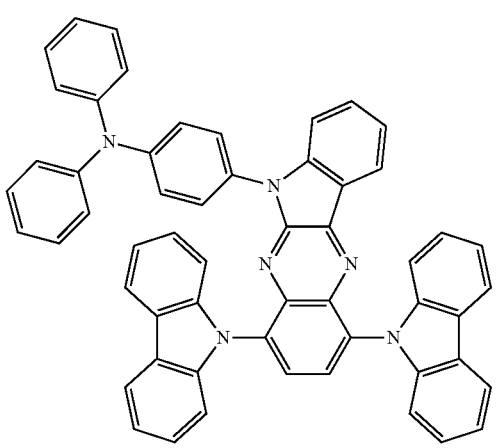

-continued
A33
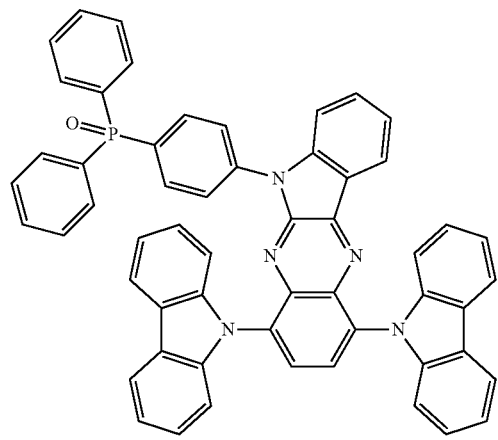
A34
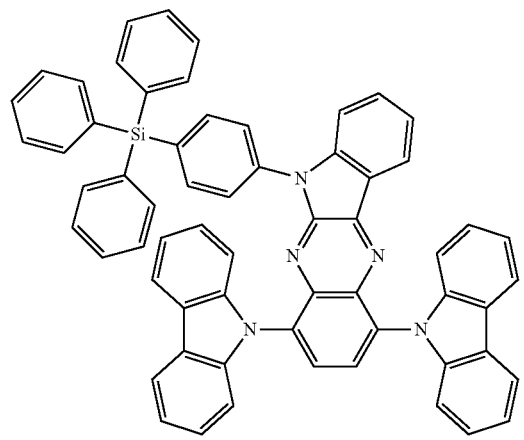
A35
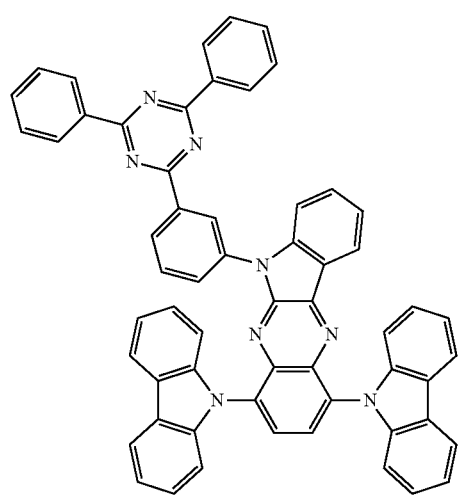
A36
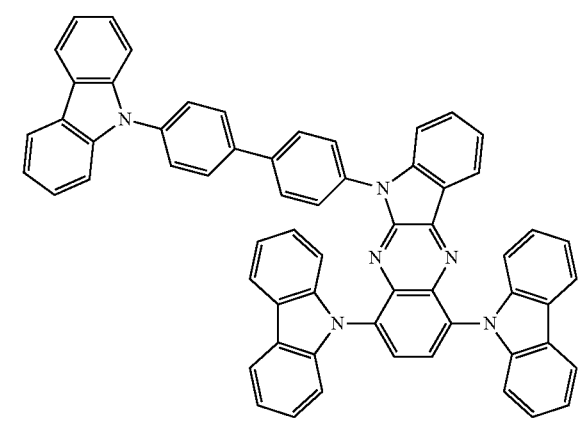
A37
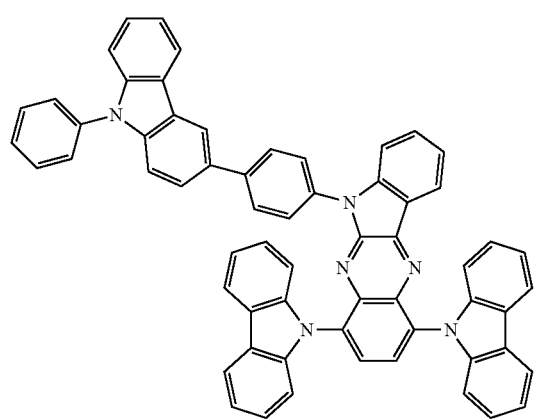
A38
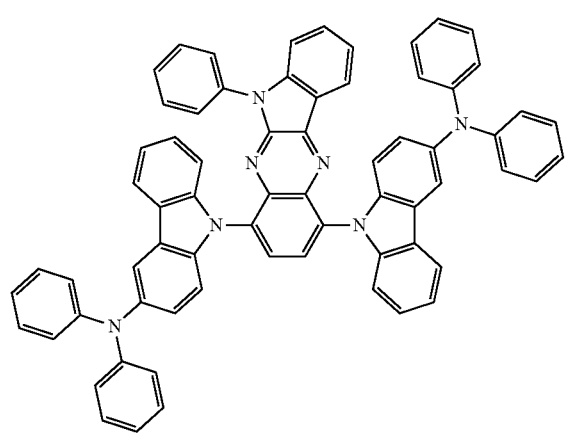

-continued
A39
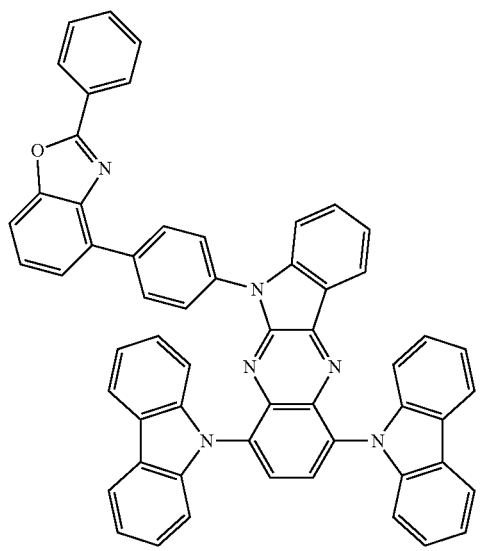
A40
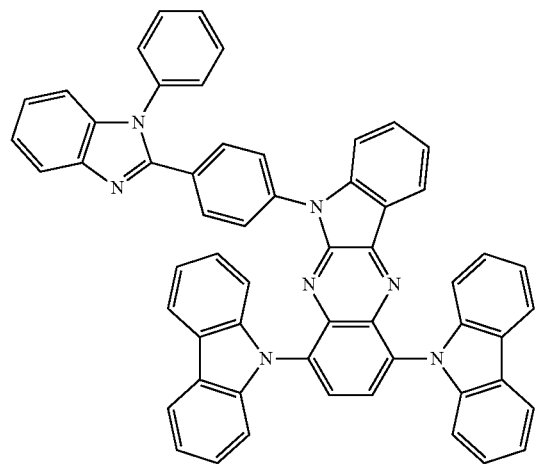
A41
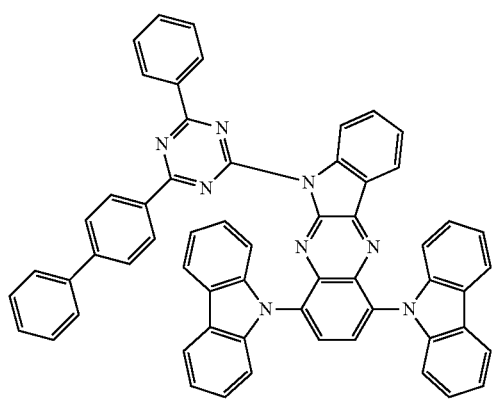
A42
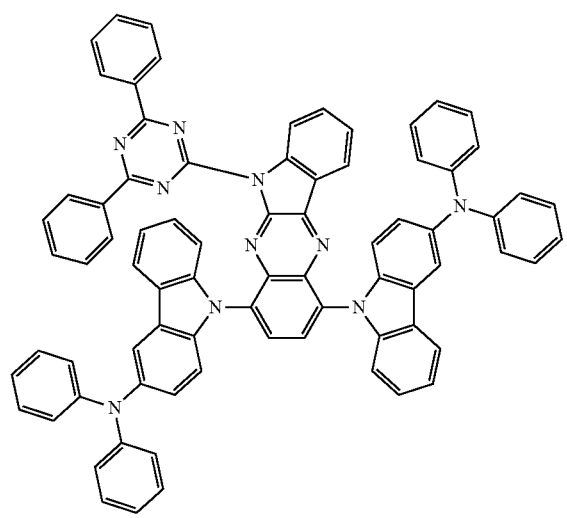
A43
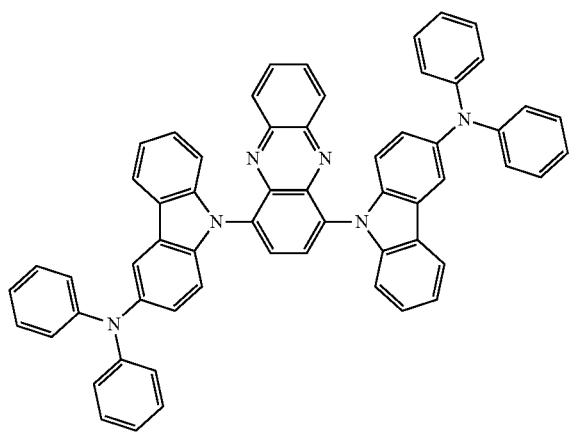
A44
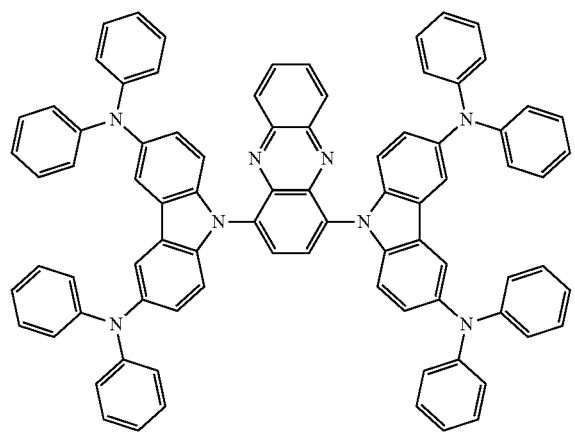

-continued
A45
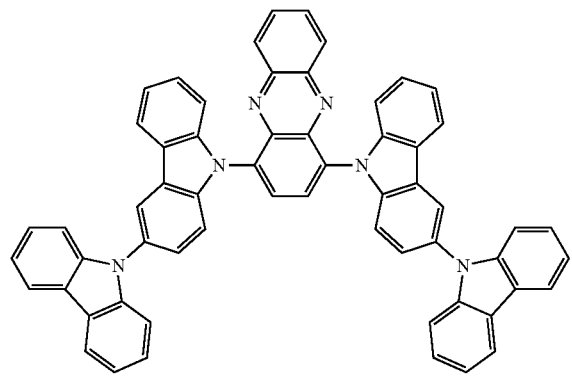
A46
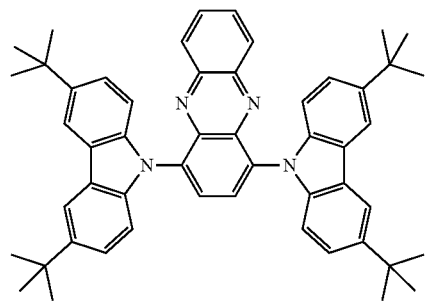
A47
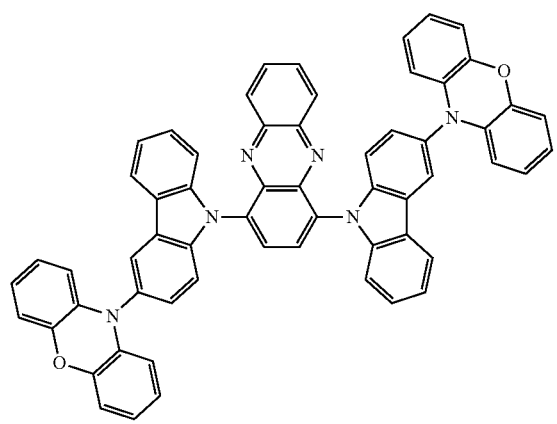
A48
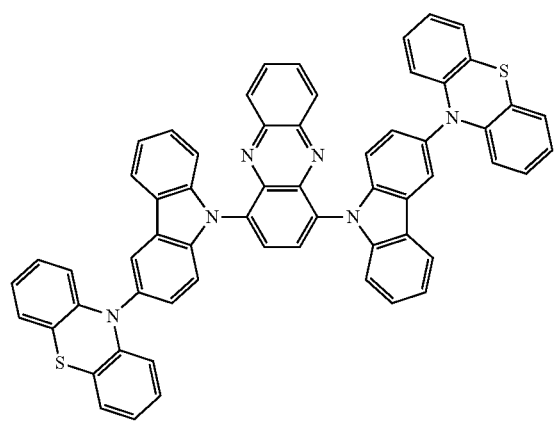
A49
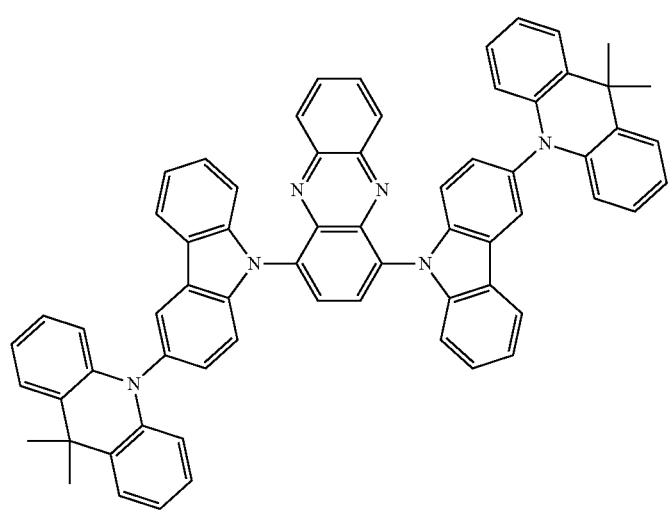

A50
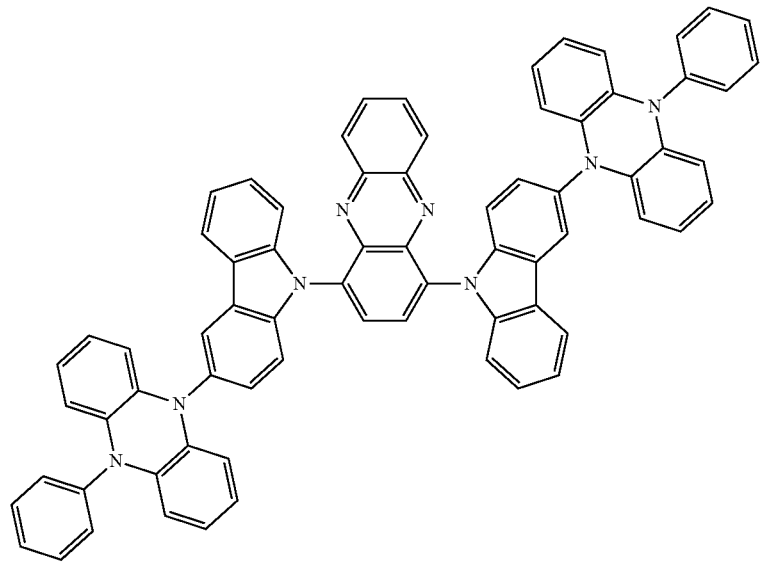
A51
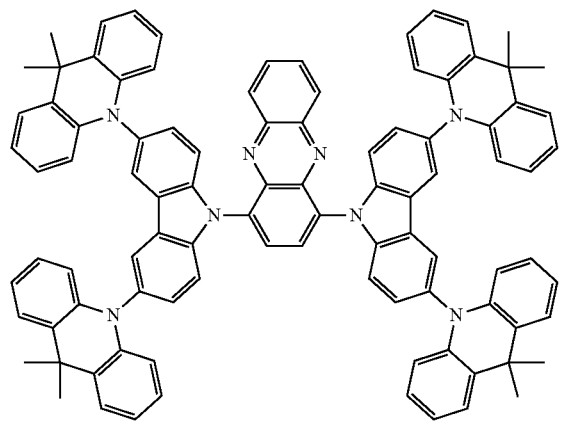
A52
A53 A54
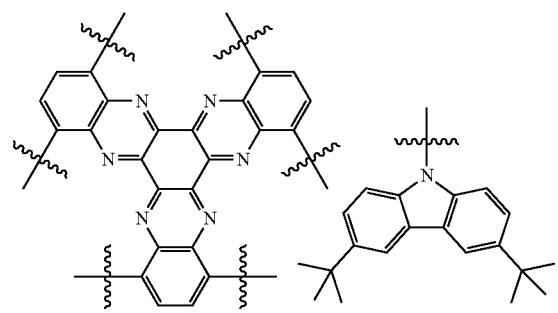
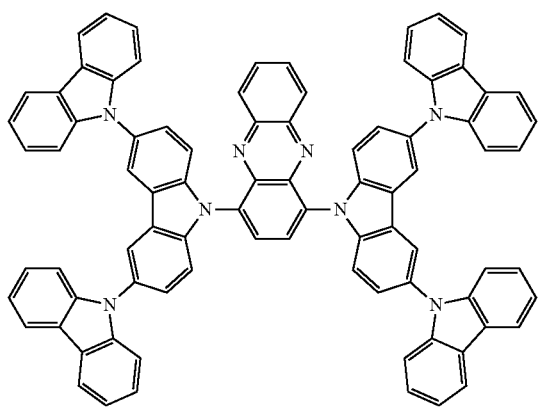

-continued
A55
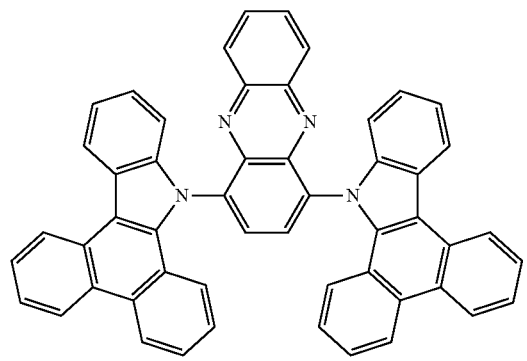
A58
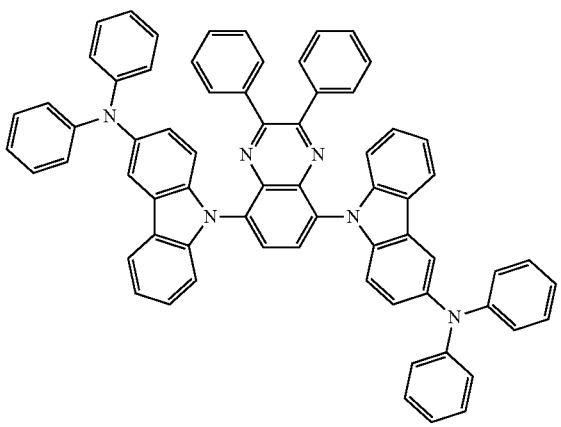
A59
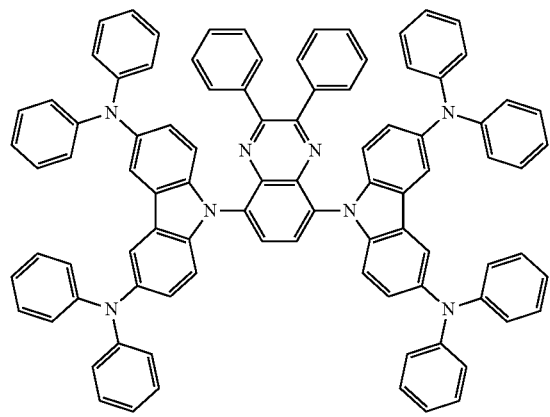
A60
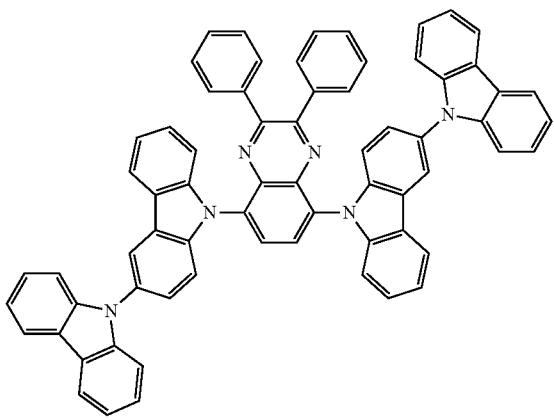
A61
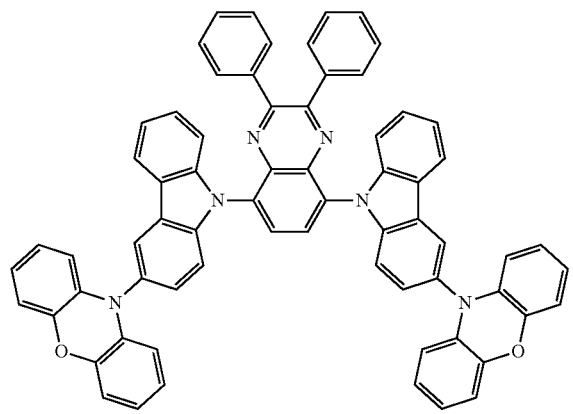
A62
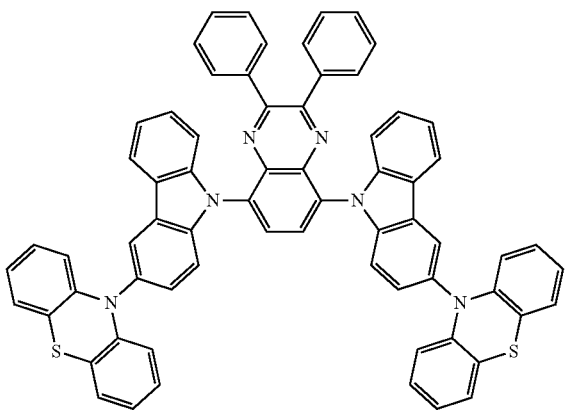

-continued
A63
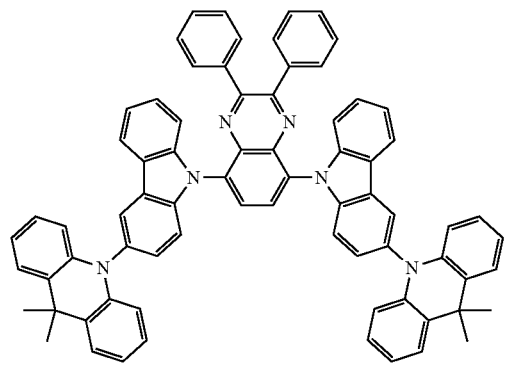
A64
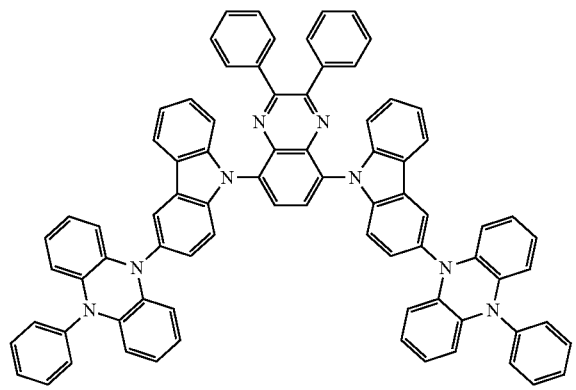
A65
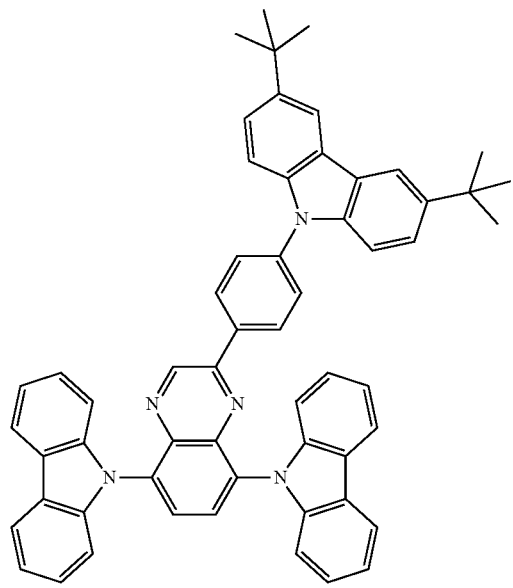
A66
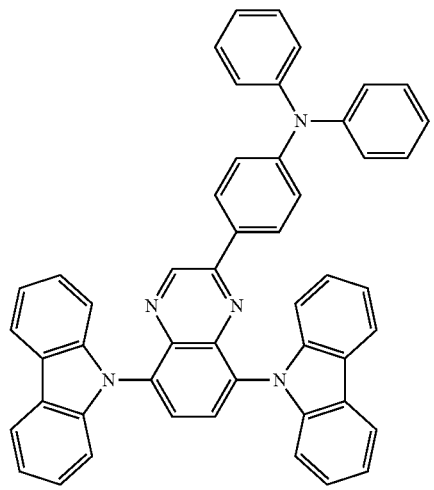
A67
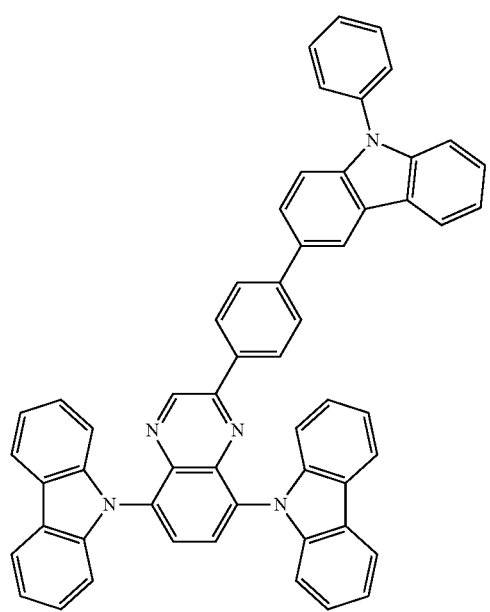
A68
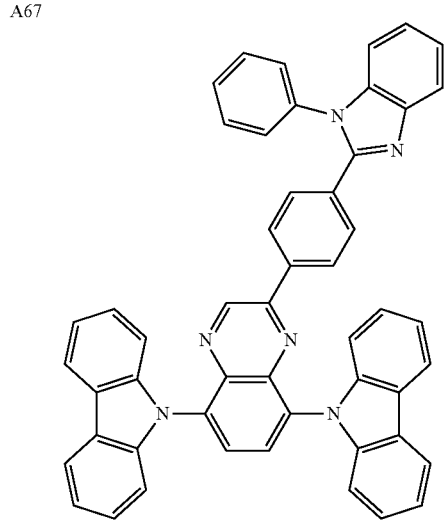

-continued
A69
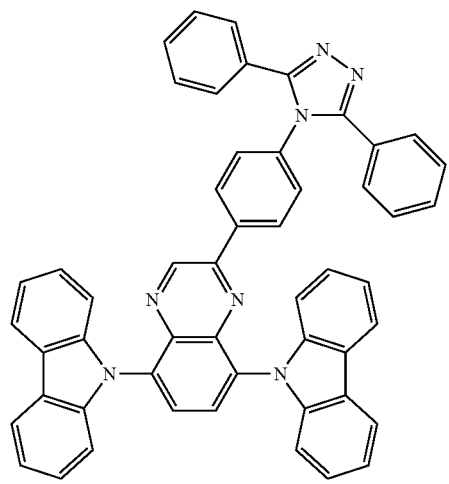
A70
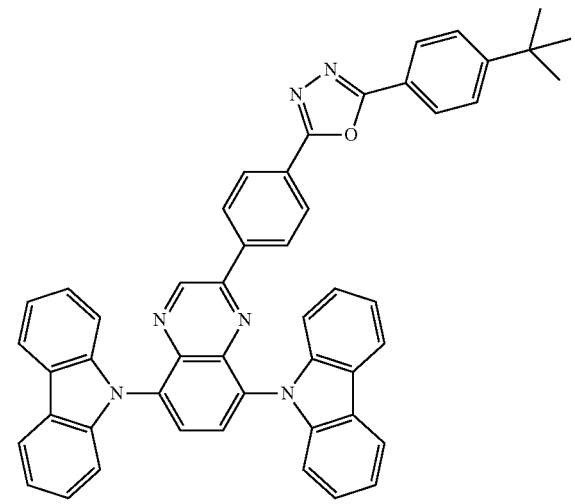
A71
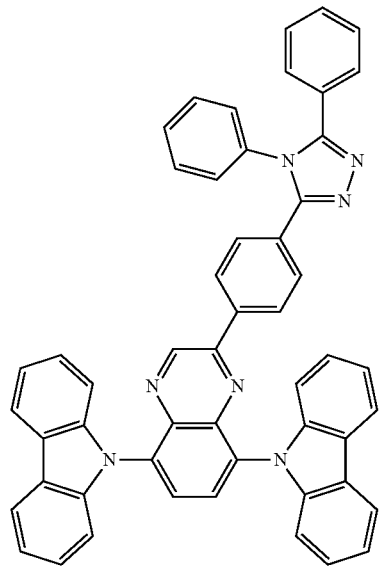
A72
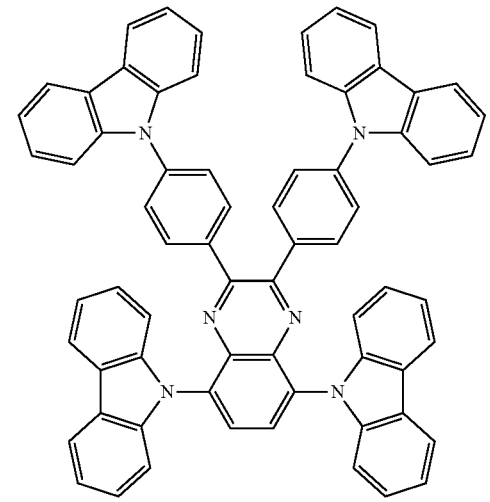
A73
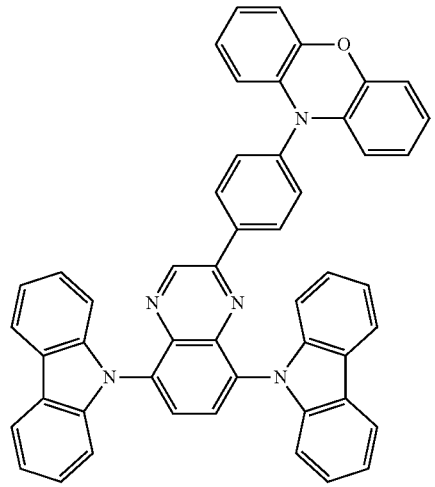
A74
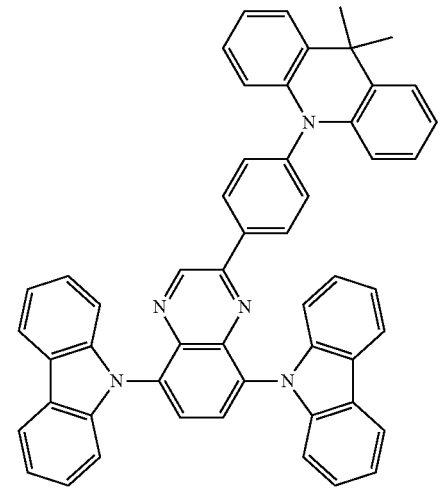

-continued
| | |
|---|---|
| A75 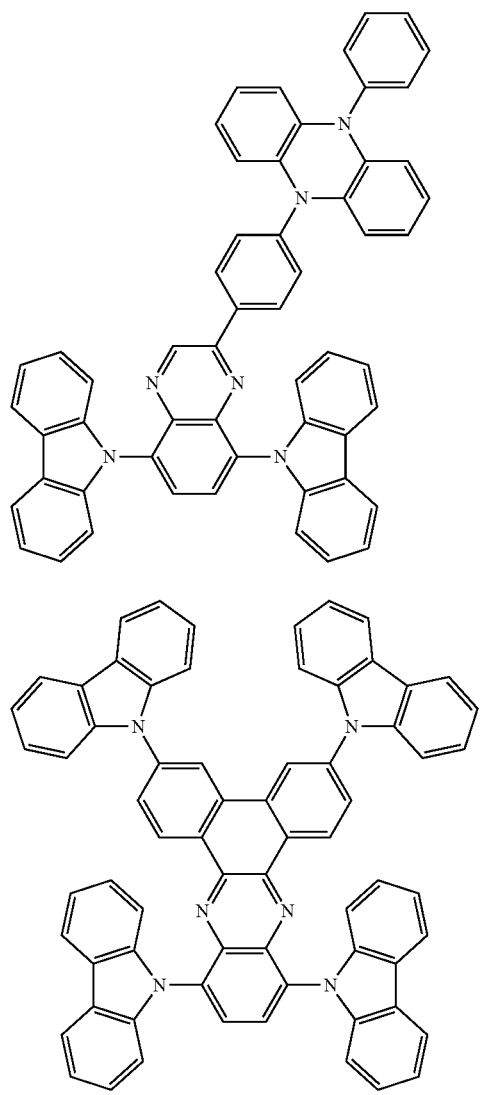 | A76 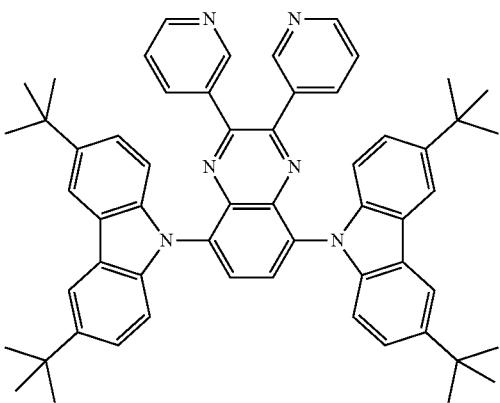 |
| A77 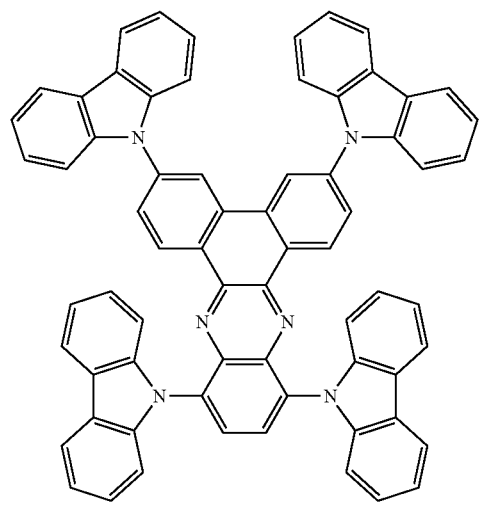 | A78 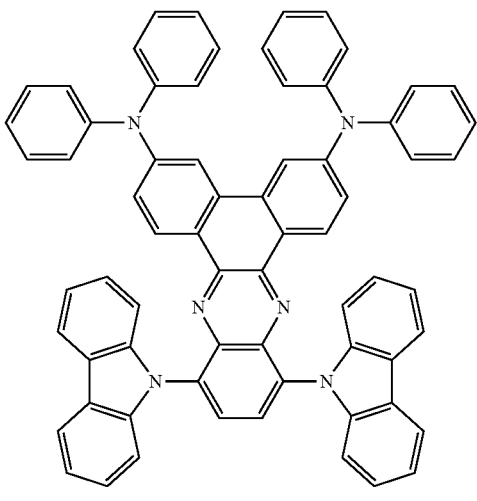 |
| A79 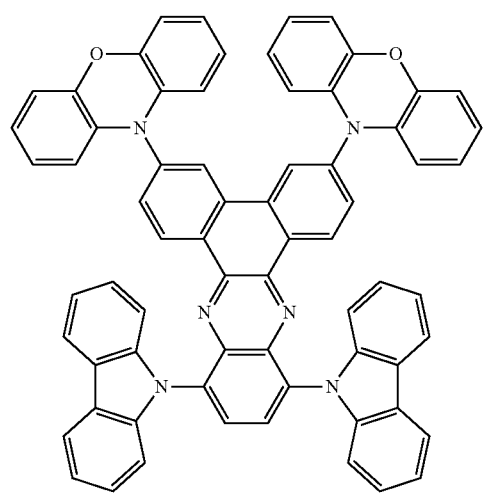 | A80 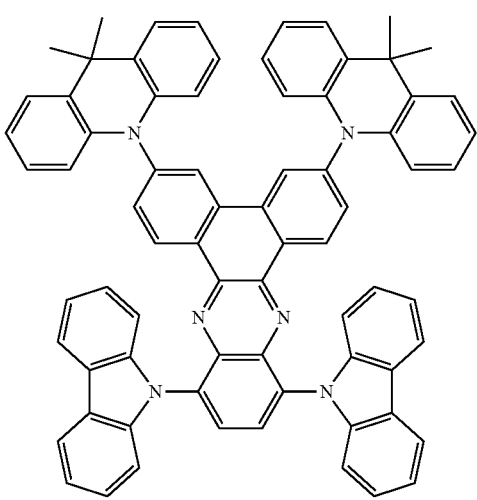 |

-continued
A81
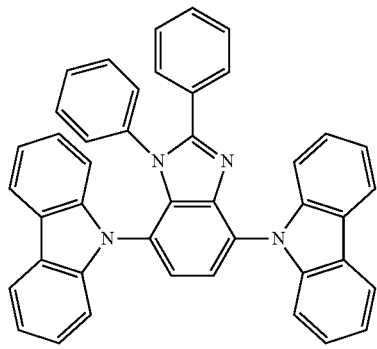
A82
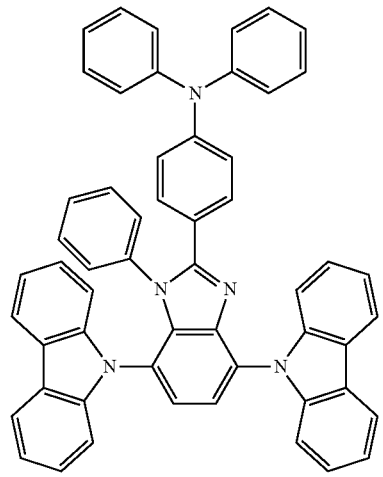
A83
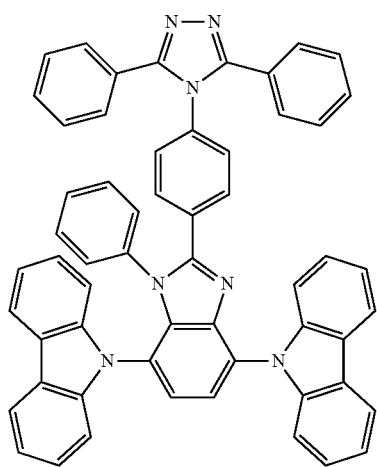
A84
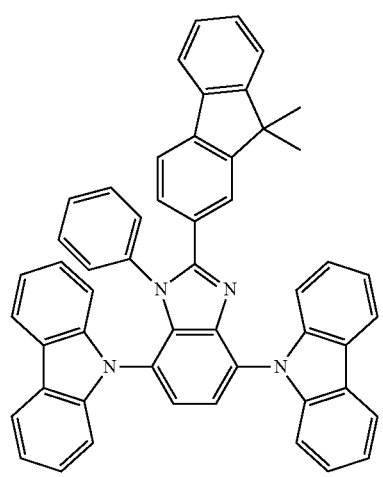
A85
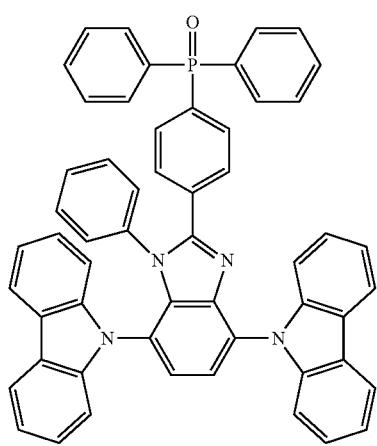
A86
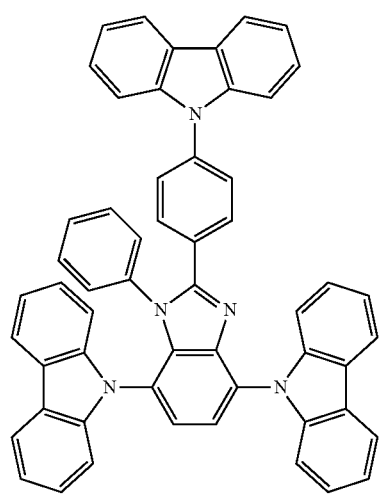

-continued
A87
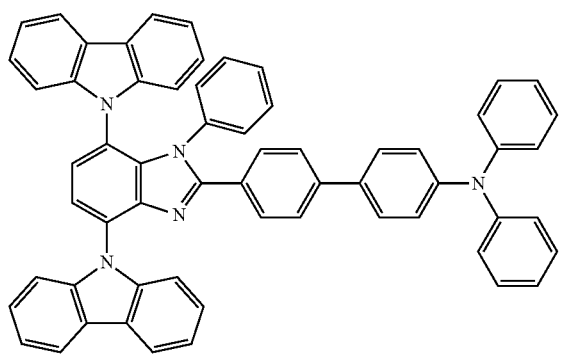
A88
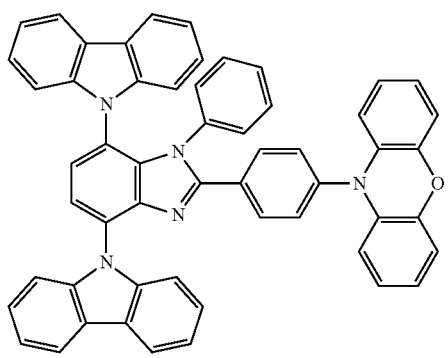
A89
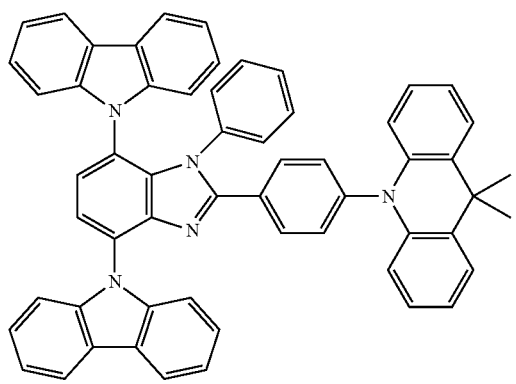
A90
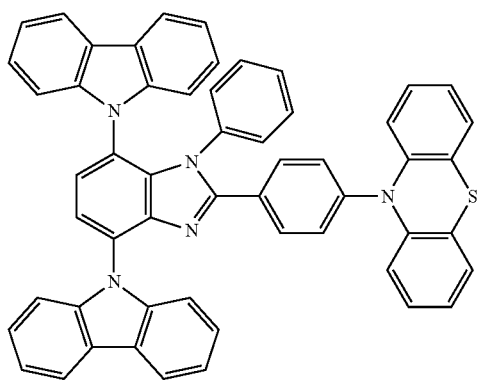
A91
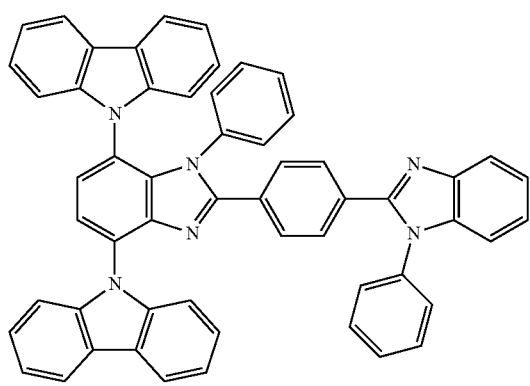
A92
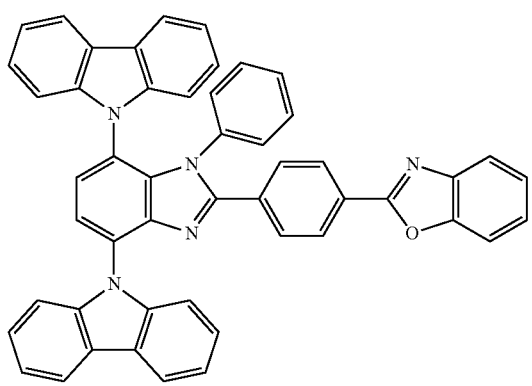
A93
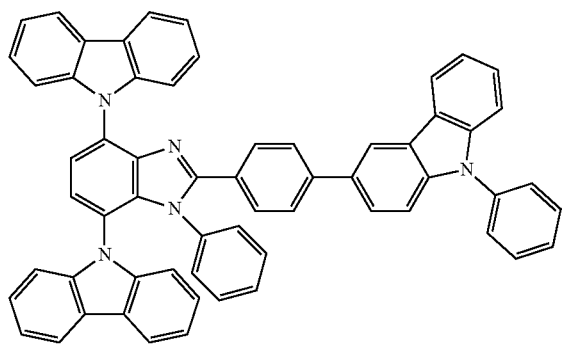
A94
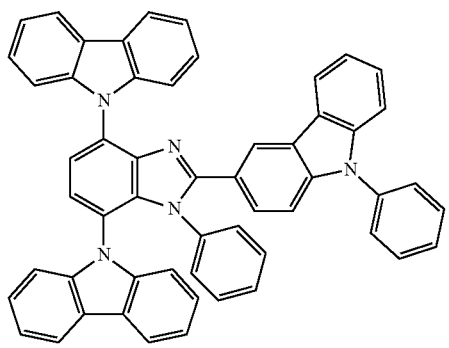

A95

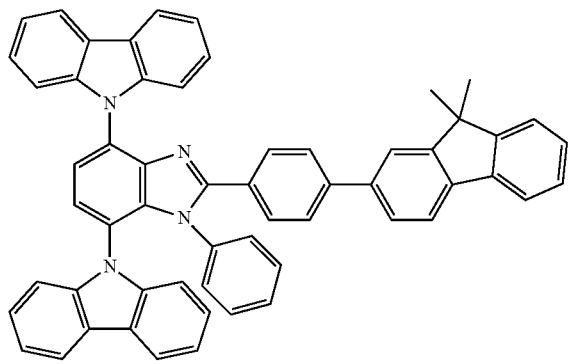

A96

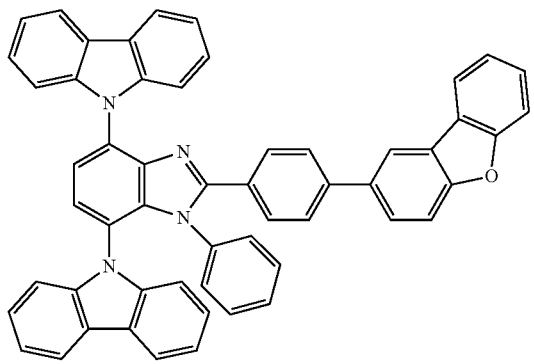

A97

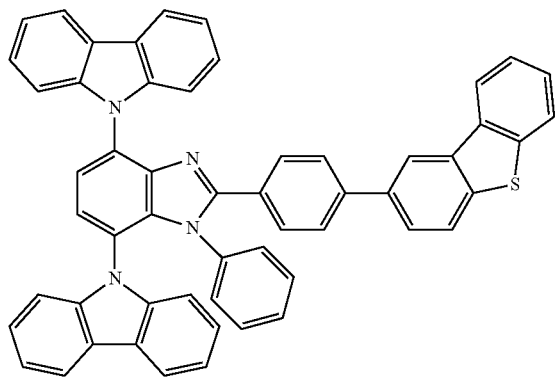

A98

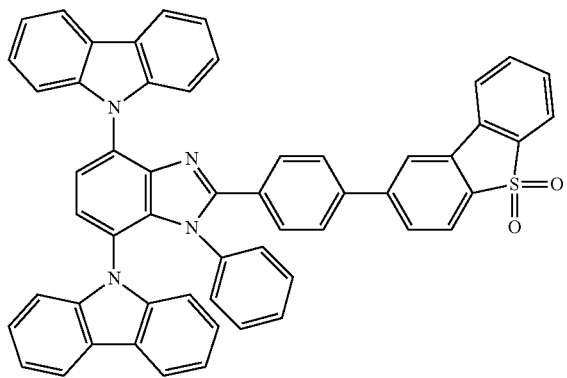

A99

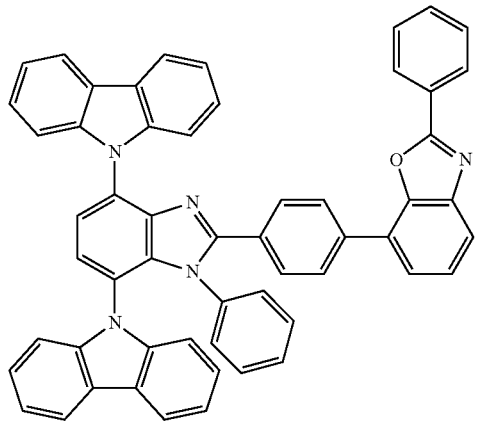

A100

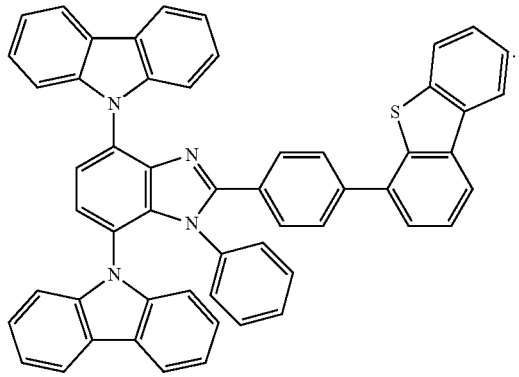

2. An organic electroluminescent device comprising a luminescent layer containing a compound of claim 1.

3. The organic electroluminescent device according to claim 2, wherein the organic electroluminescent device is composed of a transparent substrate, an anode, a hole injection layer, a hole transport layer, an organic light-emitting layer, an electron transport layer and a cathode layer in sequence from the bottom to the top.

4. The organic electroluminescent device according to claim 3, wherein the material constituting said transparent substrate is glass or a flexible substrate; and the material constituting said anode layer is an inorganic material or an organic electrically conductive polymer; wherein said inorganic material is indium tin oxide, zinc oxide, tin zinc oxide, gold, silver or copper; and said organic electrically conductive polymer is selected from at least one of a polythiophene, sodium polyvinylbenzene sulphonate and a polyaniline.

5. The device according to claim 4, wherein said hole injection layer contains one or more of the following compounds:

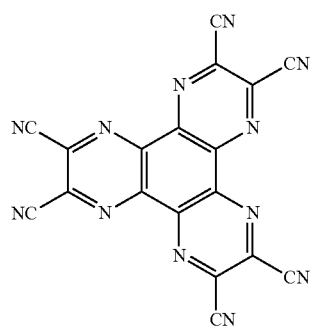
HATCN
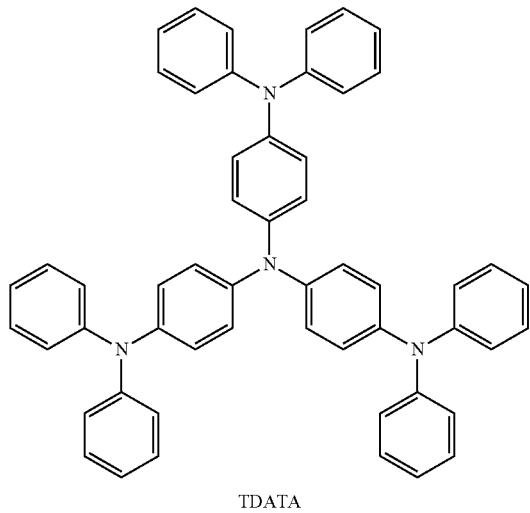
TDATA
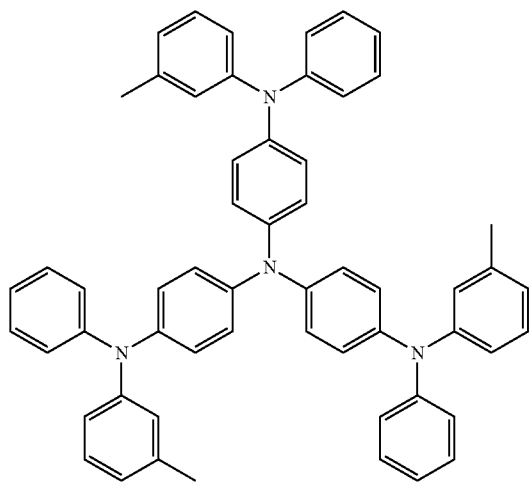
m-MTDATA
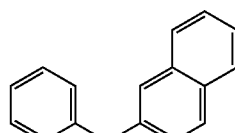
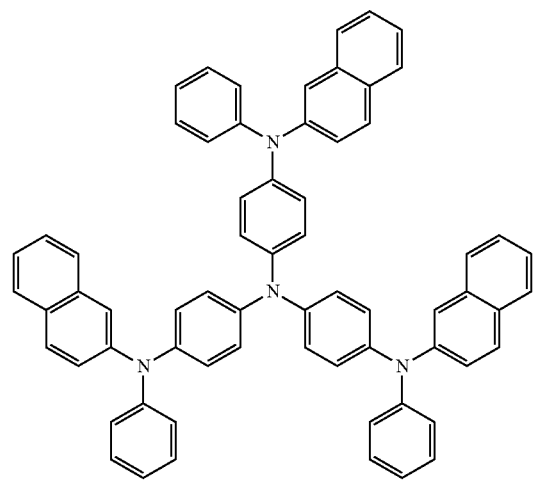
2-TNATA
said hole transport layer contains one or more of the following compounds:
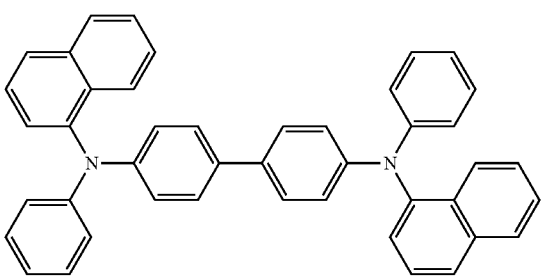
NPB
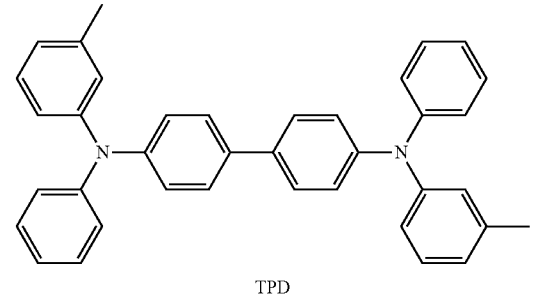
TPD
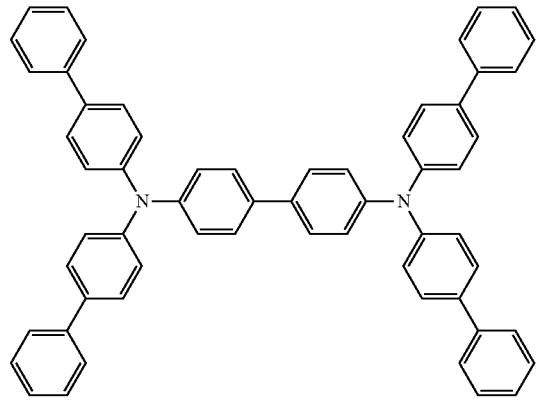
TBPA the material constituting said organic light-emitting layer further comprises one or more of the following materials:
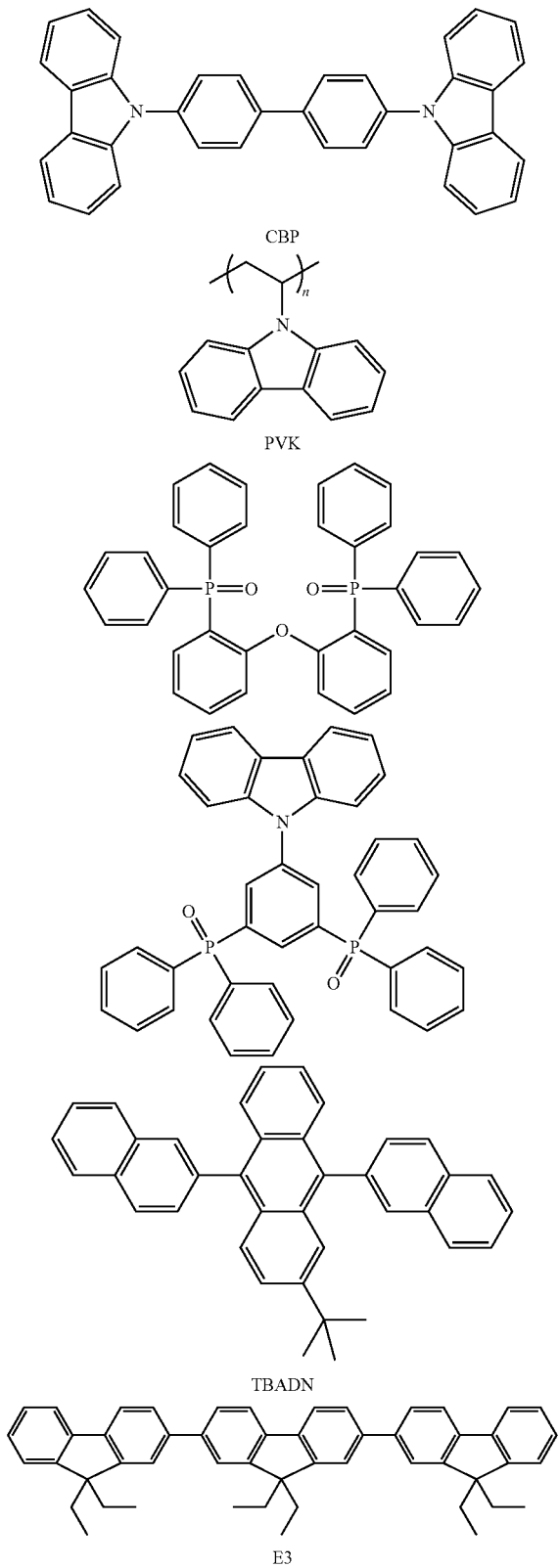
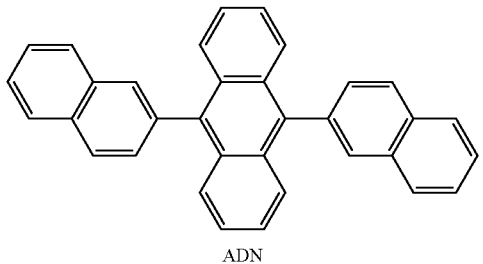
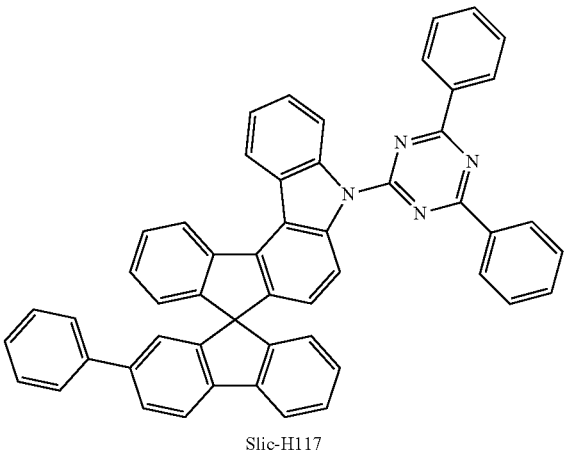
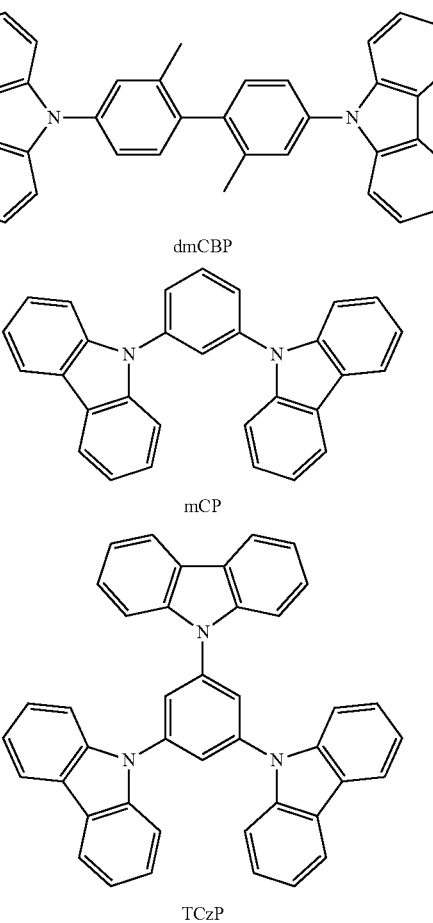

-continued

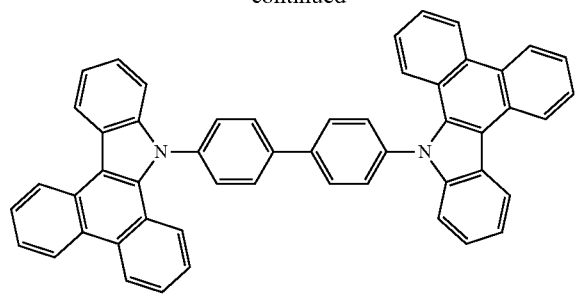

BCPB

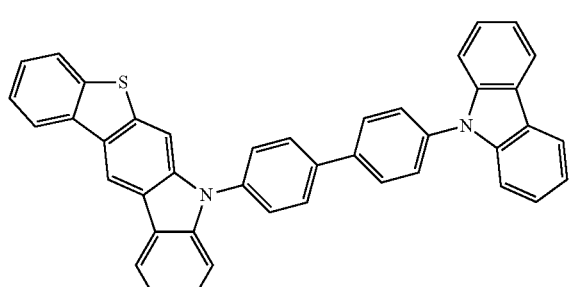

Slic-H065

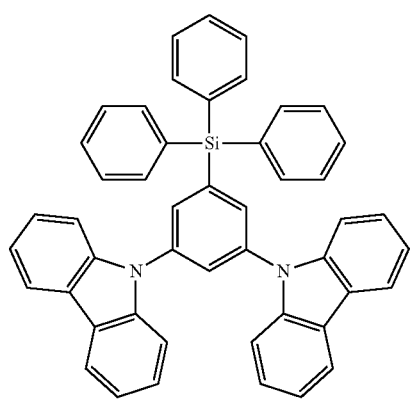

SimCP

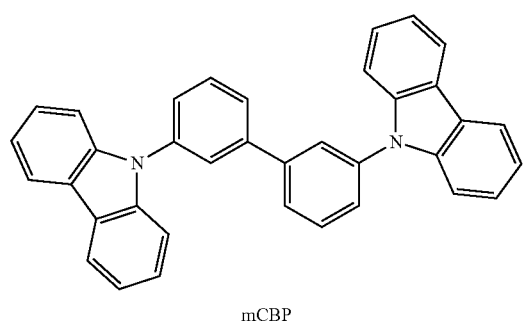

mCBP the material constituting said electron transport layer is Liq, Gaq3, TPBI or Slichem-EL-068, the structures being as follows:

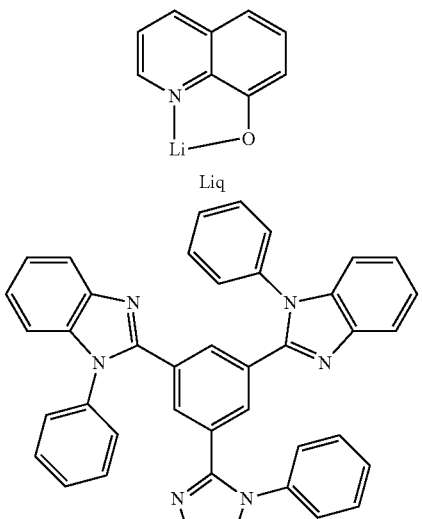

Liq

TPBI

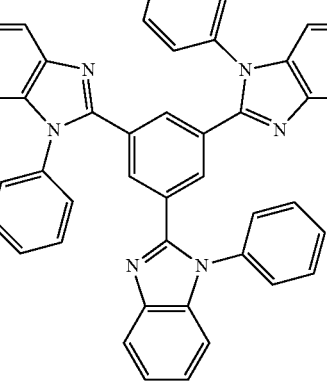

Gaq3

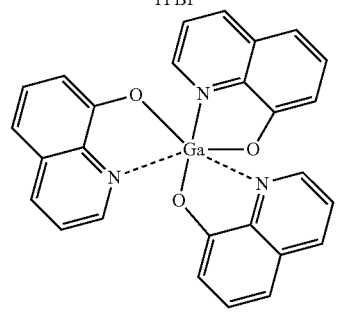

Slichem-EL-068 and the material constituting said cathode layer is selected from any one of or an alloy of any two of or a fluoride of the following elements: lithium, magnesium, silver, calcium, strontium, aluminium, indium, copper, gold and silver.

6. The device according to claim 4, wherein the thickness of said hole injection layer is 30-50 nm; the thickness of said hole transport layer is 5-15 nm; the thickness of said organic light-emitting layer is 10-100 nm; the thickness of said electron transport layer is 10-50 nm; and the thickness of said cathode layer is 90-110 nm.

7. The device according to claim 4, wherein the thickness of said hole injection layer is 40 nm;

the thickness of said hole transport layer is 10 nm;
the thickness of said organic light-emitting layer is 20 nm;
the thickness of said electron transport layer is 40 nm;
and the thickness of said cathode layer is 100 nm.

* * * * *